(12) United States Patent
Palma et al.

(10) Patent No.: US 7,285,674 B2
(45) Date of Patent: Oct. 23, 2007

(54) SILANE MOLECULES WITH PRE-ACTIVATED AND PROTEIN-RESISTANT FUNCTIONALITIES AND SILANE FILMS COMPRISING SUCH MOLECULES

(75) Inventors: Randy De Palma, Maasmechelen (BE); Wim Laureyn, Leuven (BE); Karolien Jans, Hasselt (BE)

(73) Assignee: Interuniversitair Microelektronica Centrum (IMEC), Leuven (BE)

( * ) Notice: Subject to any disclaimer, the term of this patent is extended or adjusted under 35 U.S.C. 154(b) by 85 days.

(21) Appl. No.: 11/120,483

(22) Filed: May 3, 2005

(65) Prior Publication Data

US 2005/0255514 A1 Nov. 17, 2005

Related U.S. Application Data

(60) Provisional application No. 60/569,289, filed on May 6, 2004.

(51) Int. Cl.
*C07F 7/02* (2006.01)
(52) U.S. Cl. .................. 556/400; 556/418; 556/420; 548/955; 546/14
(58) Field of Classification Search ............... 556/418, 556/14, 419, 420, 400; 548/955; 435/6, 435/287.2; 546/14
See application file for complete search history.

(56) References Cited

U.S. PATENT DOCUMENTS 4,960,880 A * 10/1990 Uyeo ..................... 540/200
5,294,501 A * 3/1994 Chaloner-Gill .......... 429/313

FOREIGN PATENT DOCUMENTS

| EP | 528661 | * | 2/1993 |
|----|--------|---|--------|
| GB | 706703 A | | 4/1954 |
| JP | 48016991 | * | 7/1971 |
| JP | 63187603 | * | 1/1997 |
| WO | WO9424720 | * | 4/1994 |

OTHER PUBLICATIONS

Dexheimer et al., Spectral characteristics of acylsilanes, Spectroscopy Letters (1978), 11(10), 751-64.*
Holtmann, Investigations on the glass fiber surface of polyester laminates, Kunststoffe (1967), 57(2), 110-16.*
Byfield, et al. *Biochemical Aspects of Biosensors*, Biosensors and Bioelectronics, 9 (1994) pp. 373-400.
Brzoska, et al. *Silanization of Solid Substrates: A Step toward Reprducibility*, Langmuir (1994) 10, pp. 4367-4373.

(Continued)

*Primary Examiner*—Johann Richter
*Assistant Examiner*—Chukwuma Nwaonicha
(74) *Attorney, Agent, or Firm*—Knobbe Martens Olson & Bear LLP

(57) ABSTRACT

The present invention provides a silane molecule which combines pre-activated and protein-resistant functionalities in one molecule; the molecule has a general formula:

$$A\text{-}(CH_2)_n\text{---}(O[CH_2]_t)_m\text{---}(CH_2)_v\text{---}Y \qquad (1)$$

wherein A is a functional group for binding to a substrate and Y is a functional group for binding to biomolecules. The invention furthermore provides a method for the synthesis of such a silane molecule and a method for depositing a monolayer of such silane molecules onto a substrate. Such a monolayer of silane molecules may be used in biosensors, DNA/protein micro-arrays or other sensor applications. For further lowering the protein binding to the surface of the biosensor, the monolayer may furthermore comprise second silane molecules with formula:

$$B\text{---}(CH_2)_o\text{---}(OCH_2CH_2)_r\text{---}Z. \qquad (4)$$

28 Claims, 21 Drawing Sheets

OTHER PUBLICATIONS

Ghosh, Covalent Attachment of Oligonucleotides to Solid Supports, Nucleic Acids Research, vol. 15, No. 13, 1987, pp. 5353-5372.

Fryxell, et al. *Nucleophilic Displacements in Mixed Self-Assembled Monolayers*, Langmuir (1996) 12, pp. 5064-5075.

Frederix, et al. *Enhanced Performance of an Affinity Biosensor Interface Based on Mixed Self-Assembled Monolayers of Thiols, on Gold*, Langmuir, 2003, 19, pp. 4351-4357.

Gey, et al. *Die Ionisierungenergian Von substituierten Phenyldimethylmethoxysilanen und Phenyldimethyfluorsilanen*, International Journal Of Mass Spectrometry and Ion Physics, vol. 22, 1976, pp. 103-109, XP002349566.

Hertler W. A. et al., *Studies of the Chemistry of Tri(tert-butoxy)silyl isocyanide, Ab Initio calculations of Sily Cyanide/isocyanide energies*: Journal of The American society, vol. 109 No. 21, Oct. 14, 1987, pp. 6532-6533; XP002349567.

Houseman, Maleimide-Funchtionalized Self-Assembled Monolayers for the Preparation of Peptide and Carbohydrate Biochips, Langmuir 19, (2003) 99 1522-1531.

Kane, *Kosmotropes Form the Basis of Protein-Resistant Surfaces*, Langmuir, vol. 19, No. 6, Apr. 18, 2003; pp. 2388-2391; XP002349581.

Krolevets, et al. Organosilicon and Organophosphorus Compounds with Pseudohalogen Groups Bulletin of the Academy of Sciences of the USSR, Division of Chemical Sciences, vol. 40, No. 7, 1991. pp. 1410-1415; XP009055435.

Lee, et al. *Protein Resistant Coating for Glass and Metal Oxide Surfaces Derived from Oligo(ethylene glycol)-terminated alkyltrichlorosilanes*, Biomaterials, 19, (1998) pp. 1669-1675.

Lee, et. al., *Electrophilic Siloxane-Based Self-Assembled Monolayers for Thiol-mediated Anchoring of Peptides and Proteins*, Lanmuir, vol. 9, No. 11 Nov. 1993 pp. 3009-3014; XP002349564.

Love, et al. *Self-Assembled Monolayers of Thiolates on Metals of Thiolates on Metals as a Form of Nanotechnology*, Chemical Reviews vol. 105, No. 4 Apr. 2005 pp. 1103-1169; XP002349570.

Netzer, et al. *A New Approach to Construction of Artificial Monolayer Assemblies*, Journal of the American Chemical Society vol. 105, No. 3, 1983 pp. 674-676, XP002349578.

Netzer, et al. *Adsorbed Monolayers Versus Langmuir-Blodgett Monolayers—Why and How? I From Monolayer to Multilayer, by Adsorption*. Thin Solid Films, 99, (1983) 235-241.

Ostuni, et al. *A Survey of Structure—Property Relationships of Surfaces that Resist the Absorption of Protein*, Langmuir, (2001) 17, pp. 5605-5620.

Sobek, et al. *Substate Architecture and Functionality*, Microarray Technology, Sep. 2004, pp. 32-44.

Schon, J.H., *Organic Insulator/Semiconductor Heterostructure Monolayer Transistors*, Applied Physics Letter, vol. 80 No. 2, Jan. 14, 2002 pp. 323-333; XP012030926.

Ulman, A., *Formation and Structure of Self-Assembled Monolayers*, Chemical Reviews, vol. 96, No. 4, 1996, pp. 1533-1554, XP002116022.

Wasserman, et al. *Monolayers of 11-Tricholorisilylundecyl Thioacetate: A System that Promotes Adhesion Between Silicon Dioxide and Evaporated Gold*. Journal of Materials Research, vol. 4 No. 4 Jul. 1989 pp. 886-892; XP009055390.

Wasserman, et al. *Structure and Reactivity of Alkylsiloxane Monolayers Formed by Reaction of Alkyltrichlorosilanes on Silicon Substrates*, Langmuir (1989) 5, pp. 1074-1087.

Zammatteo, et al. *Comparison between different Strategies of Covalent Attachment of DNA to Glass Surfaces to Build DNA Microarrays*, Analytical Biochemistry, vol. 280, No. 1, Apr. 2000 pp. 143-150.

European Search Report for corresponding European Application No. EP 05 44 7105, Mailed on Nov. 8, 2005.

* cited by examiner

SILANE MOLECULES WITH PRE-ACTIVATED AND PROTEIN-RESISTANT FUNCTIONALITIES AND SILANE FILMS COMPRISING SUCH MOLECULES

CROSS-REFERENCE TO RELATED APPLICATIONS

This application claims the benefit of U.S. Provisional Application No. 60/569,289, filed May 6, 2004. The above-referenced prior application is incorporated by reference herein in its entirety and is hereby made a portion of this specification.

FIELD OF THE INVENTION

The present invention relates to silane molecules, more particularly to silane molecules combining pre-activated and protein-resistant functionalities in one molecule, to a method for synthesising such silane molecules, to silane films formed on substrates comprising such silane molecules and to biosensor devices or micro-array systems comprising such silane films.

BACKGROUND OF THE INVENTION

Health and environmental related fields face various biochemical processes, which have to be evaluated rapidly at decreasing detection levels. A lot of biochemical analytical methods involve immobilisation of a biological sensing element on a surface. The increasing miniaturisation of the detection system and the demand for a high sensitivity impose more severe demand on the immobilisation of such biological sensing elements. Generally, a biosensor comprises a biological sensing element, such as, e.g., an antibody or single-stranded DNA, in close contact with a physico-chemical transducer, such as e.g., an electrode. Measurement of a target molecule, e.g., an antigen or a complementary DNA strand, in an analyte is achieved by selective transduction of a parameter of the biomolecule-analyte interaction into a quantifiable signal.

Two important and desired properties of a biosensor are its specificity and its sensitivity towards the target molecule(s). Biosensors must also fulfil major requirements like stability, speed and reproducibility. In addition, the analyte must be detectable in an excess of other proteins. Because of these strict requirements, affinity biosensors are not yet commercially available. More specifically, the intrinsically high specificity of biomolecular systems can be successfully exploited for the realisation of highly sensitive integrated biosensor devices only if a highly efficient coupling between the biological and transducer components is realised [M. P. Byfield and R. A. Abuknesha, in 'Biochemical aspects of biosensors', Biosensors and Bioelectronics, 9 (1994) pp. 373400]. Therefore, the biological sensing elements are preferably bound on the surface in such a way that a significant and specific interaction with the target molecules occurs. Moreover, a well-defined interface between the transducer surface and the biomolecules will allow control over the reproducibility of the biosensor device and over the extent of non-specific adsorption of any undesired biospecies. For immuno-sensors the most common biological sensing elements are antibodies and specific binding proteins, which have a reversible specific binding affinity for an analyte.

DNA chip technology uses microscopic arrays of DNA molecules immobilized on solid supports for biomedical analysis such as gene expression analysis, polymorphism or mutation detection, DNA sequencing and gene discovery [G. Ramsay, 'DNA chips: state-of-the art'. Nature Biotechnol., 16 (1998) pp. 40-44]. DNA chips generally comprise a glass substrate, as glass is a popular material for DNA chip technology due to its low fluorescence, transparency, low cost and resistance to high temperatures. A variety of non-covalent coupling chemistries have been used to bind DNA onto glass, such as, for example, polylysine coatings or hydrophobic interactions. However, in these cases, DNA films are susceptible to removal from the surface under high salt or high temperature conditions. Covalent binding methods are thus preferred. Usually, DNA is cross-linked by ultraviolet irradiation to form covalent bonds between thymidine residues in the DNA and positively charged amino groups added on the functionalised slides. Alternatively, DNA molecules are fixed at their extremities. Thus, carboxylated or phosphorylated DNA can be coupled to aminated supports as well as the reciprocal situation [S. S. Ghosh and C. F. Musso, 'Covalent attachment of oligonucleotides to solid supports'. Nucleic Acids Res., 15 (1987) pp. 5353-5372]. Amino-terminal oligonucleotides can also be bound to isothiocyanate-activated glass, or to glass surfaces modified with epoxide. Thiol-modified or disulfide-modified oligonucleotides have also been grafted onto aminosilane via a heterobifunctional crosslinker or on 3-mercaptopropylsilane. Zammateo et al. reported that the coupling of aminated DNA to glass supports derivatised with aldehyde groups presents several advantages over other methods [N. Zammatteo et al., 'Comparison between different strategies of covalent attachment of DNA to glass surfaces to build DNA microarrays'. Anal. Biochem., 280 (2000) pp. 143-150]. One of them is that aminated DNA is directly bound without the help of a coupling agent. Time-consuming reactions and unstable reagents such as coupling activators are avoided, making this procedure well suited for DNA chip technology. One drawback is that the aldehyde-amine condensation leads to the formation of imine groups, which are not very stable and must be reduced in stable amines by borohydride treatment.

To date, the main method for the immobilisation of biological moieties on oxide and glass surfaces has involved reaction with functional organo-alkoxysilanes, followed by a covalent attachment of the biological molecule to the newly introduced functional groups on the surface. Examples of silane molecules frequently used for this purpose are (3-aminopropyl)triethoxysilane (APTES), (3-mercaptopropyl)trimethoxysilane (MPTMS) and (3-glycidoxypropyl)dimethylethoxysilane (GPMES). Glass or oxide surfaces can also be modified by silane chemistry to introduce aldehyde functions [N. Zammatteo et al., 'Comparison between different strategies of covalent attachment of DNA to glass surfaces to build DNA microarrays'. Anal. Biochem., 280 (2000) pp. 143-150]. Because this method is a relatively simple means to introduce a variety of functional groups on oxide materials and glass, it is frequently used in the realisation of affinity biosensors. Nevertheless, it is known that the use of these short-chain trialkoxysilanes often leads to highly polymeric, less effective and heterogeneous surfaces, which is a potential disadvantage when preparing surfaces for biosensors [K. Bierbaum, et al., 'A near edge X-ray absorption fine structure spectroscopy and X-ray photoelectron spectroscopy study of the film properties of self-assembled monolayers of organosilanes on oxidised Si(100)'. Langmuir, 11 (1995) pp. 512-518]. These drawbacks can be ascribed primarily to the short alkyl chain length of these molecules (typically propyl-), which is unable to lead to energetically favourable intermolecular (i.e., Van der Waals) interactions, to the relatively low reactivity of the silicon—(m)ethoxy bond and to cross-reactivity of the functional groups (e.g., amino) with the oxide surface.

In order to create a well-defined interface between the transducer surface and the biomolecules, the silane molecules preferably assemble on the surface of a substrate in a uniform monolayer. In theory, this kind of arrangement allows the biomolecules to be attached to the functional moiety of the silane in a similarly uniform fashion. Such a well-organised interface would be of great value for a higher sensitivity and reproducibility of biosensors.

As opposed to the commercial alkyltriethoxysilanes with short alkanes, most commercial alkyltrichlorosilanes generate well-structured self-assembled monolayers (SAMs), when produced under the proper conditions [J. D. Brzoska et al., 'Silanization of solid surfaces: a step toward reproducibility'. Langmuir 10 (1994) pp. 4367-4373]. The SAM formation from chlorosilanes is mainly induced by the longer alkyl chains of the available chlorosilanes (3 to 18 $CH_2$'s), compared to most available ethoxysilanes that only comprise 3 $CH_2$'s. These long alkyl chains enable energetically more favourable intermolecular (i.e., Van der Waals) interactions, resulting in the possible spontaneous formation of ordered monolayers. The use of SAMs provides an easy way to functionalise surfaces by formation of a highly ordered uni-molecular film, with the flexibility to design different head groups on the monolayers. More specifically, hydrophobic and hydrophilic groups at the end of the monolayers provide an excellent possibility to immobilise enzymes, proteins, or whole cells for selective sensing of different analytes. Especially for alkanethiols on metal surfaces, this versatile SAM formation is already a reality [J. C. Love, 'Self-Assembled Monolayers of Thiolates on Metals as a Form of Nanotechnology', Chemical Reviews, ASAP article, 2005].

Unfortunately however, many polar groups suitable for biomolecule immobilisation (such as COOH, $NH_2$ and SH) are incompatible with the highly reactive (i.e., electrophilic) trichlorosilane group. Therefore, such polar functional groups are usually generated from non-polar precursors such as, e.g., Br, C=C, C≡N and others, after formation of a monolayer film of the latter molecules on the biosensor surface [S. R. Wasserman et al., 'Structure and reactivity of alkylsiloxane monolayers formed by reaction of alkyltrichlorosilanes on silicon substrates'. Langmuir 5 (1989) pp. 1074-1087]. To date, the requirement for a post-silanisation surface reaction and the stringent conditions necessary to allow for monolayer formation are the major drawbacks for the implementation of alkylchlorosilanes in the process of immobilising biomolecules, which explains their rare exploitation in biosensor development and micro-array applications.

To allow for surface modification after silanisation, non-nucleophilic terminal groups have to be introduced on the surface first. To this end, SAMs from alkyltrichlorosilanes with termini such as halogen, cyanide, thiocyanide, ether, ester, thioether, thioester, vinyl, α-haloacetate and p-chloromethylphenyl have already been deposited [A. Ulman, 'Formation and structure of self-assembled monolayers'. Chem. Rev., 96 (1996) pp. 1533-1554]. Some of the afore mentioned terminal groups can also be created in situ, for example, by nucleophilic substitution on bromine terminated SAMs, giving rise to thiocyanato, cyanide and azide surfaces. Afterwards, they can be converted to the corresponding mercapto and amino terminated monolayers, by reduction with $LiAlH_4$. Also the modification of vinyl groups by oxidation to obtain hydroxyl or carboxyl terminated monolayers has been studied [L. Netzer and J. Sagiv, 'Adsorbed monolayers versus Langmuir-Blodgett monolayers—why and how?: From monolayer to multilayer, by adsorption'. J. Am. Chem. Soc., 105 (1983), pp. 674-676]. Lee et al. have extensively investigated the reactivity of various halogen terminated SAMS towards nucleophiles such as amino and thiol compounds [Y. W. Lee at al., 'Electrophilic siloxane-based self-assembled monolayers for thiol-mediated anchoring of peptides and proteins'. Langmuir, 9 (1993) pp. 3009-3014]. It was found that the reactivities of the functionalised monolayer were in the order: α-haloacetyl>benzyl halide>>alkyl halide. Moreover, within each class of compounds the reactivity follows the order of leaving groups: I>Br>Cl directly. The most reactive compound, i.e., α-iodoacetyl, has been used to bind cysteine-containing peptides. Also Fryxell et al. have studied nucleophilic displacements between halide terminated SAMs and anionic nucleophiles or between ester terminated SAMs and neutral nucleophiles [G. E. Fryxell et al., 'Nucleophilic displacements in mixed self-assembled monolayers'. Langmuir 12 (1996) pp. 5064-5075]. These synthetic elaborations were also carried out on mixed monolayers in order to create SAMs with a mixed functionality. An alternative approach for the realisation of functional surfaces from alkyltrichlorosilane SAMs is the deposition of protected sulphur containing or (thio)ester terminated alkyltrichlorosilanes. After deprotection, thiol, or carboxyl terminated SAMs can be created [S. R. Wasserman et al., 'Monolayers of 11-trichlorosilylundecyl thioacetate: a system that promotes adhesion between silicon dioxide and evaporated gold'. J. Mater. Res., 4 (1989) pp. 886-892]. However, these protected precursor-silanes often require complex synthesis and/or harsh de-protection conditions. The two most frequently applied post-silanisation surface reactions are the oxidation of vinyl terminated SAMs to create carboxyl groups [J. H. Schon and Z. Bao, 'Organic insulator/semiconductor heterostructure monolayer transistors'. Appl. Phys. Lett., 80 (2) (2002) pp. 332-333] and the nucleophilic substitution of bromine terminated SAMs with azide, followed by reduction, to create amino functional surfaces. These surface modifications have been used in applications ranging from fundamental studies of surface reactions, over controlled multilayer formation and fabrication of organic transistors, to the immobilisation of biomolecules for biosensors.

The deposition of functional organoalkoxysilanes, as well as the performance of surface reactions on SAMs of precursor organohalosilanes, usually give rise to a functional group that has to be activated in situ before attachment of the biological moiety. Possibilities for this type of functional group include, but are not limited to, simple moieties such as carboxyl, amino or a thiol group. However, a preferred route for the immobilisation of biological moieties onto oxide and glass surfaces is the deposition of silane molecules with a highly reactive functional moiety that is compatible with monolayer formation and needs no in situ activation prior to reaction with the biological moiety. For example, the deposition and use of trialkoxysilanes with a maleimide function at the end of the alkane chain, which serves for the direct immobilisation of thiol-terminating molecules, was reported by Lu et al. [H. B. Lu et al., 'Engineered biointerfaces for protein biochip applications'. Presented at the AVS 49th International Symposium, Denver, Colo., USA (Nov. 4-8, 2002), BI+HS+SS–ThM11]. Lee et al. have used various halogen terminated SAMs, which are reactive towards nucleophiles such as amino and thiol compounds. For SAMs of alkane thiols on gold, N-hydroxysuccinimide and maleimide terminated surfaces have been reported for the direct immobilisation of proteins.

Besides the introduction of functional groups that allow covalent binding or physical adsorption of receptor molecules, which in turn allows affinity binding with the analyte, protein-resistant functional groups can also be introduced onto the surface using SAMs. The use of oligo(ethylene glycol)- or PEG-terminated alkyltrichlorosilanes, [$Cl_3Si(CH_2)_{11}(OCH_2CH_2)_nOCH_3$], with n=2 or 3, for the formation of protein-resistant coatings on glass and metal oxide surfaces was described by S. -W. Lee and P. E. Laibinis in 'Protein-resistant coatings for glass and metal oxide surfaces derived from oligo(ethylene glycol)-terminated alkyltrichlorosilanes'. Biomaterials, 19 (1998) pp. 1669-1675. Also for SAMs of alkane thiols on gold, the incorporation of oligo (ethylene glycol) functionalities at the terminus has been applied for lowering the non-specific adsorption of proteins on surfaces. Functional groups, other than ethylene glycol, that give surfaces the ability to resist the non-specific adsorption of proteins from solution, have been described by E. Ostuni et al. in 'A survey of structure-property relationships of surfaces that resist the adsorption of proteins'. Langmuir, 17 (2001), pp. 5605-5620' and by R. S. Kane et al. in 'Kosmotropes form the basis of protein-resistant surfaces'. Langmuir, 19 (2003), pp. 2388-2391". However, the incorporation of these alternative groups into single-component SAMs resulted in surfaces that are comparable to, but slightly less good than, single-component SAMs that present oligo(ethylene glycol) in their ability to resist the adsorption of proteins.

Ideally, not all molecules in a monolayer are identical and mixed monolayers are created. For instance, the first molecule in the monolayer serves to immobilise a biological moiety and the second molecule contains a functional group that is resistant to the non-specific binding of biomolecules. For alkyltrichlorosilanes, mixed monolayers have been used to tailor the surface properties of a silanised surface by introducing various functional groups on the terminus of the silane monomers. It has been shown that through the use of such mixed monolayers the properties of the surface can be varied in a continuous manner from one type to another [G. E. Fryxell et al., 'Nucleophilic displacements in mixed self-assembled monolayers'. Langmuir 12 (1996) pp. 5064-5075].

Ideally, silanes with a hydrophilic termination are preferably chosen for the creation of biosensor surfaces, because they are able to resist the non-specific adsorption of biomaterial in a further stage. Unfortunately however, such mixed silane films have not been realised yet. Frederix et al. report mixed self-assembled monolayers (SAMs) of alkane thiols on gold, in which the two functionalities are simultaneously incorporated on the SAM coated gold surface [F. Frederix et al., 'Enhanced performance of a biological recognition layer based on mixed self-assembled monolayers of thiols on gold'. Langmuir, 19 (2003), pp. 4351-4357]. The properties of the mixed SAMs fulfill the necessary requirements to achieve stable and well-ordered mixed SAMs. Their use as an affinity biosensor interface for immuno-sensor applications was evaluated using SPR. In this study, the amount of the different components in the mixed SAMs was optimised with regard to antibody immobilization, antigen recognition, and non-specific adsorption. It was found that a mixed SAM deposited from a mixed solution of 5% of 16-mercaptohexanoic acid and 95% of 11-mercaptoundecanol exhibits the most favourable properties. Their stability and their excellent qualities concerning non-specific adsorption makes these mixed SAMs very useful as a basis for the development of affinity biosensor interfaces for real diagnostic applications or immuno-sensors.

Alternatively, oligo(ethylene glycol) functionalities are incorporated into a homogeneous protein-binding monolayer film such as, for example, self-assembled monolayers of carboxy-functionalized poly(ethylene glycol)alkane thiols [$HOOC—CH_2—(OCH_2CH_2)n—O—(CH_2)_{11})—SH$], with n=22-45, which hav protein resistant and specific antigen binding capability after covalent antibody binding onto the monolayer.

Ideally, mixed SAMs are created from molecules with a highly reactive functional moiety that needs no in situ activation prior to reaction with the biological moiety (also called pre-activated biological moieties) and from molecules that have the ability to resist the non-specific adsorption of proteins. Even more ideally, protein-resistant functionalities are also incorporated in the first type of molecule. For example, Houseman et al. have reported on such a thiol monolayer that presents both maleimide and penta(ethylene glycol) on the surface and that are able to simultaneously react with thiol-terminated ligands and prevent the non-specific adsorption of proteins onto the mixed functional surface [B. T. Houseman et al, 'Maleimide-functionalized self-assembled monolayers for the preparation of peptide and carbohydrate biochips', Langmuir, 19 (2003), pp. 1522-1531].

However, as these molecules comprise thiol-functional groups, they can not be attached to glass and oxide-substrates, and hence are limited in their applicability.

SUMMARY OF THE INVENTION

It is an object to provide a silane molecule and a method for the synthesis of such a silane molecule which forms well-defined and tunable monolayers when deposited onto a substrate and/or which is suitable to be used in biosensors and micro-array applications.

The above objective(s) is (are) accomplished by a method and device according to the preferred embodiments.

In a first aspect, a silane molecule is provided comprising activated and protein-resistant functionalities in one molecule. The silane molecule according to the first aspect has the general formula:

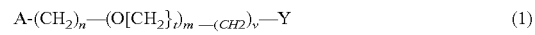

$$A\text{-}(CH_2)_n—(O[CH_2]_t)_m —_{(CH2)_v}—Y \quad (1)$$

wherein A is one of $X_3S_1$, $X_2R^1S^1$, $XR^1R^2Si$ with X a halo or alkoxy group and $R^1$ and $R^2$ an alkyl chain, Y is selected from the group consisting of a conjugated carbonyl, epoxy, nitriloacetic acid, cyano, hydrazide, aziridine, sulfonylchloride, trifluoromethyldiaziridine, pyridylsulfide, N-acetyl-imidazole, vinylsulfone, arylazide, anhydride, diazoacetate, haloacetyl, benzophenone, isothiocyanate, isocyanate, halogen substituted benzene, pyridyldisulfide, biotin, protected carboxyl, protected amine, protected sulfohydryl, protected maleimide, and n is from 0 to 30, m is from 0 to 50, v is from 0 to 5 and t is from 1 to 10.

An advantage of the silane molecules according to this first aspect is that they combine a protein-resistant function with a pre-activated or recognising function. In that way, only one molecule has to be provided at a surface of a substrate of, for example, a biosensor in order to provide the sensor with a recognising or pre-activated function and a protein-resistant function. Furthermore, due to the —(CH$_2$)$_n$— chains, a well ordered self-assembling silane layer can be obtained when depositing the silane molecule to a substrate (see further). Moreover, because of the flexibility of the alkylene glycol chain, the silane molecule is less rigid and thus causes less steric hindrance during the analyte recognition.

Preferably, the Y-group can be a conjugated carbonyl and can be selected from the group, but is not limited to this group, consisting of fluor substituted benzoate, pentafluorophenylester, N-hydroxysuccinimide ester, acid halogenide or maleimide. Unlike other carbonyl function such as, e.g., aldehydes (—CH=O), conjugated carbonyls are functional groups which are compatible with the silylation step necessary to introduce a silane functionality in the final synthesis step of the silane molecule according to the first aspect (see further). In order to retain the pre-activated coupling properties of the carbonyl it is desired that the silylation occurs selectively on the alkene instead of on the carbonyl in the coupling group. Silylation of a carbonyl however, is more likely to occur compared to the alkene due to the high affinity of Si for O. However, when these carbonyls are conjugated, they are protected against this silylation reaction. Conjugated carbonyls comprise all carbonyls that comprise an electronegative heteroatom (e.g., N or O) adjacent to the carbonyl function or that comprise an α,β-unsaturated function or a combination of both. The adjacent heteroatom is preferably, but is not restricted to, a part of the spacer.

In various embodiments of the first aspect, A is Cl$_3$Si— or (EtO)$_3$Si—.

According to various embodiments of the first aspect, R$^1$ and R$^2$ is CH$_3$— or CH$_3$—CH$_2$— and X is Cl, OCH$_3$ or OCH$_2$CH$_3$.

In the (CH$_2$)$_n$ chain n can be from 6 to 22, preferably from 8 to 18. The (CH$_2$)$_n$ chain can comprise p heteroatoms, p being such that n+p is from 0 to 30.

The (CH$_2$)$_v$ chain can comprise q heteroatoms, q being such that v+q is from 0 to 5. In specific cases and for silane molecules comprising particular Y groups such as, e.g., maleimide, this spacer can be absent, i.e., v is zero.

In the (O[CH$_2$]$_t$)$_m$ chain t can be from 1 to 5. Preferably t is 2, in that way forming an oligo(ethylene glycol) chain. M can be from 3 to 22, preferably from 3 to 6.

In a second aspect, a method for the synthesis of the silane molecule according to the first aspect is provided, the silane molecule having the general formula:

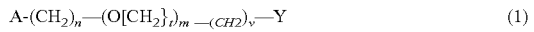  (1)

wherein
A is one of X$_3$S$_1$, X$_2$R$^1$S$^1$, XR$^1$R$^2$Si with X a halo or alkoxy group and R$^1$ and R$^2$ an alkyl chain,
Y is selected from the group consisting of a conjugated carbonyl, epoxy, nitriloacetic acid, cyano, hydrazide, aziridine, sulfonylchloride, trifluoromethyldiaziridine, pyridylsulfide, N-acetyl-imidazole, vinylsulfone, arylazide, anhydride, diazoacetate, haloacetyl, benzophenone, isothiocyanate, isocyanate, halogen substituted benzene, pyridyidisulfide, biotin, protected carboxyl, protected amine, protected sulfohydryl, protected maleimide, and
n is from 0 to 30, m is from 0 to 50, v is from 0 to 5 and t is from 1 to 10.

The method comprises:
Providing an alcohol with general formula:

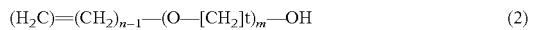  (2)

wherein n can be from 0 to 30, preferably from 6 to 22 and most preferably from 8 to 18, m is from 0 to 50, preferably from 3 to 22 and most preferably from 3 to 6 and t can be from 1 to 10, preferably from 1 to 5, and most preferably t can be 2. The (CH$_2$)$_{n-1}$-chain may optionally comprise p heteroatoms, p being such that n+p is from 0 to 30.

Converting said alcohol to a molecule having a functional group Y and optionally comprising a spacer, hence forming an intermediate with formula:

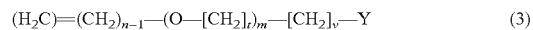  (3)

There are two preferred ways to obtain formula (3). A first way is by directly replacing the OH-group by a suitable Y group. Another way is by first converting the OH-group in another reactive end group such as, e.g., a NH$_2$-group and then replacing the molecule with the other reactive end group to a molecule comprising a Y-group. Both methods can, but this is not necessarily so, result in the presence of a spacer (CH$_2$)$_v$ between the Y function and the alkyleneglycol chain Providing said molecule with formula (3) with an A-group, forming the silane molecule with general formula:

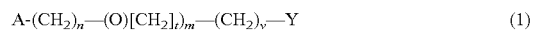  (1)

wherein A is preferably one of X$_3$Si, X$_2$R$^1$Si, and XR$^1$R$^2$Si, wherein X can be a halo or alkoxy group, preferably a chloro- or an ethoxy group and wherein R$^1$ and R$^2$ can be one of CH$_3$— or CH$_3$—CH$_2$— or another alkyl chain, which can optionally be interrupted by heteroatoms. Preferably, A is Cl$_3$Si— or EtO$_3$Si—.

Preferably, the Y-group is a conjugated carbonyl and is selected from the group, but are not limited to this groups, consisting of fluor substituted benzoate, pentafluorophenylester, N-hydroxysuccinimide ester, acid halogenide or maleimide.

According to various embodiments of the second aspect, providing an alcohol with general formula (2) is performed by: reacting a halogenated alkene with formula:

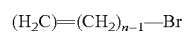

with an alkylene glycol with formula:

In various embodiments of the second aspect, A is Cl$_3$Si— or (EtO)$_3$Si—.

According to various embodiments of the second aspect R$^1$ and R$^2$ is CH$_3$— or CH$_3$—CH$_2$— and X is —Cl, —OCH$_3$ or —OCH$_2$CH$_3$.

In the (CH$_2$)$_n$ chain n can be from 6 to 22, preferably from 8 to 18. The (CH$_2$)$_n$ chain can comprise p heteroatoms, p being such that n+p is from 0 to 30.

The (CH$_2$)$_v$ chain can comprise q heteroatoms, q being such that v+q is from 0 to 5. In specific cases and for silane molecules comprising particular Y groups such as, e.g., maleimide, this spacer can be absent, i.e., v is zero.

In the (O[CH$_2$]$_t$)$_m$ chain t can be from 1 to 5. Preferably t is 2, in that way forming an oligo(ethylene glycol) chain. M can be from 3 to 22, preferably from 3 to 6.

In a third aspect, a substrate comprising a self-assembled monolayer comprising first silane molecules is provided, the first silane molecules having the general formula:

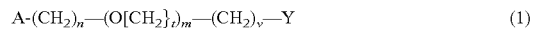  (1)

wherein
- A is one of $X_3Si$, $X_2R^1Si$, $XR^1R^2Si$ with X a halo or alkoxy group and $R^1$ and $R^2$ an alkyl chain,
- Y is selected from the group consisting of a conjugated carbonyl, epoxy, nitriloacetic acid, cyano, hydrazide, aziridine, sulfonylchloride, trifluoromethyldiaziridine, pyridylsulfide, N-acetyl-imidazole, vinylsulfone, arylazide, anhydride, diazoacetate, haloacetyl, benzophenone, isothiocyanate, isocyanate, halogen substituted benzene, pyridyldisulfide, biotin, protected carboxyl, protected amine, protected sulfohydryl, protected maleimide, and
- n is from 0 to 30, m is from 0 to 50, v is from 0 to 5 and t is from 1 to 10.

Preferably, the Y-group is a conjugated carbonyl and is selected from the group consisting of fluor substituted benzoate, pentafluorophenylester, N-hydroxysuccinimide ester, acid halogenide or maleimide.

In various embodiments of the third aspect, A is $Cl_3Si$— or $EtO_3Si$—.

According to various embodiments of the third aspect, $R^1$ and $R^2$ is $CH_3$— or $CH_3$—$CH_2$—.

In the $(CH_2)_n$ chain n can be from 6 to 22, preferably from 8 to 18. The $(CH_2)_n$ chain can comprise p heteroatoms, p being such that n+p is from 0 to 30.

The $(CH_2)_v$ chain can comprise q heteroatoms, q being such that v+q is from 0 to 5. In specific cases and for silane molecules comprising particular Y groups such as, e.g., maleimide, this spacer is absent, i.e., v is zero.

In the $(O[CH_2]_t)_m$ chain t can be from 1 to 5. Preferably t is 2, in that way forming an oligo(ethylene glycol) chain. M can be from 3 to 22, preferably from 3 to 6.

For further lowering the protein binding to the surface of, e.g., a biosensor or a micro-array substrate, the monolayer can furthermore comprise second silane molecules with formula:

B is a functional group for binding to a substrate and is one of $W_3Si$, $W_2R^1Si$, $WR^1R^2Si$ with W a halo or alkoxy group and $R^1$ and $R^2$ an alkyl chain, Z is a moiety resistant to non-specific binding of biomolecules and is one of a hydroxyl group, an alkoxy group, a saccharide or an oligo/polyethylene glycol moiety, and o is from 0 to 30, r is from 0 to 50 and x is from 1 to 10.

An advantage of forming a mixed monolayer on a substrate, the mixed monolayer comprising first and second silane molecules as described above, is that the protein-resistance, and thus the specificity, is enhanced. Furthermore, the sensitivity can be increased by reducing the steric hindrance between receptors. These properties can be tuned by varying the ratio between the first and the second silane molecule on the substrate.

In various embodiments, Z is a methoxy or an ethoxy group.

In the —$(CH_2)_o$— chain o can be from 6 o 22, preferably from 8 to 18. In the —$(O[CH_2]x)_r$— chain r can be from 3 to 22, preferably from 3 to 6 and x can be from 1 to 5 and is most preferably be 2.

The substrate is preferably an inorganic or an organic substrate. Inorganic substrates can for example comprise, but is not limited to, silicon, glass, silica, quartz, metal oxides, and the like. Metal oxide or glass substrates can include, but are not limited to, silicon oxide, indium tin oxide, magnesium oxide, titanium oxide, tantalum oxide, zirconium oxide, niobium oxide, palladium oxide, platinum oxide, ruthenium oxide, quartz, glass, or silica. Organic substrates can comprise organic polymers such as, e.g., polyvinyl alcohol polymers, acrylic acid polymer and others. The substrates can be modified to obtain reactive groups such that the silane molecules can bound onto the substrate. In various embodiments, the substrate is preferably in the form of an optical fibre, a wire, wafer, discs, planar surfaces, microscope slides, or nano/micrometer sized particles. The substrate can also be a sensor, a biosensor, a DNA chip, a protein chip, a microarray, a microscope slide, a silicon wafer, or a microelectronic surface. Furthermore, the substrate can be a part of a transducer, which can be, but is not limited to, a Surface Plasmon Resonance (SPR) sensor, Surface Acoustic Wave (SAW) sensors, Optical Waveguide Sensor, Quartz Crystal Microbalance, amperometric sensors, capacitive sensors, interdigitated electrodes or chem-FET sensors.

In a fourth aspect a biosensor or micro-array substrate is provided comprising a monolayer which comprises first silane molecules having the general formula:

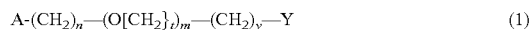

wherein
- A is one of $X_3Si$, $X_2R^1Si$, $XR^1R^2Si$ with X a halo or alkoxy group and $R^1$ and $R^2$ an alkyl chain,
- Y is selected from the group consisting of a conjugated carbonyl, epoxy, nitriloacetic acid, cyano, hydrazide, aziridine, sulfonylchloride, trifluoromethyldiaziridine, pyridylsulfide, N-acetyl-imidazole, vinylsulfone, arylazide, anhydride, diazoacetate, haloacetyl, benzophenone, isothiocyanate, isocyanate, halogen substituted benzene, pyridyldisulfide, biotin, protected carboxyl, protected amine, protected sulfohydryl, protected maleimide, and
- n is from 0 to 30, m is from 0 to 50, v is from 0 to 5 and t is from 1 to 10.

Preferably, the Y-group is a conjugated carbonyl and is selected from the group, but are not limited to the group consisting of fluor substituted benzoate, pentafluorophenylester, N-hydroxysuccinimide ester, acid halogenide or maleimide.

In embodiments of the fourth aspect, A can be $Cl_3Si$— or $EtO_3Si$—.

According to embodiments of the fourth aspect, $R^1$ and $R^2$ can be $CH_3$— or $CH_3$—$CH_2$— and X can be —Cl, —$OCH_3$ or —$OCH_2CH_3$.

In the $(CH_2)_n$ chain n can be from 6 to 22, preferably from 8 to 18. The $(CH_2)_n$ chain can comprise p heteroatoms, p being such that n+p can be from 0 to 30.

The $(CH_2)_v$ chain can comprise q heteroatoms, q being such that v+q can be from 0 to 5. In specific cases and for silane molecules comprising particular Y groups such as, e.g., maleimide, this spacer can be absent, i.e., v can be zero.

In the $(O[CH_2]_t)_m$ chain t can be from 1 to 5. Preferably t can be 2, in that way forming an oligo(ethylene glycol) chain. M can be from 3 to 22, preferably from 3 to 6.

For further lowering the protein binding to the surface of, e.g., a biosensor or a micro-array substrate, the monolayer can furthermore comprise second silane molecules with formula, hereby forming a mixed silane monolayer:

B is a functional group for binding to a substrate and is one of $W_3Si$, $W_2R^1Si$, $WR^1R^2Si$ with W a halo or alkoxy group and $R^1$ and $R^2$ an alkyl chain, Z is a moiety resistant to non-specific binding of biomolecules and is one of a hydroxyl group, an alkoxy group, a saccharide or an oligo/polyethylene glycol moiety, and o is from 0 to 30, r is from 0 to 50, and x is from 1 to 10.

An advantage of forming a mixed monolayer on a substrate, the mixed monolayer comprising first and second silane molecules as described above, is that the protein-resistance, and thus the specificity, is enhanced. Furthermore the sensitivity can be increased by reducing the steric hindrance between receptors. These properties can be tuned by varying the ratio between the first and the second silane molecule on the substrate.

In embodiments according to the fourth aspect, Z can be a methoxy or an ethoxy group.

In the —$(CH_2)_o$— chain o can be from 6 or 22, preferably from 8 to 18. In the —$(O[CH_2]_x)_r$— chain r can be from 3 to 22, preferably from 3 to 6 and x can be from 1 to 5 and can most preferably be 2.

Particular and preferred aspects are set out in the accompanying independent and dependent claims. Features from the dependent claims can be combined with features of the independent claims and with features of other dependent claims as appropriate and not merely as explicitly set out in the claims.

These and other characteristics, features and advantages of the preferred embodiments will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
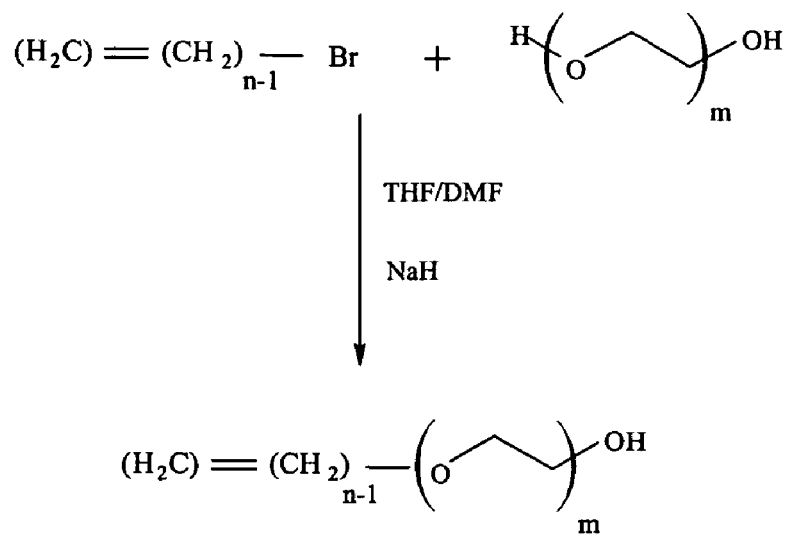
FIG. 1 illustrates a first step in the synthesis of silane molecules according to embodiments of the invention.

In the different figures, the same reference signs refer to the same or analogous elements.

DETAILED DESCRIPTION OF THE PREFERRED EMBODIMENT

The following terms are provided solely to aid in the understanding of the preferred embodiments. These definitions should not be construed to have a scope less than understood by a person of ordinary skill in the art.

with biological moieties is meant all suitable materials which can bind to the self assembled layer in order to bind target molecules present in an analyte to be analysed. The biological moieties that are able to interact/bind with the functional Y groups can be, but are not limited to, nucleic acid strands (DNA, PNA, RNA), cell body, membrane component, proteins, hormones, antibiotics, antibodies, chemically or enzymatically modified antibodies, VHH fragments of lama or camel antibodies, synthetic receptors, single chain Fv's, antigens, enzymes, or drugs.

with target molecules, molecules are meant which are to be detected or determined in an analyte and which can interact or bind with biologically-sensitive materials present on the self assembled layer. The target molecules can be complementary nucleic acid strands (DNA, PNA, RNA), proteins, hormones, antibiotics, antibodies, antigens, enzymes, drugs, drugs of abuse, or molecules such as specific molecules present in for example gases and liquids.

with a protected group is meant a group that is attached to the silane molecule and which needs to be deprotected to form an active group, before it can bind biological moieties pre-activated functionality indicates the capability of a certain class of coupling groups to directly interact with biological or chemical moieties without the use of coupling agents. This interaction is most often be based on covalent coupling of the desired biological/chemical moieties via certain chemical functions present in these moieties such as, e.g., $NH_2$, SH, OH, etc.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. The terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. The terms so used are interchangeable under appropriate circumstances and that the embodiments of the invention described herein are capable of operation in other orientations than described or illustrated herein.

The term "comprising," used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof.

The invention will now be described by a detailed description of several embodiments. It is clear that other embodiments can be configured according to the knowledge of persons skilled in the art without departing from the true spirit or technical teaching of the invention.

The preferred embodiments provide a silane molecule combining pre-activated and protein-resistant functionalities in one molecule and a method for the synthesis of such a silane molecule. The preferred embodiments furthermore provide a method for the deposition of a silane film comprising such silane molecules or comprising at least two different silane molecules onto a substrate and thus forming a substrate comprising a silane layer comprising silane molecules according to the preferred embodiments and the application of such a silane film in biosensors, DNA/protein micro-arrays, or other sensor applications. In the further description, with the term silane film is meant a layer comprising one (=monolayer) or more layers of silane molecules according to the preferred embodiments.

In a first aspect, a silane molecule is provided which incorporates pre-activated and protein-resistant functionalities into the same molecule. The silane molecule according to this first aspect has the general formula:

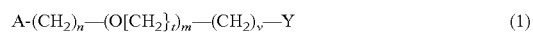

$$A\text{-}(CH_2)_n\text{---}(O[CH_2]_t)_m\text{---}(CH_2)_v\text{---}Y \qquad (1)$$

and comprises the following parts:
1) The A-functionality has the ability to covalently bind or adsorb onto a substrate.

The substrate can be an inorganic or an organic substrate. Inorganic substrates can for example comprise, but is not limited to, silicon, glass, silica, quartz, metal oxides, and the like. Metal oxide or glass substrates can be, but are not limited to, silicon oxide, indium tin oxide, magnesium oxide, titanium oxide, tantalum oxide, zirconium oxide, niobium oxide, palladium oxide, platinum oxide, ruthenium oxide, quartz, glass, or silica. Organic substrates can comprise organic polymers such as, e.g., polyvinyl alcohol polymers, acrylic acid polymer and others. The substrates can be modified to obtain reactive groups such that the silane molecules can be bound onto the substrate. In preferred embodiments, the substrate can be in the form of an optical fibre, a wire, wafer, discs, planar surfaces, microscope slides, or beads. The substrate can also be a sensor, a biosensor, a DNA chip, a protein chip, a microarray, a microscope slide, a silicon wafer, or a microelectronic surface. Furthermore, the substrate can be a part of a transducer, which can be, but is not limited to, a Surface Plasmon Resonance (SPR) sensor, Optical Waveguide Sensor, Surface Acoustic Wave (SAW) sensors, Quartz Crystal, amperometric sensors, capacitive sensors, interdigitated electrodes, or chemFET sensors. The substrate can be prepared (or cleaned) prior to silanisation, in order to introduce reactive hydroxyls and/or to introduce the right amount of water. The surface can also be a surface having magnetic properties such as, e.g., a nano or micro particles, for example a magnetic particle, which is an example of a 3D substrate. The magnetic particle can comprise a magnetic metal oxide material such as, e.g., $Fe_2O_3$, $Fe_3O_4$, or $MFe_2O_4$ (with M=Co, Mn, and the like) optionally being coated with a stabilising layer. The stabilising layer can, for example, be a layer of $SiO_2$ or a layer of organic polymers. Preferably, the substrate is glass or a substrate comprising a metal oxide.

A can be one of $X_3Si$, $X_2R^1Si$, $XR^1R^2Si$ wherein X can be a halo or alkoxy group, preferably a chloro- or an ethoxy group and wherein $R^1$ and $R^2$ can be one of $CH_3$— or $CH_3$—$CH_2$— or an other alkyl chain, which can optionally be interrupted by heteroatoms. Preferably, A can be $Cl_3Si$— or $EtO_3Si$—.

2) —$(CH_2)_n$ is an alkyl chain, which enables the formation of an ordered self assembled (SAM) monolayer film on a substrate surface as defined hereinabove on the basis of van der Waals interactions between adjacent chains in the self-assembled monolayer film. In this alkyl chain, n is the number of repetitive methylene units and can be any number from 0 to 30. Preferably n is from 6 to 22. Even more preferably, n is from 8 to 18. The described alkyl chain can optionally be interrupted by p heteroatoms, wherein p is such that n+p is from 0 to 30.

Together with the $X_3Si$-functionality, this part of the molecule makes sure a well-defined monolayer is formed when silane molecules with formula (1) are deposited onto a substrate.

3) $-(O[CH_2]_t)_m-$ is an oligo(alkylene glycol) chain wherein t can be from 1 to 10, preferably from 1 to 5. Most preferably, t is 2, in that way forming an oligo (ethylene glycol) chain. This $(O[CH_2]_t)_m$ chain is able to counteract the non-specific adsorption of biological moieties onto the surface. This part of the silane molecule thus provides the protein-resistant function to the silane molecule. In this chain, m is the number of repetitive ethylene glycol and can be any number from 0 to 50. Preferably, m is from 3 to 22. Even more preferably, m is from 3 to 6. For values of m larger than 6, the silane molecules become too large and the layer formed by the silane molecules possibly becomes too thick, hereby loosing optimal functionality of the silane molecule when it is, for example, used as an interface layer in a sensor. For m values lower than 3, the protein-resistant functionality becomes less pronounced.

4) $-(CH_2)_v-$ is a spacer that links the oligo(ethylene glycol) chain with the functional group Y (see further in point 5). The spacer can comprise a branched or linear alkyl chain wherein v is preferably from 0 to 5. In specific cases and for silane molecules comprising particular Y groups such as, e.g., maleimide, this spacer can be absent, i.e., v is zero. The alkyl chain can optionally be interrupted by q heteroatoms, wherein q is preferably such that v+q is from 0 to 5. An example of a spacer can be a spacer with, e.g., v=1 and q=1, i.e., $-O-CH_2-$.

5) Y is a functional group for binding biological moieties onto the silane molecule which can form a monolayer on a substrate. Hence, this part of the silane molecule provides the recognising or pre-activated function to the silane molecule. According to the preferred embodiments, Y is preferably a highly reactive functional moiety compatible with monolayer formation which needs no in situ activation prior to reaction with the biological moiety. Y can, for example, be, but is not limited to, conjugated carbonyls, epoxy, nitriloacetic acid, cyano, hydrazide, aziridine, sulfonylchloride, trifluoromethyldiaziridine, pyridylsulfide, N-acetyl -imidazole, vinylsulfone, arylazide, anhydride, diazoacetate, haloacetyl, benzophenone, isothiocyanate, isocyanate, halogen substituted benzene, pyridyidisulfide, biotin, protected carboxyl, protected amine, protected sulfohydryl, protected maleimide. According to the first aspect, Y is most preferably a conjugated carbonyl. Unlike other carbonyl function such as, e.g., aldehydes ($-CH=O$), conjugated carbonyls are functional groups which are compatible with the silylation step necessary to introduce a silane functionality in the final synthesis step of the silane molecule according to the first aspect (see further). In order to retain the pre-activated coupling properties of the carbonyl it is desired that the silylation occurs selectively on the alkene instead of on the carbonyl in the coupling group. Silylation of a carbonyl however, is more likely to occur compared to the alkene due to the high affinity of Si for O. However, when these carbonyls are conjugated, they are protected against this silylation reaction. Conjugated carbonyls comprise all carbonyls that comprise an electronegative heteroatom (e.g., N or O) adjacent to the carbonyl function or that comprise an α,β-unsaturated function or a combination of both. The adjacent heteroatom can be, but is not restricted to, a part of the spacer. Examples of preferred conjugated carbonyls which can be used according to the preferred embodiments include fluor substituted benzoate (see further, Example 1), pentafluorophenylester (see further, Examples 2 and 3), N-hydroxysuccinimide ester (see further, Example 4), acid halogenide (see further, Example 5) or maleimide (see further, Example 6 and 7).

The biological moieties that can be covalently bound or adsorbed onto the Y group of the silane molecule can, for example, be, but are not limited to, nucleic acid strands (DNA, PNA, RNA), a cell body, proteins, hormones, antibiotics, antibodies, chemically or enzymatically modified antibodies, VHH fragments of lama or camel antibodies, synthetic receptors, single chain Fv's, antigens, enzymes or drugs. In general, these biological moieties will serve as a biological sensing element and will be part of a sensor. The resulting sensor will be suitable for determining the presence of a compound, such as a target molecule, which interacts with the biological sensing element. The target molecule can, for example, be, but is not limited to, complementary nucleic acid strands (DNA, PNA, RNA), proteins, hormones, antibiotics, antibodies, antigens, enzymes, drugs or molecules such as specific molecules present in for example gases and liquids.

An advantage of the silane molecules according to this first embodiment is that they combine a protein-resistant function with a pre-activated or recognising function. In that way, only one molecule has to be provided at a surface of a substrate of, for example, a biosensor or micro-array slide, in order to provide the sensor with a recognising or pre-activated function and a protein-resistant function at the same time. Furthermore, due to the $-(CH_2)_n-$ chains, a well-defined self-assembled monolayer can be obtained when depositing the silane molecule to a substrate (see further). Moreover, because of the flexibility of the alkylene glycol chain, the silane molecule is less rigid and thus causes less steric hindrance during the analyte recognition.

In a second aspect, a method for the synthesis of the molecule is described.

The method according to the second aspect comprises the following steps:

Providing an alcohol with general formula:

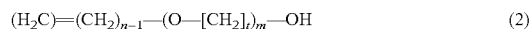

$$(H_2C)=(CH_2)_{n-1}-(O-[CH_2]_t)_m-OH \qquad (2)$$

wherein n can be from 0 to 30, preferably from 6 to 22 and most preferably from 8 to 18, m can be from 0 to 50, preferably from 3 to 22 and most preferably from 3 to 6 and t can be from 1 to 10, preferably from 1 to 5, and most preferably t is 2. The $-(CH_2)_{n-1}-$ chain can optionally comprise p heteroatoms, p being such that n+p is from 0 to 30.

Converting said alcohol to a molecule having a functional group Y and optionally comprising a spacer, hence forming an intermediate with formula:

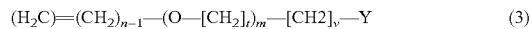

$$(H_2C)=(CH_2)_{n-1}-(O-[CH_2]_t)_m-[CH2]_v-Y \qquad (3)$$

There are two preferred ways to obtain formula (3). A first way is by directly replacing the OH-group by a suitable Y group. Another way is by first converting the OH-group in another reactive end group such as, e.g., a $NH_2-$ group and then replacing the molecule with the other reactive end group to a molecule comprising a Y-group. Both methods can possibly result in the presence of a spacer $-(CH_2)_v-$ between the Y functional group and the alkyleneglycol chain.

Providing said molecule with formula (3) with an A-group, forming the silane molecule with general formula:

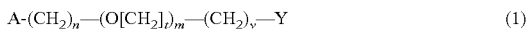

$$A\text{-}(CH_2)_n\text{—}(O[CH_2]_t)_m\text{—}(CH_2)_v\text{—}Y \quad (1)$$

wherein A can be one of $X_3Si$, $X_2R^1Si$, and $XR^1R^2Si$, wherein X can be a halo or alkoxy group, preferably a chloro- or an ethoxy group and wherein $R^1$ and $R^2$ can be one of $CH_3$— or $CH_3$—$CH_2$— or another alkyl chain, which can optionally be interrupted by heteroatoms. Preferably, A is $Cl_3Si$— or $EtO_3Si$—.

Hereinafter, the synthesis will be discussed for some silane molecules with different functional Y groups. It has to be understood that these examples are only for illustration and are not limiting.

The first step of the synthesis, which is identical for all examples, is the synthesis of an alcohol with formula (2). The synthesis route is illustrated in FIG. 1.

For the preparation of the alcohol with formula (2) a halogenated alkene is reacted with an ethylene glycol. The value for n chosen in the halogenated alkene will determine the length of the —$(CH_2)_n$— alkyl chain in the final silane molecule (see formula (1)) while the value for m chosen in the ethylene glycol will determine the length of the oligo (ethylene glycol) chain in the final silane molecule (see formula (1)). Hereinafter, a specific example in which n=11 and m=6, i.e., 2-[2-(2-{2-[2-(2-undec-10-enyloxy-ethoxy)-ethoxy]-ethoxy}-ethoxy)-ethoxy]-ethanol will be described. In the following examples, this alcohol with formula (2) and with n=11 and m=6 will be used in all examples described hereinafter for the synthesis for specific silane molecules. It has, however, to be understood, that this is not limiting and that other alcohols with a structure as formula (2) also can be used for the synthesis of silane molecules according to the preferred embodiments.

Figure 2:
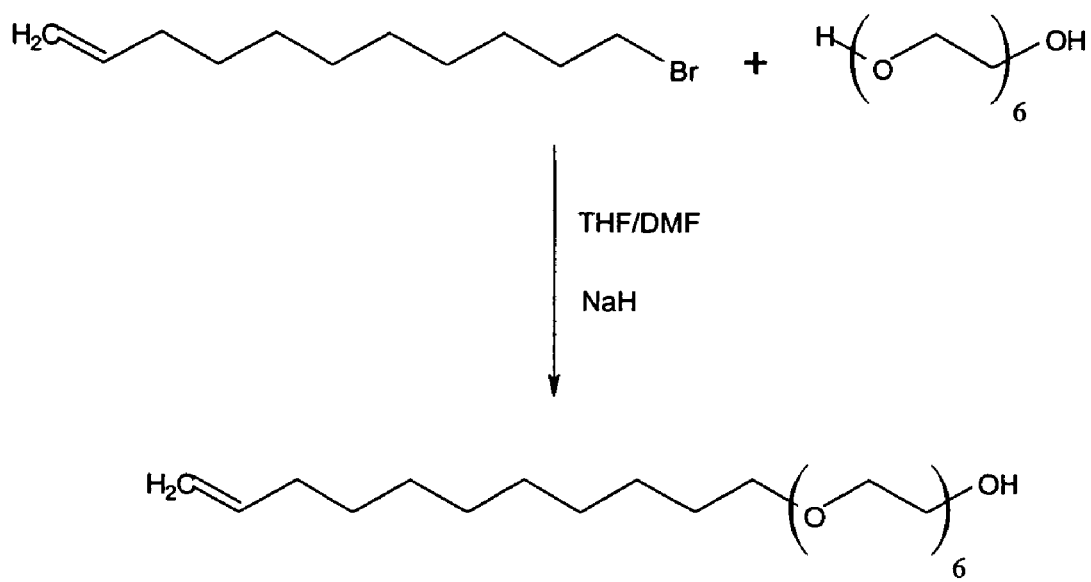
FIG. 2 illustrates the synthesis of 2-[2-(2-{2-[2-(2-undec-10-enyloxy)-ethoxy]-ethoxy}-ethoxy)-ethoxy]-ethanol.

Synthesis of 2-[2-(2-{2-[2-(2-undec-10-enyloxy-ethoxy)-ethoxy]-ethoxy}-ethoxy) -ethoxy]-ethanol (n=11 and m=6) (see FIG. 2).

Method

In a dry three neck bottle comprising a magnetic stirrer and under argon atmosphere, 75 g (265.5 mmol) hexa-ethyleneglycol and 6.35 g NaH (159 mmol) (60% in oil) are dissolved in 400 ml Tetrahydrofuran (THF) and 240 ml dimethylformamide (DMF). The solution is stirred for 50 minutes. After this, 30.96 g (28.9 ml) (132.9 mmol) 11-broom-1-undecene is added and the resulting solution is stirred for 3 days.

Then, the reaction is quenched with methanol (>100 ml).

The methanol is then removed from the solution, a mixture of THF and DMF is added and the reaction mixture is concentrated by rotary evaporation.

The solution is then dissolved in 200 ml ethyl acetate and 300 ml $H_2O$. The organic phase is extracted and washed with ethyl acetate.

The organic phase (=ethyl acetate) is then dried with $MgSO_4$ and the product is concentrated by rotary evaporation.

The final product is then purified a first time on a silica column using:
1) Petroleum ether/ethanol (100/5)
2) Diethylether/ethanol (100/15)

The final product is purified a second time on a silica column using:
Diethylether/ethanol (100/15)

The purified product is concentrated by rotary evaporation and will be in the further description referred to as molecule A.

Figure 29:
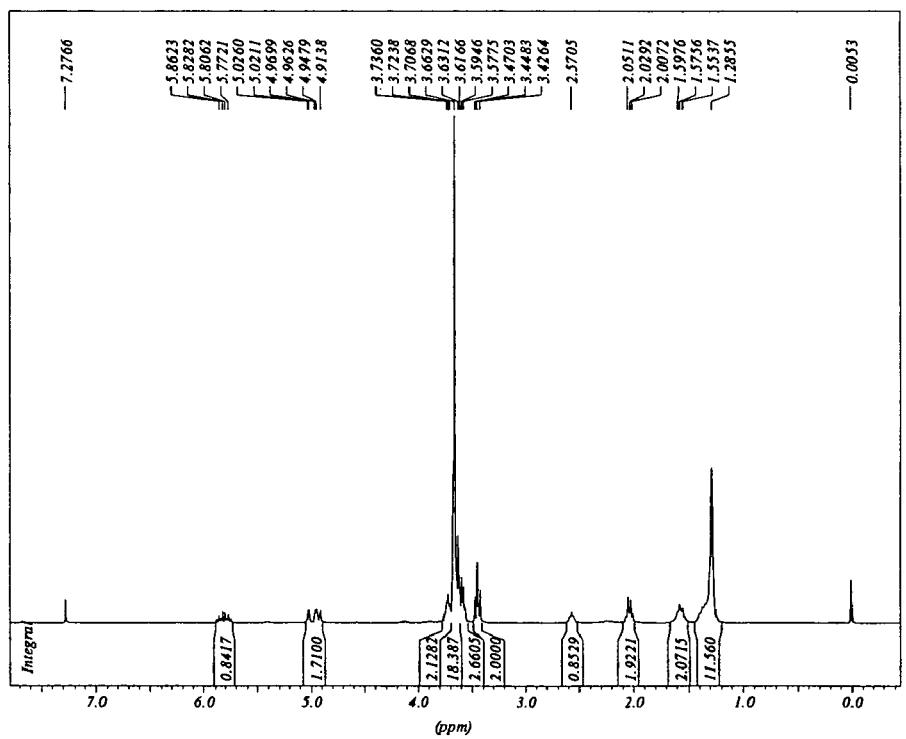
FIG. 29 illustrates the $^1$H NMR spectrum of 2-[2-(2-{2-[2-(2-undec-10-enyloxy-ethoxy)-ethoxy]-ethoxy}-ethoxy)-ethoxy]-ethanol synthesised via the method described in FIG. 2.

In FIG. 29 the $^1H$ NMR spectrum of 2-[2-(2-{2-[2-(2-undec-10-enyloxy -ethoxy)-ethoxy]-ethoxy}-ethoxy)-ethoxy]-ethanol synthesised via the method described above is illustrated.

For preparing other alcohols with a structure according to general formula (2) and with m=3, 4 or 5, the same procedure can be followed using respectively triethyleneglycol, tetraethyleneglycol or pentaethyleneglycol as a reagent.

Hereinafter, some examples of synthesis routes for preparing a silane molecule with ethylene glycol spacers and conjugated carbonyls as functional end groups, according to the first aspect.

EXAMPLE 1

Figure 3:
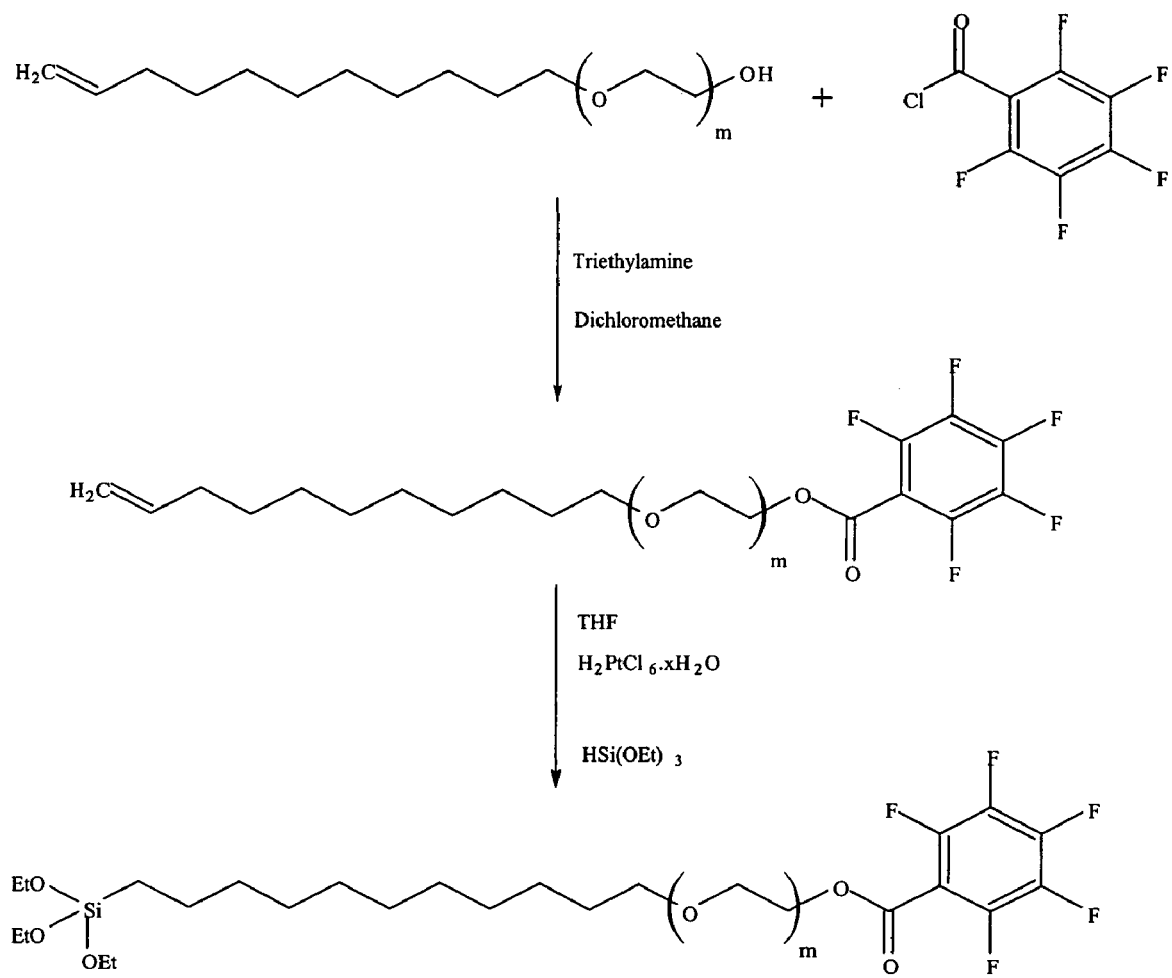
FIG. 3 illustrates the synthesis of a silane molecule with pentafluor-benzoate as activated functionality.

Synthesis of triethoxy-(11-{2-[2-(2-{2-[2-(2-ethoxy)-ethoxy]-ethoxy}-ethoxy)-ethoxy]-ethoxy}-2,3,4,5,6-pentafluorbenzoate)-silane The silane according to the first example has a general formula as in formula (1) with $X=OEt_3$ and with Y=a fluor substituted benzoate, more particular 2,3,4,5,6 pentafluor-benzoate. The synthesis route for the silane of Example 1 is illustrated in FIG. 3. The synthesis route will be described starting from molecule A and with thus m=6 and n=11. It has to be understood that similar molecules can also be obtained starting from molecule A (see formula 2) having another value for m or n.

Method

Step 1

In a dry two neck bottle which comprises a magnetic stirrer and under argon atmosphere, 1 equivalent of molecule A (m=6) is dissolved in $CH_2Cl_2$.

~1-5 equivalents of triethylamine ($Et_3NH_2$) are then added and the solution is stirred for 20 minutes.

2 equivalents of pentafluorbenzoylchloride (CAS: 2251-50-5) are added and the solution is stirred overnight.

The $CH_2Cl_2$ and $Et_3NH_2$ are removed at the rotavapor. Hereby it is important to avoid extraction in order to prevent hydrolysis of the pentafluorbenzoate.

The product is then purified on a silica column using diethylether/ethanol (100/5).

The purified product is concentrated using rotary evaporation.

Figure 30:
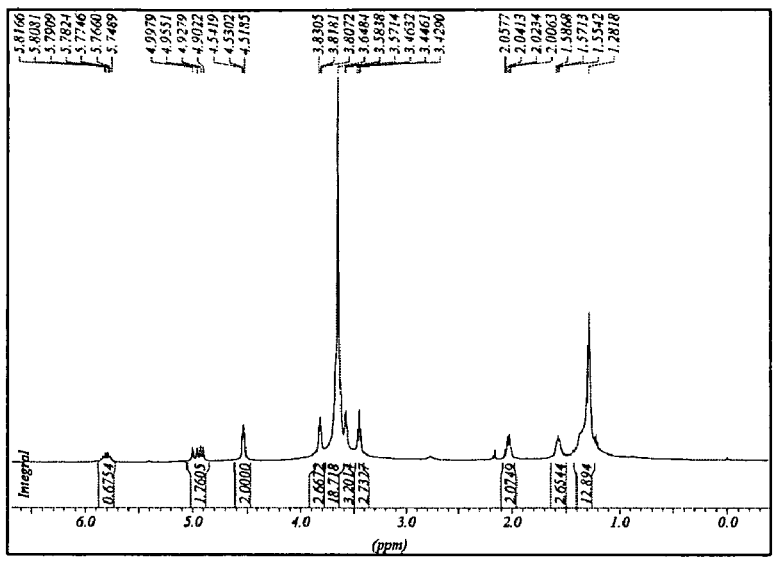
FIGS. 30 and 31 respectively illustrate the $^1$H NMR and $^{13}$C NMR spectrum of the intermediate product formed in the first step of the synthesis of triethoxy-(11-{2-[2-(2-{2-[2-(2-ethoxy)-ethoxy]-ethoxy}-ethoxy)-ethoxy]ethoxy}-2,3,4,5,6-pentafluorbenzoate)-silane.
Figure 31:
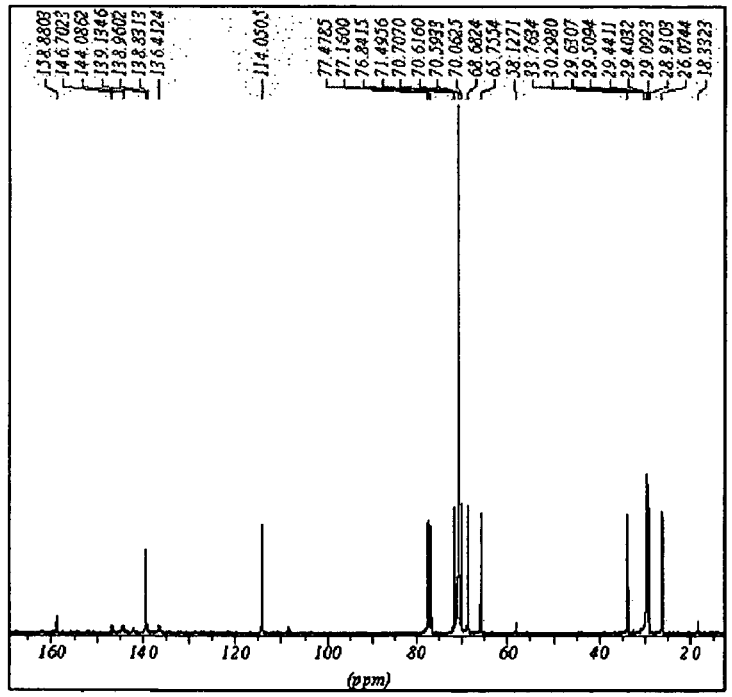

$^1H$ NMR (see FIG. 30)
5.79 and 4.94=hydrogens of =CH and =$CH_2$
~3.69=hydrogens of ($OCH_2$ $_{CH2}$)
3.45 (triplet)=H of $CH_2$'s next to $OCH_2CH_2$
1.2-2.1=hydrogens of other $CH_2$'s
3.8 and 4.5 $CH_2$'s close to pentafluorbenzoate
$^{13}C$ NMR (see FIG. 31)
158.7=C=O in pentafluorbenzoate
146.5 and 144.3 and 143.9 and 141.7 and 138.8 and 136.2=C—F in pentafluorbenzoate
108.21=C next to C=O in pentafluorbenzoate
113.9=carbon in C=C
~70=$sp^3$ carbons of $OCH_2CH_2$
~30=carbons of other $CH_2$'s Step 2

In a dry ampoule, 1 equivalent of the product obtained in step 1, i.e., (2-[2-(2-{2-[2-(2-undec-10-enyloxyethoxy)-ethoxy]-ethoxy}-ethoxy)-ethoxy]-ethoxy)-2,3, 4,5,6-penta-fluorbenzoate is dissolved in dry toluene Then all the water is eliminated by rotary evaporation at reduced pressure. This step is repeated twice.

A trace of $H_2PtCl_6 \cdot xH_2O$ (~0.0012 g per 0.5 g of alkene) is then added.

Next, dry toluene is added and all the water is eliminated by rotary evaporation at reduced pressure and increased temperature A magnetic stirrer is added and the dry ampoule is immediately closed with a septum, the ampoule is kept under argon.

Then 1.2 equivalents of $HSiOEt_3$ are added and the solution is stirred for 30 minutes at 90° C.

The final product is purified by dissolution in toluene followed by rotary evaporation at reduced pressure.

For the preparation of the trichlorosilane variant, i.e., wherein A in formula (1) is $Cl_3Si$ instead of $OEt_3Si$, the same procedure as described above can be followed wherein $HSiCl_3$ is used as a reagent instead of $HSiOEt_3$.

Figure 32:
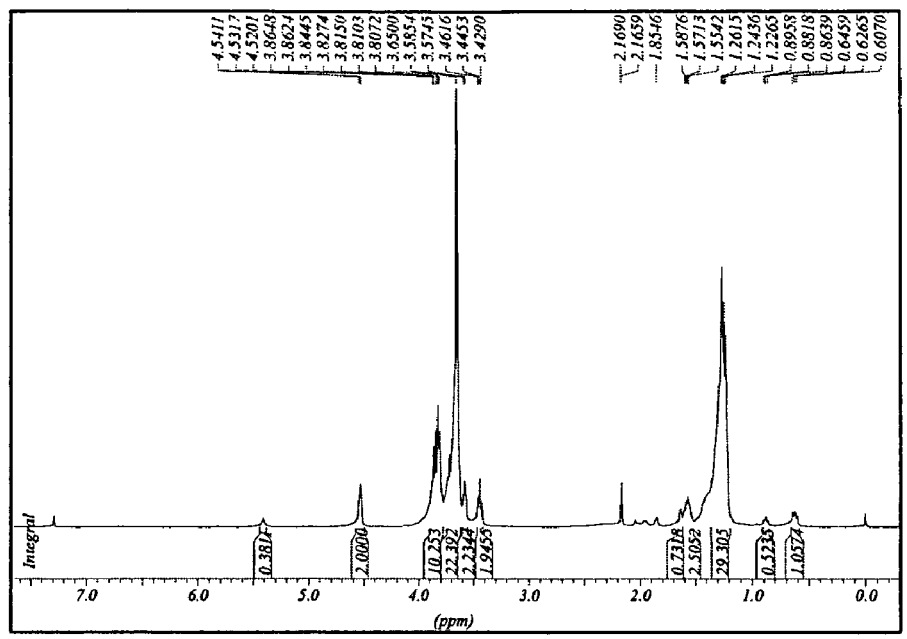
FIGS. 32 and 33 respectively illustrate the $^1$H NMR and $^{13}$C NMR spectrum of triethoxy-(11-{2-[2-(2-{2-[2-(2-ethoxy)-ethoxy]-ethoxy}-ethoxy)-ethoxy]ethoxy}-2,3,4,5,6-pentafluorbenzoate)-silane.
Figure 33:
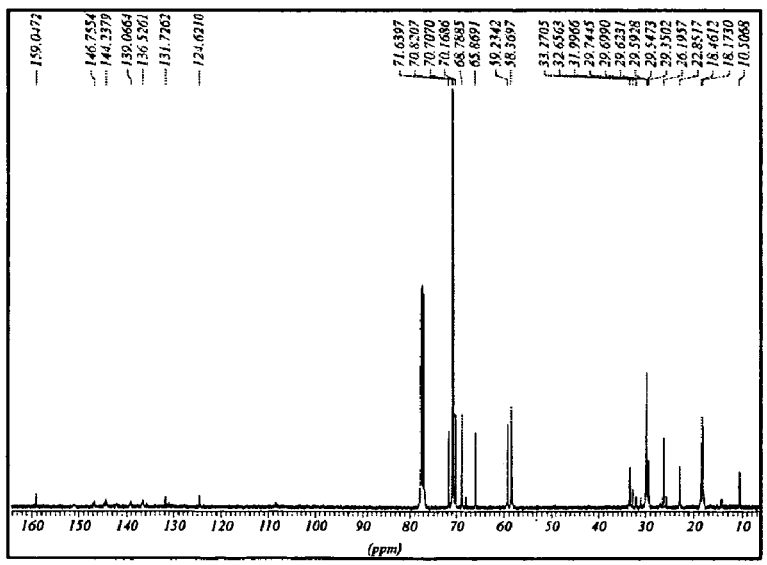

$^1H$ NMR (see FIG. 32)
no more peaks for C=C
~3.74=hydrogens of $(OCH_2CH_2)$
3.84=hydrogens of $(OCH_{2\ CH2})$
3.49 (triplet)=H of $CH_2$'s next to $OCH_2CH_2$
1.2-2.1=hydrogens of other $CH_2$'s
3.8 and 4.5 $CH_2$'s close to pentafluorbenzoate
3.8 $CH_2$'s in ethoxysilane function $^{13}C$ NMR (see FIG. 33)
158.7=C=O in pentafluorbenzoate
146.5 and 144.3 and 143.9 and 141.7 and 138.8 and 136.2=C—F in pentafluorbenzoate
108.21=C next to C=O in pentafluorbenzoate
no more peaks for C=C
~70=$sp^3$ carbons of $OCH_2CH_2$
~30=carbons of other $CH_2$'s
22-26=$sp^3$ carbons next to $Si(OEt)_3$ Based on the $^{13}C$ NMR and $^1H$ NMR spectrum it can be concluded that the silylation occurs selectively on the alkene with respect to the carbonyl function. The reason for this is the lower reactivity of the carbonyl due to the presence of the electronegative heteroatom (O) adjacent to the carbonyl function or the presence of the $\alpha,\beta$ unsaturated function or a combination of both. These types of carbonyl functions are called conjugated carbonyls. The presence of a spacer between the PEG-function and the carbonyl containing Y-function does not influence the selective silylation reaction. Due to the selective silylation of the alkene it is has been shown that PEG-modified silanes with coupling groups containing conjugated carbonyls and possibly a spacer in between can be synthesised via the procedure described above. Synthesis routes for other conjugated carbonyls coupling groups are described in the following examples (Example 2-7) and also rely on this procedure.

EXAMPLE 2

Figure 4:
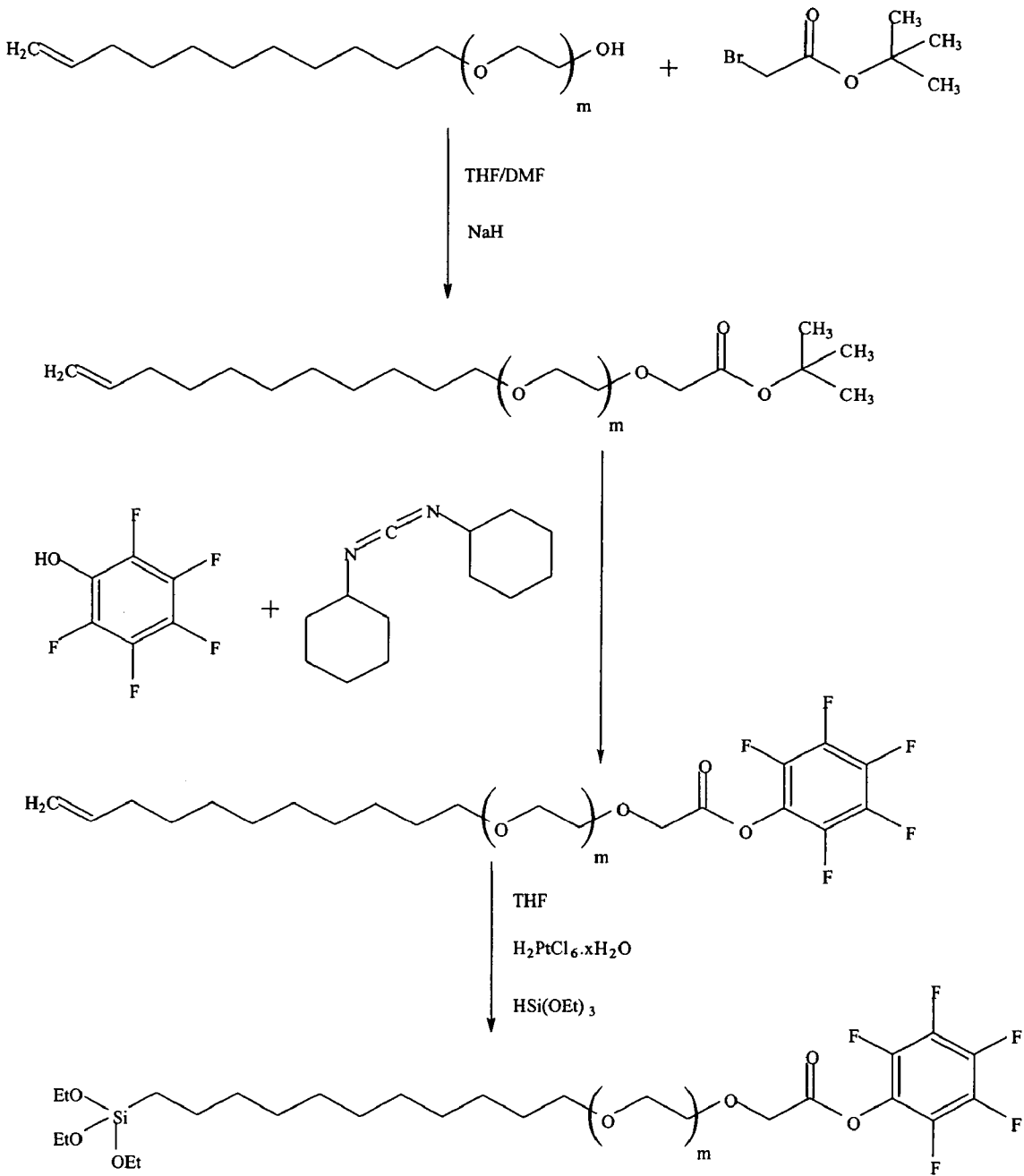
FIG. 4 illustrates the synthesis of a silane molecule with pentafluor-phenylacetate as activated functionality.

Synthesis of Triethoxy-(11-{2-[2-(2-{2-[2-(2-ethoxy)-ethoxy]-ethoxy}-ethoxy)-ethoxy]-ethoxy}-perfluorophenyl acetate)-silane The silane according to the second example has a general formula as in formula (1) with X=$OEt_3$ and with Y=a pentafluorphenyl ester. The synthesis route for the silane of Example 2 is illustrated in FIG. 4. The synthesis route will be described starting from molecule A and thus with m=6 and n=11. It has to be understood that similar molecules can also be obtained starting from molecule A having another value for m and n.

Method

Step 1

In a dry three neck bottle comprising a magnetic stirrer and being under argon atmosphere, 1 equivalent of molecule (m=6) is, together with a small excess of NaH, dissolved in DMF/THF.

The solution is stirred for 50 minutes.

~1.2 equivalents of tert-butyl bromoacetate (CAS: 5469-26-1) is added dropwise and the solution is stirred overnight at room temperature.

THF and DMF are then removed at the rotavap.

The solution is then extracted with ethyl acetate and $H_2O$.

The reaction mixture is then concentrated using rotary evaporation.

Next, the product is purified on a silica column using a suitable mixture of organic solvents, known by persons skilled in the art.

The purified product is again concentrated using rotary evaporation

Step 2

In a dry three neck bottle comprising a magnetic stirrer and being under argon atmosphere, 1 equivalent of the product obtained in step 1, i.e., 2-[2-(2-{2-[2-(2-undec-10-enyloxy-ethoxy)-ethoxy]-ethoxy}-ethoxy)-ethoxy]-ethoxy)-tert-butyl acetate together with ~1.2 equivalents of dicylcohexyl-carbodiimide (DCC) (CAS: 538-75-0) is stirred for 12 hours.

Then, ~1.2 equivalents of pentafluorphenol (PFP) (CAS: 771-61-9) are added and the solution is stirred at room temperature.

The solution is then extracted with organic solvents (!!! avoid extraction with $H_2O$!!!).

The product is purified on a silica column using a suitable mixture of organic solvents, known by persons skilled in the art.

The purified product is then purified using rotary evaporation.

Step 3

In a dry ampoule, 1 equivalent of the product obtained in step 2, i.e., 2-[2-(2-{2-[2-(2-undec-10-enyloxy-ethoxy)-ethoxy]-ethoxy}-ethoxy)-ethoxy]-ethoxy -perfluorophenyl acetate (m=6) is dissolved in dry toluene.

All water is eliminated by means of rotary evaporation at reduced pressure. This step is repeated twice.

A trace of $H_2PtCl_6 \cdot xH_2O$ (~0.0012 g per 0.5 g of alkene) is then added.

After adding dry toluene, all water is eliminated by means of rotary evaporation at reduced pressure and increased temperature.

A magnetic stirrer is added and the ampoule is immediately closed with a septum while it is kept under argon atmosphere.

b 1.2 equivalents of $HSiOEt_3$ are then added and the reaction mixture is stirred for 30 minutes at 90° C.

The product is purified by dissolution in toluene followed by rotary evaporation at reduced pressure.

For the preparation of the trichlorosilane variant, i.e., wherein A in formula (1) is $Cl_3Si$ instead of $OEt_3Si$, the same procedure as described above can be followed wherein $HSiCl_3$ is used as a reagent instead of $HSiOEt_3$.

EXAMPLE 3

Figure 5:
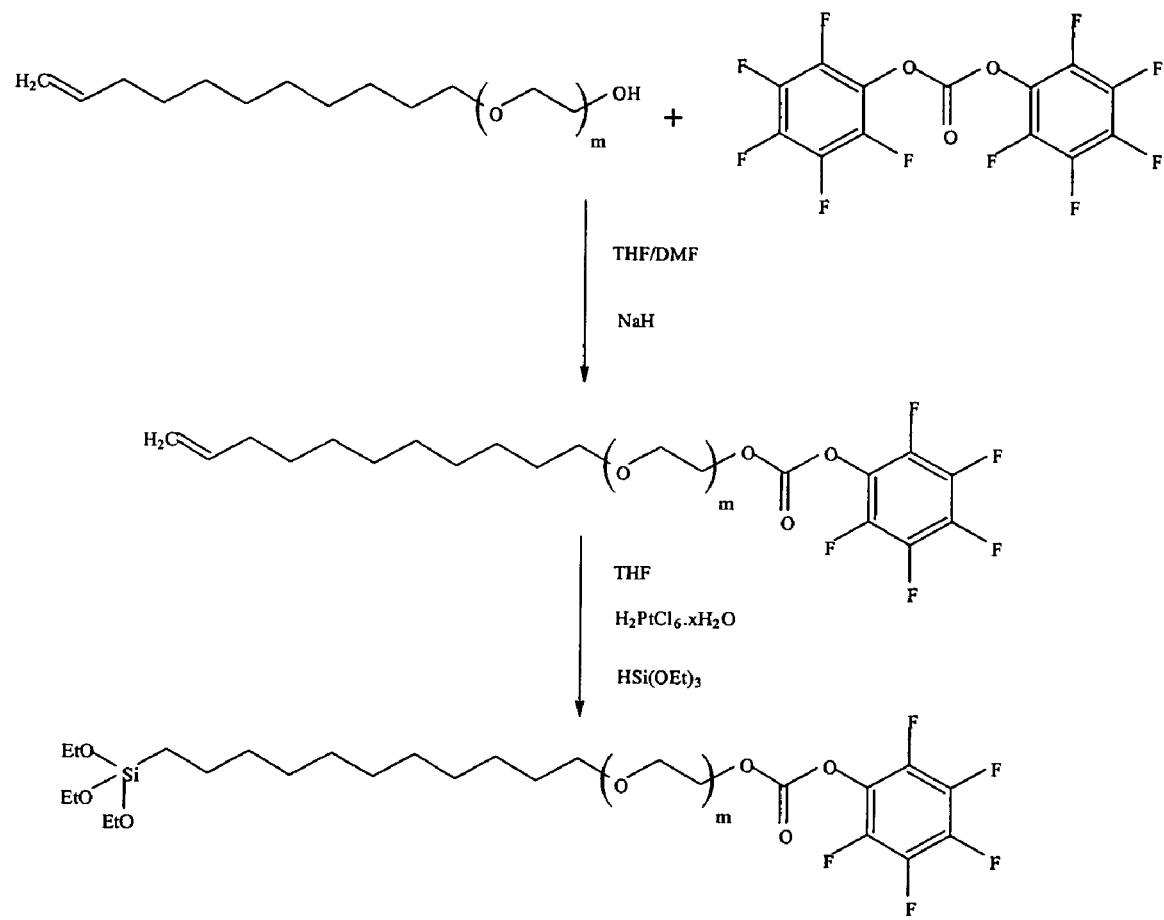
FIG. 5 illustrates the synthesis of a silane molecule with pentafluor-phenylacetate as activated functionality.

Synthesis of Triethoxy-(11-{2-[2-(2-{2-[2-(2-ethoxy)-ethoxy]-ethoxy}-ethoxy)-ethoxy]-ethoxy}-perfluorophenyl acetate)-silane The silane according to the third example has a general formula as in formula (1) with X=$OEt_3$ and with Y=a pentafluorphenyl ester. The difference with Example 2 is that now the spacer is a single heteroatom. The synthesis route for the silane of Example 3 is illustrated in FIG. 5. The synthesis route will be described starting from molecule A and thus with m=6 and n=11. It has to be understood that similar molecules can also be obtained starting from molecule A having another value for m and n.

Method

Step 1

In a dry three neck bottle comprising a magnetic stirrer and being under argon atmosphere, 1 equivalent of molecule A (m=6) is dissolved in DMF/THF and the solution is stirred for 50 minutes.

~1.2 equivalents of pentafluorphenylcarbonate (Molecular biosciences 60008) are added dropwise and the reaction mixture is stirred overnight at room temperature.

THF and DMF are removed at the rotavapor.

The reaction mixture is then extracted with organic solvents (!!! avoid extraction with $H_2O$!!!).

The reaction mixture is concentrated using rotary evaporation.

The product is then purified on a silica column using a suitable mixture of organic solvents, known by persons skilled in the art.

The purified product is purified using rotary evaporation.

Step 2

In a dry ampoule, 1 equivalent of the product obtained in step 1, i.e., 2-[2-(2-{2-[2-(2-undec-10-enyloxy-ethoxy)-ethoxy]-ethoxy}-ethoxy)-ethoxy]-ethoxy -perfluorophenyl acetate (m=6) is dissolved in dry toluene.

All water is eliminated by means of rotary evaporation at reduced pressure. This step is repeated twice.

A trace of $H_2PtCl_6.xH_2O$ (~0.0012 g per 0.5 g of alkene) together with dry toluene is added and all water is eliminated by means of rotary evaporation at reduced pressure and increased temperature.

A magnetic stirrer is added and the ampoule is immediately closed with a septum while it is being kept under argon atmosphere.

1.2 equivalents of $HSiOEt_3$ are then added and the reaction mixture is stirred for 30 minutes at 90° C.

The product is then purified by dissolution in toluene followed by rotary evaporation at reduced pressure.

For the preparation of the trichlorosilane variant, i.e., wherein A in formula (1) is $Cl_3Si$ instead of $OEt_3Si$, the same procedure as described above can be followed wherein $HSiCl_3$ is used as a reagent instead of $HSiOEt_3$.

EXAMPLE 4

Figure 6:
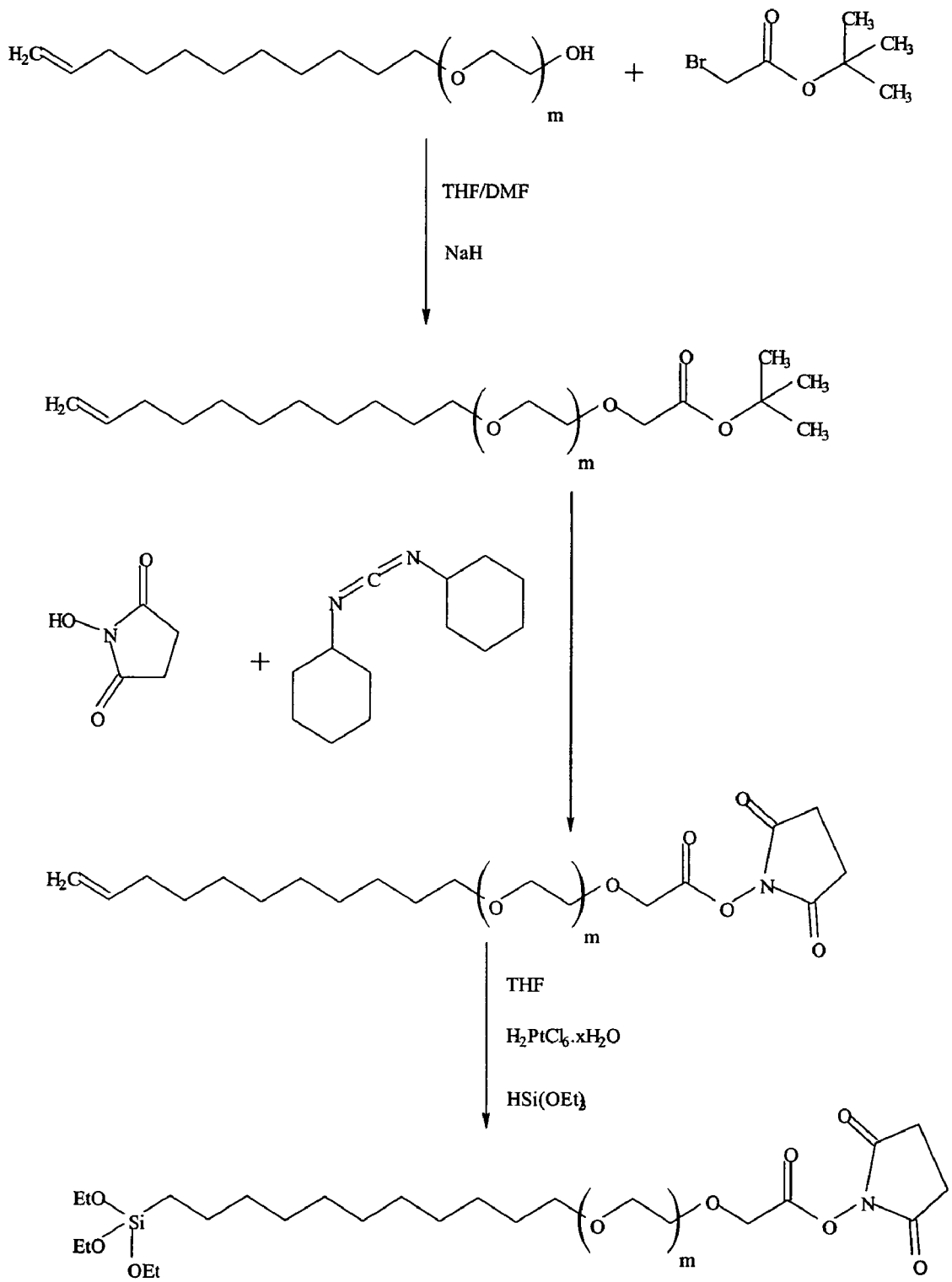
FIG. 6 illustrates the synthesis of a silane molecule with a hydroxy-succinimide ester as activated functionality.

Synthesis of Triethoxy-(11-{2-[2-(2-{2-[2-(2-ethoxy)-ethoxy]-ethoxy}-ethoxy)-ethoxy]-ethoxy}-N-hydroxysuccinimide ester)-silane The silane according to the fourth example has a general formula as in formula (1) with X=$OEt_3$ and with Y=a hydroxy succinimide ester. The synthesis route for the silane of Example 4 is illustrated in FIG. 6. The synthesis route will be described starting from molecule A and thus with m=6 and n=11. It has to be understood that similar molecules can also be obtained starting from molecule A having another value for m and n.

Method

Step 1

In a dry three neck bottle comprising a magnetic stirrer and being under argon atmosphere, 1 equivalent of molecule A (m=6) is, together with a small excess of NaH, dissolved in DMF/THF and the solution is stirred for 50 minutes.

~1.2 equivalents of tert-butyl bromoacetate (CAS: 5469-26-1) are added dropwise and the solution is stirred overnight at room temperature.

THF and DMF are at the rotavap.

Then, extraction is performed with ethyl acetate and $H_2O$.

The reaction mixture is concentrated using rotary evaporation.

The resulting product is purified on a silica column using a suitable mixture of organic solvents, known by persons skilled in the art.

The purified product is then purified using rotary evaporation.

Step 2

In a dry three neck bottle comprising a magnetic stirrer and being under argon atmosphere, 1 equivalent of the product obtained in step 1, i.e., 2-[2-(2-{2-[2-(2-undec 10-enyloxy-ethoxy)-ethoxy]-ethoxy}-ethoxy)-ethoxy]-ethoxy)-tert-butyl acetate, is mixed with ~1.2 equivalents of dicylcohexyl-carbodiimide (DCC) (CAS: 538-75-0) and is stirred for 12 hours.

~1.2 equivalents of N-hydroxysuccinimide (NHS) (CAS: 771-61-9) are added and the solution is stirred at room temperature.

Extraction is then performed with suitable organic solvents, known by persons skilled in the art (!!! avoid extraction with $H_2O$!!!).

The resulting product is purified on a silica column using a suitable mixture of organic solvents, known by persons skilled in the art.

The purified product is then concentrated using rotary evaporation.

Step 3

In a dry ampoule, 1 equivalent of the product obtained in step 2, i.e., 2-[2-(2-{2-[2-(2-undec-10-enyloxy-ethoxy)-ethoxy]-ethoxy}-ethoxy)-ethoxy]-ethoxy-N-hydroxy succinimide ester (m=6), is dissolved in dry toluene.

All water is eliminated by means of rotary evaporation at reduced pressure. This step is repeated twice.

A trace of $H_2PtCl_6 \cdot xH_2O$ (~0.0012 g per 0.5 g of alkene) is added together with dry toluene and all water is eliminated by means of rotary evaporation at reduced pressure and increased temperature.

A magnetic stirrer is added and the ampoule is immediately closed with a septum while being kept under argon atmosphere.

1.2 equivalents of $HSiOEt_3$ are added and the reaction mixture is stirred for 30 minutes at 90° C.

The resulting product is the purified by dissolution in toluene followed by rotary evaporation at reduced pressure.

For the preparation of the trichlorosilane variant, i.e., wherein A in formula (1) is $Cl_3Si$ instead of $OEt_3Si$, the same procedure as described above can be followed wherein $HSiCl_3$ is used as a reagent instead of $HSiOEt_3$.

EXAMPLE 5

Figure 7:
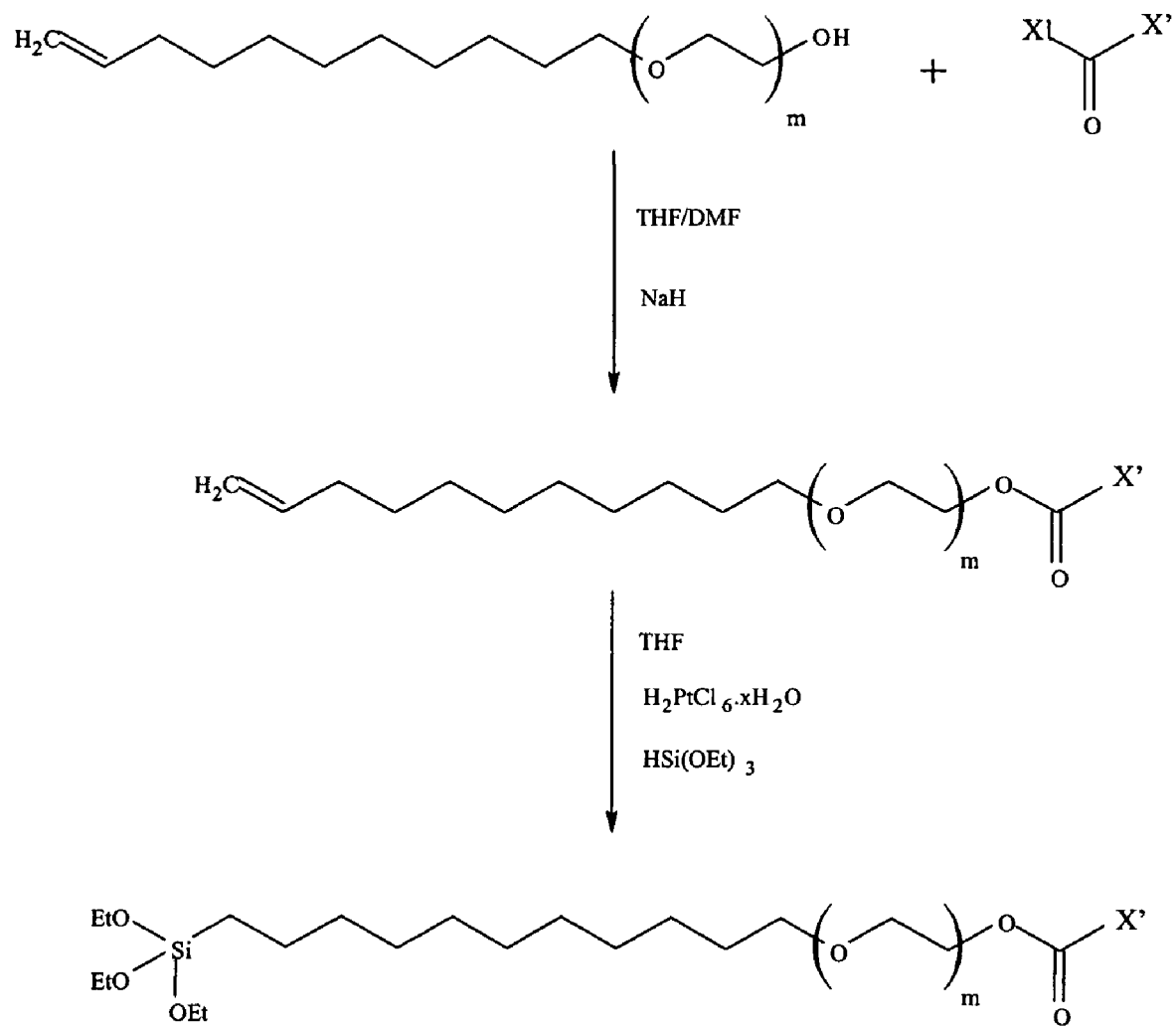
FIG. 7 illustrates the synthesis of a silane molecule with carbono-chloridate as activated functionality.

Synthesis of Triethoxy-(11-{2-[2-(2-{2-[2-(2-ethoxy)-ethoxy]-ethoxy}-ethoxy)-ethoxy]-ethoxy}-carbonochloridate)-silane The silane according to the fifth example has a general formula as in formula (1) with $X=OEt_3$ and with Y=an acid halogenide. The synthesis route for the silane of Example 5 is illustrated in FIG. 7. In this figure, X' is a halogen atom and can, for example, be Cl, Br, I or F. The synthesis route will be described starting from molecule A and thus with m=6 and for X' being Cl. It has to be understood that similar molecules can also be obtained starting from molecule A having another value for m and/or with other halogen atoms.

Method

Step 1

In a dry three neck bottle comprising a magnetic stirrer and being under argon atmosphere, 1 equivalent of molecule A is, together with a small excess of NaH, dissolved in DMF/THF and the solution is stirred for 50 minutes.

2 equivalents of carbonyldichloride (CAS: 74-44-5) are added and the solution is further stirred for 36 hours.

Next, extraction is performed with suitable organic solvents (!!! avoid if possible the extraction with $H_2O$!!!), known by persons skilled in the art.

The organic phase is dried with $MgSO_4$ and the product is concentrated using rotary evaporation.

The product is then purified on a silica column using a suitable mixture of organic solvents, known by persons skilled in the art.

The purified product is then purified using rotary evaporation.

Step 2

In a dry ampoule, 1 equivalent of the product obtained in step 1, i.e., 2-[2-(2-{2-[2-(2-undec-10-enyloxy-ethoxy)-ethoxy]-ethoxy}-ethoxy)-ethoxy]-ethoxy-carbonochloridate (m=6), is dissolved in dry toluene.

All water is eliminated by means of rotary evaporation at reduced pressure. This step is repeated twice.

A trace of $H_2PtCl_6 \cdot xH_2O$ (~0.0012 g per 0.5 g of alkene) is, together with dry toluene, added and all water is eliminated by means of rotary evaporation at reduced pressure and increased temperature.

A magnetic stirrer is then added and the ampoule is immediately closed with a septum while being kept under argon.

Next, 1.2 equivalents of $HSiOEt_3$ are added and the reaction mixture is stirred for 30 minutes at 90° C.

The product is then purified by dissolution in toluene followed by rotary evaporation at reduced pressure.

For the preparation of the trichlorosilane variant, i.e., wherein A in formula (1) is $Cl_3Si$ instead of $OEt_3Si$, the same procedure as described above can be followed wherein $HSiCl_3$ is used as a reagent instead of $HSiOEt_3$.

EXAMPLE 6

Figure 8:
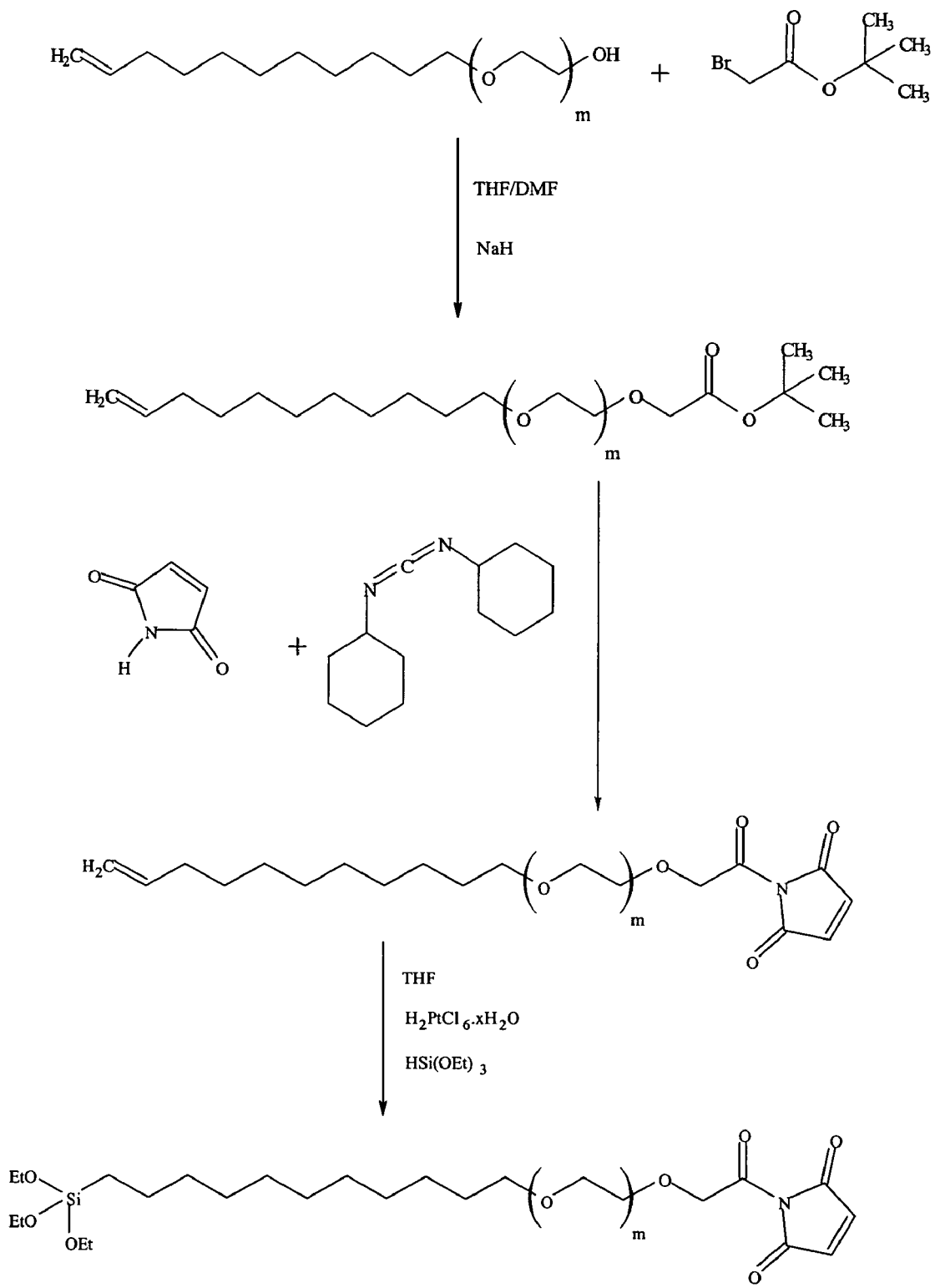
FIG. 8 illustrates the synthesis of a silane molecule with a maleimide ester as activated functionality.

Synthesis of Triethoxy-(11-{2-[2-(2-{2-[2-(2-ethoxy)-ethoxy]-ethoxy}-ethoxy)-ethoxy]-ethoxy}-maleimide ester)-silane The silane according to the sixth example has a general formula as in formula (1) with $X=OEt_3$ and with Y=maleimide. The synthesis route for the silane of Example 6 is illustrated in FIG. 8. The synthesis route will be described starting from molecule A and thus with m=6 and n=11. It has to be understood that similar molecules can also be obtained starting from molecule A having another value for m and n.

Method:

Step 1

In a dry three neck bottle comprising a magnetic stirrer and being under argon atmosphere, 1 equivalent of molecule A is, together with a small excess of NaH, dissolved in DMF/THF and the solution is stirred for 50 minutes.

~1.2 equivalents of tert-butyl bromoacetate (CAS: 5469-26-1) are added dropwise and the solution is further stirred overnight at room temperature.

THF and DMF are removed at the rotavap.

Extraction is then performed with ethyl acetate and $H_2O$.

The reaction mixture is concentrated using rotary evaporation.

The resulting product is purified on a silica column using a suitable mixture of organic solvents, known by persons skilled in the art.

The purified product is then concentrated using rotary evaporation.

Step 2

In a dry three neck bottle comprising a magnetic stirrer and being under argon atmosphere, 1 equivalent of the product obtained in step 1, i.e., 2-[2-(2-{2-[2 -(2-undec-10-enyloxy-ethoxy)-ethoxy]-ethoxy}-ethoxy)-ethoxy]-ethoxy)-tert-butyl acetate, is mixed with ~1.2 equivalents of dicylcohexyl-carbodiimide (DCC) (CAS: 538-75-0) and is stirred for 12 hours.

~1.2 equivalents of maleimide (CAS: 541-59-3) are added and the solution is stirred at room temperature.

Extraction is then performed with organic solvents (!!! avoid extraction with $H_2O$!!!), known by persons skilled in the art.

The resulting product is purified on a silica column using a suitable mixture of organic solvents, known by persons skilled in the art.

The purified product is concentrated using rotary evaporation.

Step 3

In a dry ampoule, 1 equivalent of the product obtained in step 2, i.e., 2-[2-(2-{2-[2-(2-undec-10-enyloxy-ethoxy)-ethoxy]-ethoxy}-ethoxy)-ethoxy]-ethoxy-maleimide ester (if n=6), is dissolved in dry toluene.

All water is eliminated by means of rotary evaporation at reduced pressure. This step is repeated twice.

A trace of $H_2PtCl_6 \cdot xH_2O$ (~0.0012 g per 0.5 g of alkene) together with dry toluene is added and all water is eliminated by means of rotary evaporation at reduced pressure and increased temperature.

A magnetic stirrer is added and the ampoule is immediately closed with a septum while being kept under argon atmosphere.

1.2 equivalents of $HSiOEt_3$ is added and the reaction mixture is stirred for 30 minutes at 90° C.

The resulting product is then purified by dissolution in toluene followed by rotary evaporation at reduced pressure.

For the preparation of the trichlorosilane variant, i.e., wherein A in formula (1) is $Cl_3Si$ instead of $OEt_3Si$, the same procedure as described above can be followed wherein $HSiCl_3$ is used as a reagent instead of $HSiOEt_3$.

EXAMPLE 7

Figure 9:
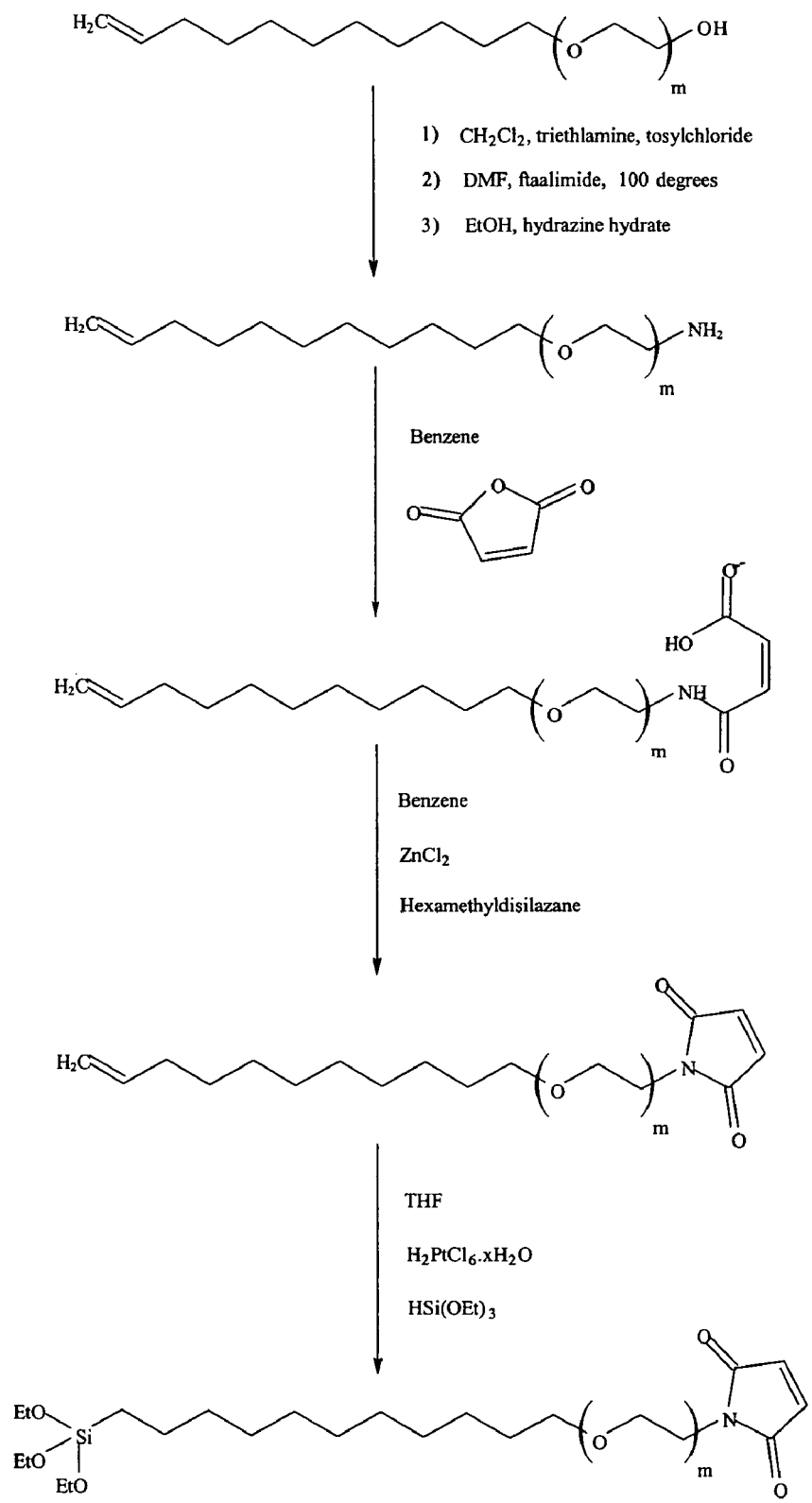
FIG. 9 illustrates the synthesis of a silane molecule with maleimide as activated functionality.

Synthesis of Triethoxy-(11-{2-[2-(2-{2-[2-(2-ethoxy)-ethoxy]-ethoxy}-ethoxy)-ethoxy]-ethoxy}-maleimide)-silane The silane according to the seventh example has a general formula as in formula (1) with X=$OEt_3$ and with Y=maleimide. The synthesis route for the silane of Example 7 is illustrated in FIG. 9. The difference with Example 6 is that now a spacer is absent. The synthesis route will be described starting from molecule A and thus with m=6 and n=11. It has to be understood that similar molecules can also be obtained starting from molecule A having another value for m and n.

Method

Step 1

In a dry three neck bottle comprising a magnetic stirrer and being under argon atmosphere, 1 equivalent of molecule A (m=6) is dissolved in $CH_2Cl_2$.

1.1 equivalents of tosylchloride are added.

1.5 equivalents of triethylamine are added and the reaction mixture is stirred for 1 hour.

$CH_2CL_2$ is removed at the rotavap.

The resulting product is purified on a silica column using a suitable mixture of organic solvents, known by persons skilled in the art.

DMF is added at 100° C.

1.5 equivalents of phthalimide (potassium salt) are added.

DMF is removed at a rotavap and extraction is performed with an organic solvent and $H_2O$.

The resulting product is then purified on a silica column using a suitable mixture of organic solvents, known by persons skilled in the art.

EtOH is added at 60° C.

2 equivalents of hydrazine hydrate are added.

The reaction mixture is concentrated using rotary evaporation.

The resulting product is purified on a silica column using a suitable mixture of organic solvents, known by persons skilled in the art.

Step 2

In a dry three neck bottle comprising a magnetic stirrer and being under argon atmosphere, 1 equivalent of the product obtained in step 1, i.e., 2-[2-(2-{2-[2-(2-undec-10-enyloxy-ethoxy)-ethoxy]-ethoxy}-ethoxy)-ethoxy]-amino ethane, is dissolved in benzene.

The above solution is then dropwise added to a solution of 1 equivalent maleic anhydride in benzene and the reaction mixture is additionally stirred for 2 hours.

Step 3

1 equivalent of $ZnCl_2$ is added to the product obtained in step 2 and the reaction mixture is stirred for 30 minutes.

1.5 equivalents of hexamethyldisilazane (HDMS) dissolved in benzene are dropwise added and the reaction mixture thus obtained is refluxed for 30 minutes.

Extraction is then performed with organic solvents and $H_2O$.

The resulting product is purified on a silica column using a suitable mixture of organic solvents, known by persons skilled in the art.

The purified product is then purified using rotary evaporation.

Step 4

In a dry ampoule, 1 equivalent of the product obtained in step 4, i.e., 2-[2-(2-{2-[2-(2-undec-10-enyloxy-ethoxy)-ethoxy]-ethoxy}-ethoxy)-ethoxy]-ethoxy-maleimide (m=6), is dissolved in dry toluene.

All water is eliminated by means of rotary evaporation at reduced pressure. This step is repeated twice.

A trace of $H_2PtCl_6 \cdot xH_2O$ (~0.0012 g per 0.5 g of alkene) and dry toluene are then added and all water is eliminated by means of rotary evaporation at reduced pressure and increased temperature.

A magnetic stirrer is added and the ampoule is immediately closed with a septum while still being kept under argon atmosphere.

1.2 equivalents of $HSiOEt_3$ are then added and the reaction mixture is stirred for 30 minutes at 90° C.

The resulting product is then purified by dissolution in toluene followed by rotary evaporation at reduced pressure.

For the preparation of the trichlorosilane variant, i.e., wherein A in formula (1) is $Cl_3Si$ instead of $OEt_3Si$, the same procedure as described above can be followed wherein $HSiCl_3$ is used as a reagent instead of $HSiOEt_3$.

In a third aspect, a method is provided for the deposition of a self-assembled monolayer comprising first silane molecules according to the first aspect and having general formula:

$$A\text{-}(CH_2)_n\text{---}(O[CH_2]_t)_m\text{---}(CH_2)_v\text{---}Y \quad (1)$$

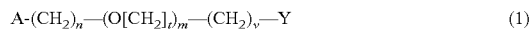

(see first embodiment of this third aspect) or for the deposition of a mixed film of silane molecules, i.e., a film which comprises at least two different silane molecules, for example, a first and a second silane molecule (see second embodiment of this third aspect).

In a first step of the deposition of a silane film, which step is the same for the first and second embodiment of the third aspect, a substrate is provided. The substrate can be an inorganic substrate or an organic substrate. Inorganic substrates can for example comprise, but are not limited to, silicon, glass, silica, quartz, metal oxides, and the like. Metal oxide or glass substrates can be, but are not limited to, silicon oxide, indium tin oxide, magnesium oxide, titanium oxide, tantalum oxide, zirconium oxide, niobium oxide, palladium oxide, platinum oxide, ruthenium oxide, quartz, glass, or silica. Organic substrates can comprise organic polymers such as, e.g., polyvinyl alcohol polymers, acrylic acid polymer and others. The substrates can be modified to obtain reactive groups such that the silanes can bind onto the substrate. The substrate can be in the form of an optical fibre, a wire, wafer, discs, planar surfaces, microscope slides, or beads. The substrate can also be a sensor, a biosensor, a DNA chip, a protein chip, a microarray, a microscope slide, a silicon wafer, or a microelectronic surface. Furthermore, the substrate can be a part of a transducer, which can be, but is not limited to, a Surface Plasmon Resonance (SPR) sensor, Optical Waveguide Sensor, Surface Acoustic Wave (SAW) sensors, Quartz Crystal Microbalance, amperometric sensors, capacitive sensors, interdigitated electrodes, or chemFET sensors. The surface can also be a surface having magnetic properties such as, e.g., a magnetic particle, which is an example of a 3D substrate. The magnetic particle can comprise a magnetic metal oxide material such as, e.g., $Fe_2O_3$ or $Fe_3O_4$ or $MFe_2O_4$ (with M=Co, Mn, or the like) optionally being coated with a stabilising layer. The stabilising layer can, for example, be a layer of $SiO_2$ or a layer of organic polymers. Preferably, the substrate can be glass or a substrate comprising a metal oxide. Optionally, the substrate can be prepared (or cleaned) prior to silanisation, in order to introduce reactive hydroxyls and/or to introduce the right amount of water.

The substrate can then preferably be cleaned. For this cleaning step, a lot of cleaning methods are known in literature, using various combinations of acids, bases, and organic solvents at different temperatures. The majority of silanisation procedures available in the literature recommend the use of a so-called 'piranha' cleaning for 1 h, immediately prior to the silanisation process. A piranha solution is a mixture of concentrated $H_2O_2$ (30% v/v) and concentrated $H_2SO_4$ (96% v/v), mixed in a ratio of respectively 1/4 or 3/7. As the piranha solution is a strongly oxidising solution, the hydrocarbon contamination will be removed from the surface of the substrate and thin oxide films will be further oxidised. As an alternative to wet chemical cleaning, UV or $UV-O_3$ based cleaning can also be applied. The cleaning procedure, if performed, can preferably be done as outlined in Table 1.

TABLE I

Example of an optional cleaning procedure for the substrate.

| cleaning step | chemicals | volume ratio | duration | temperature |
|---|---|---|---|---|
| Piranha | $H_2O_2$ (30% v/v)/$H_2SO_4$ (96% v/v) | 1/4 | 15 min | 90° C. |
| Rinse | ultrapure water | | 5× | room T° |
| SC1 | $H_2O_2$ (30% v/v)/$NH_3$ (29% v/v)/$H_2O$ | 1/1/5 | 10 min | 70° C. |
| Rinse/dry $N_2$ | ultrapure water | | 5× | room T° |

In a first embodiment according to this third embodiment, a method is provided for the deposition of a silane film comprising silane molecules combining pre-activated and protein-resistant functionalities and having general formula:

$$A\text{-}(CH_2)_n\text{---}(O[CH_2])_m\text{---}(CH_2)_v\text{---}Y \quad (1)$$

wherein:
1) The A-functionality has the ability to covalently bind or adsorb onto a substrate. A can be one of $X_3S_1$, $X_2R^1Si$, and $XR^1R^2Si$, wherein X can be a halo or alkoxy group, preferably a chloro- or an ethoxy group and wherein $R^1$ and $R^2$ can be one of $CH_3$— or $CH_3$—$CH_2$— or an other alkyl chain, which can optionally be interrupted by heteroatoms. Preferably, A can be $Cl_3Si$— or $EtO_3Si$—.
2) —$(CH_2)_n$— is an alkyl chain, which enables the formation of an ordered self assembled monolayer (SAM) film on a substrate surface, on the basis of van der Waals interactions between adjacent chains in the self-assembled monolayer film. In this alkyl chain, n is the number of repetitive methylene units and can be any number from 0 to 30. Preferably n can be from 6 to 22. Even more preferably, n can be from 8 to 18. The described alkyl chain can optionally be interrupted by p heteroatoms, wherein p is such that n+p can be from 0 to 30.
3) —$(O[CH_2]_t)_m$— is an oligo(alkylene glycol) chain, which is able to counteract the non-specific adsorption of biological moieties onto the surface. T can be from 1 to 10, preferably from 1 to 5 and most preferably t is 2. In this chain, m is the number of repetitive ethylene glycol and can be any number from 0 to 50. Preferably, m is from 3 to 22. Even more preferably, m is from 3 to 6. For values of m larger than 6, the silane molecules become too large and the layer formed by the silane molecules becomes too thick, hereby loosing optimal functionality of the silane molecule when it is, for example, used as an interface layer in a sensor. For m values lower than 3, the protein-resistant functionality becomes less pronounced.
4) —$(CH_2)_v$— is a spacer that links the oligo(ethylene glycol) chain with the functional group Y (see further in point 5). This spacer can comprise a branched or linear alkyl chain wherein v is preferably from 0 to 5. In specific cases and for silane molecules comprising particular Y groups such as, e.g., maleimide, this spacer can be absent, i.e., v is zero. The alkyl chain can optionally be interrupted by q heteroatoms, wherein q is preferably such that v+q is from 0 to 5. An example of a spacer is a spacer with, e.g., v=1 and q=1, i.e., —O—$CH_2$—.
5) Y is a functional group for binding biological moieties onto the silane molecule which can form a monolayer on a substrate. According to the preferred embodiments, Y is preferably a highly reactive functional moiety compatible with monolayer formation which needs no in situ activation prior to reaction with the biological moiety. Y can for example be, but is not limited to, conjugated carbonyls, epoxy, nitriloacetic acid, cyano, hydrazide, aziridine, sulfonylchloride, trifluoromethyldiaziridine, pyridylsulfide, N-acetyl-imidazole, vinylsulfone, arylazide, anhydride, diazoacetate, haloacetyl, benzophenone, isothiocyanate, isocyanate, biotin, halogen substituted benzene, pyridyldisulfide, protected carboxyl, protected amine, protected sulfohydryl, protected maleimide. Preferably, Y can be a conjugated carbonyl. Unlike other carbonyl function such as, e.g., aldehydes (—CH=O), conjugated carbonyls are functional groups which are compatible with the silylation step necessary to introduce a silane functionality in the final synthesis step of the silane molecule according to the first aspect (see further). In order to retain the pre-activated coupling properties of the carbonyl it is desired that the silylation occurs selectively on the alkene instead of on the carbonyl in the coupling group. Silylation of a carbonyl however, is more likely to occur compared to the alkene due to the high affinity of Si for O. However, when these carbonyls are conjugated, they are protected against this silylation reaction. Conjugated carbonyls comprise all carbonyls that comprise an electronegative heteroatom (e.g., N or O) adjacent to the carbonyl function or that comprise an α,β-unsaturated function or a combination of both. The adjacent heteroatom can be, but is not restricted to, a part of the spacer. Examples of preferred conjugated carbonyls which can be used according to the preferred embodiments can be fluor substituted benzoate, pentafluorophenylester, N-hydroxysuccinimide ester, acid halogenide or maleimide.

Figure 10:
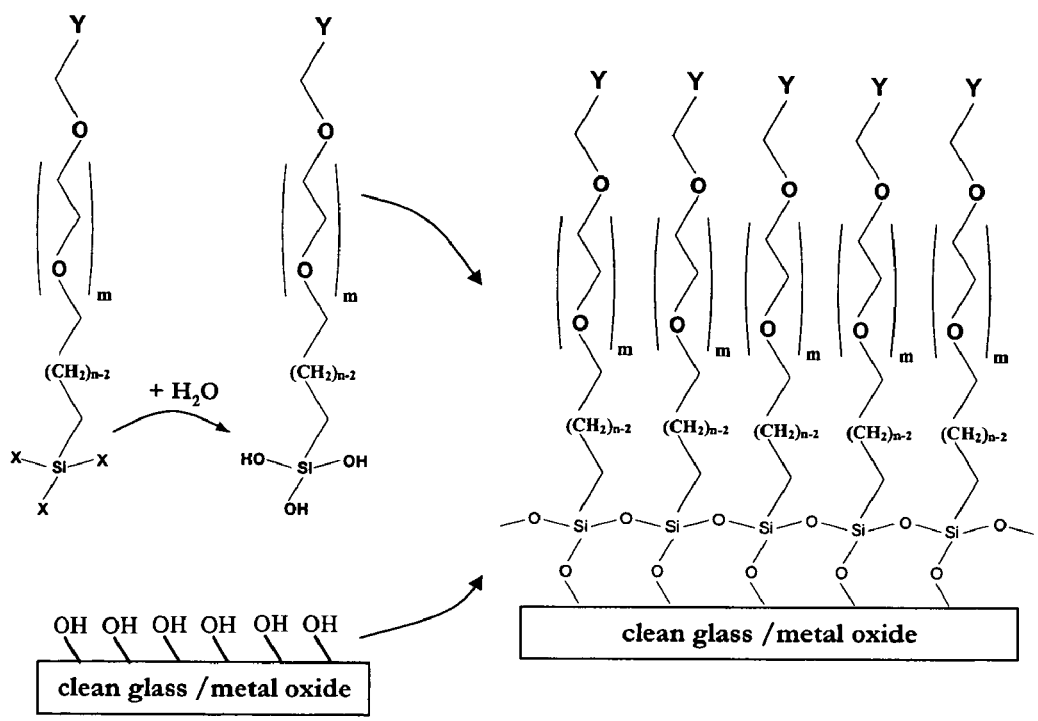
FIG. 10 is a schematic presentation of a SAM formed from a silane molecule according to embodiments of the invention.

FIG. 10 illustrates a substrate comprising a self-assembled monolayer or SAM of silane molecules according to the first aspect. Preferably the substrate can be a glass substrate or a metal oxide substrate.

For the deposition of silane molecules combining pre-activated and protein-resistant functionalities and having formula (1) in a homogeneous manner, two methods can be applied, i.e., deposition from a solvent, also called liquid phase silanisation, and vapour phase deposition. Both methods are commonly used in silane technology. Most often, self-assembly is performed under solution conditions, at room temperature, using a wide variety of solvents. In the prior art methods vapour phase deposition of chlorosilanes is preferred because it is believed to give rise to well-ordered SAMs, with a higher reproducibility and a higher stability, compared to liquid phase deposition.

According to the preferred embodiments, silane molecules can be deposited by means of liquid phase deposition. In that way, it is possible to form well-defined SAMs. It has, however, to be understood that it can also be possible to deposit silane molecules using vapour phase deposition. In that case, however, the apparatus used to perform the vapour phase deposition is preferably such that it can be used at rather high temperatures and low vacuum, as the silane molecules have a high boiling point and it is not easy to evaporate them.

Hereinafter, a possibility for depositing the silane molecules according to the first aspect, using liquid phase silanisation will be described. It has, however, to be understood that this is not limiting and that silane molecules according to the first aspect can also be deposited using other suitable deposition techniques known by persons skilled in the art. In the example given, the liquid silanisation can be performed from solutions comprising 0.01 to 10% (v/v), for example, 2% (v/v) of a silane molecule according to the first aspect with the general structure of formula (1), in a n-alkane solvent, such as for example hexane, decane or hexadecane. Other suitable solvents can include $CCl_4$, a solvent mixture of, e.g., hexadecane (70% v/v) and $CCl_4$ (30% v/v), or other volume ratios of said solvents. Another solvent that can be used for the silanisation process is toluene. In order to decrease the amount of water in the toluene solution, it can preferably be distilled prior to use, for example, over Na. The solvent can optionally be dried using, for example, molecular sieves. In addition to drying the solvent, the silanisation can be performed in a dry box under an inert atmosphere.

For the silanisation of substrates comprising, e.g., glass or metal oxide, using the silane molecules according to the first aspect, the reaction times can be surprisingly short, i.e., between 10 minutes and 1 hour. The final stage of the formation of a well-ordered SAM from alkylsilanes can take from 1 to 6 hours, or in some cases even longer.

The above example uses trichlorosilane as a silane compound. However, other silane compounds, such as alkoxy silanes, can also be used.

In the deposition of silanes, different parameters can be changed, i.e., type of solvent, time, silane compound concentration, temperature, addition of water or aqueous solutions, such as an acid or base. For example, when trichlorosilane is used as a silane compound, preferably no water or aqueous solution is added, while in case of an alkoxysilane as a silane compound, preferably water or an aqueous solution can be added. Because these different parameters can, in other processes, have different values, a lot of different possibilities for the deposition of the silane molecules are taken into account.

Figure 11:
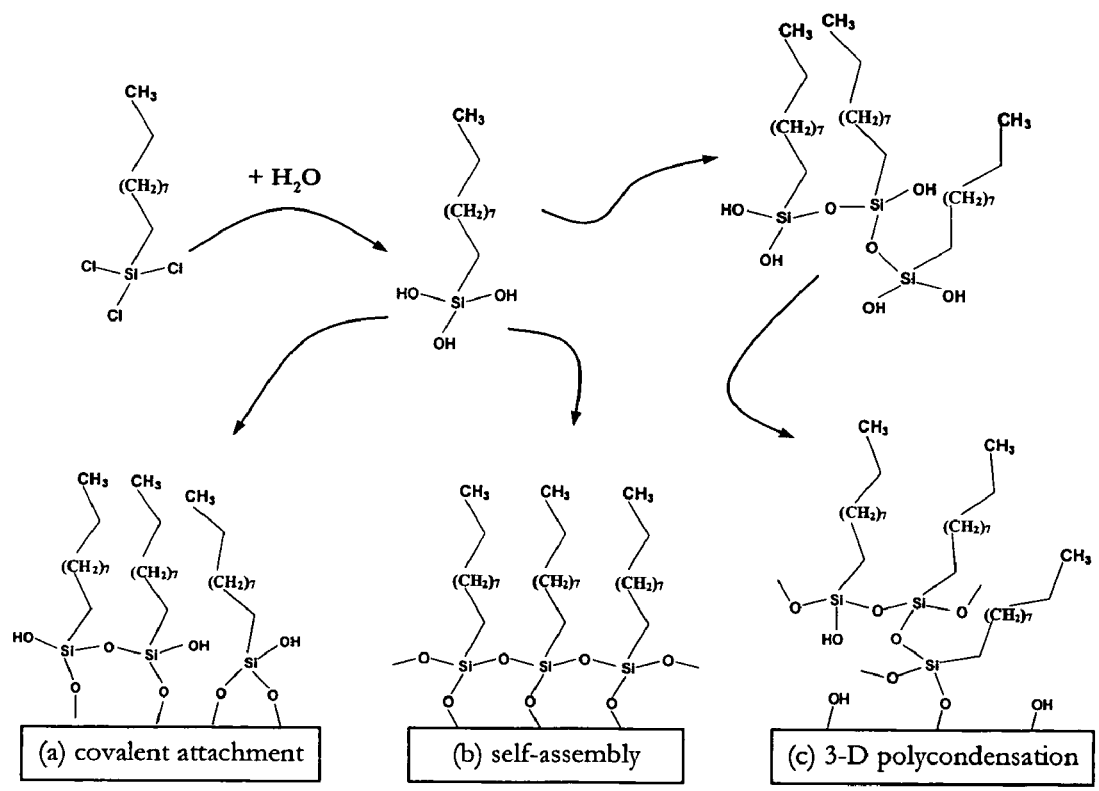
FIG. 11 is a schematic illustration of possible reactions and possible products of reactions of alkyltrichlorosilanes in solution with oxide surfaces.

A schematic representation of the various mechanisms by which silane molecules hydrolyse from a silane solution and on the clean surface and by which they subsequently bind onto the surface, is depicted in FIG. 11, for a model silane compound, i.e., (n-decyl)trichlorosilane.

The silanisation process can be preferably performed as outlined in Table II. The silanisation protocol as described in table II was shown to give rise to silane films of very good quality, compared to silane films deposited following other protocols [W. Laureyn, 'Physico-chemical study on the use of silanes for the realisation of oxide-based biosensor interfaces', PhD thesis, K. U. Leuven (2002)]. More specifically, the silanisation protocol is optimised in order to obtain silane SAMs with a high degree of order.

TABLE II

Preferred protocol for the silanisation process according to the third aspect.

| | Details procedure |
|---|---|
| Preparation glass beakers | |
| cleaning | piranha cleaning (table above) for 1 h |
| dehydration | rinse $H_2O$/rinse acetone/few hours at 110° C. |
| silanisation | 4-6 h in solution of 0.5% (v/v) DTS in dry toluene, under $N_2$ |
| dehydration | rinse toluene/rinse acetone/overnight at 110° C. |
| sample silanisation | cool down under $N_2$/rinse toluene/fill with silane solution |
| cleaning & dehydration | rinse toluene/rinse acetone/overnight at 110° C. |
| Dry cleaning sample | |
| wet cleaning | piranha and SC1 cleaning (table above) |
| transfer to dehydration | rinse $H_2O$/rinse acetone/dry with $N_2$ flow |
| dehydration | 15-20 min on hotplate at 110° C. (under $N_2$) |
| UV—$O_3$ cleaning | 15 min UV—$O_3$ each sample side/store under $N_2$ |
| Silanisation sample | |
| silane solution | 1% (v/v) silane in dry toluene, under $N_2$ (in silanised glass beaker) |
| silanisation | immerse dry cleaned sample for 3 h in silane solution, under $N_2$ |
| remove excess silane | rinse toluene/$CCl_4$/acetone/MeOH/$H_2O$/MeOH/acetone (each 2×) |
| crosslinking silanes | dry with $N_2$ flow/15-30 min at 110° C. |

As a model system, n-decyltrichlorosilane (DTS) was deposited on a double-side, polished silicon substrate with a native $SiO_2$ layer (DSP $SiO_2$). Several key experimental conditions were varied, i.e., the solvent and its water content, the substrate cleanliness and hydration, the container in which the silanisation of the substrates is performed in, the reaction time and the deposition temperature.

The combination of a dry cleaning and the use of dry toluene leads to an amount of water in the solution and on the surface, which is optimal for obtaining well-organised monolayers. Finally, it was found from infrared spectroscopy analysis, that the silane layers become more ordered as a function of time and that a controlled reaction time of, for example, 3 hours can be required. The optimised silanisation procedure for the silanisation of DSP $SiO_2$ with DTS (see Table II) leads to relatively low hysteresis values, relatively high sessile drop contact angle and advancing contact angle values, and wavenumbers $v_a(CH_2)$ and $v_s(CH_2)$ positions of $2922.8\pm0.4$ cm$^{-1}$ and $2853.3\pm0.2$ cm$^{-1}$, respectively. These characteristics are indicative for the formation of quasi-crystalline monolayers from n-alkyltrichlorosilanes, with a relatively low chain length (i.e., DTS) on $SiO_2$.

In addition, the optimised silanisation procedure was applied to native $Ta_2O_5$ films, in order to allow the realisation of highly ordered DTS monolayers on $Ta_2O_5$ surfaces. It was found that the resulting DTS silane films are complete, dense, and essentially pinhole-free and show a relatively high degree of order, comparable to DTS SAMs on $SiO_2$ surfaces.

Furthermore, the influence of the type of cleaning on the silanisation of $Ta_2O_5$ with DTS was studied. This study revealed incomplete and disordered silane films on uncleaned $Ta_2O_5$ surfaces. On the opposite, the DTS SAMs on wet-cleaned and dry-cleaned $Ta_2O_5$ surfaces both exhibited a relatively high amount of order and appeared to be pinhole-free. After silanisation, both cleaned samples also showed the most pronounced change in the elemental concentrations and sub-regions from the XPS spectra. In addition, the formation of quasi-ideal DTS silane layers on both cleaned samples was indicated. The limited differences between the DTS SAMs on wet-cleaned vs. dry-cleaned $Ta_2O_5$ samples might be due to the higher number of hydroxyl groups on a clean $Ta_2O_5$ surface, compared to $SiO_2$. Because slightly superior characteristics of the DTS SAM on the dry-cleaned $Ta_2O_5$ sample were indicated, the dry cleaning procedure will be used in the remainder of this study.

In a second embodiment of the third aspect, a mixed silane film is deposited onto a substrate. The mixed silane film comprises at least two different silane molecules, for example, first and second silane molecules. The first silane molecule is a silane molecule according to the first aspect with general formula (1). The second silane can have a similar general chemical formula and can immobilise the same or a different biological moiety.

Preferably, the mixed silane film comprises first silane molecules having general formula (1) and furthermore comprises second silane molecules having general formula:

B—$(CH_2)_o$—$(O[CH_2]_x)_r$—Z  (4)

wherein:
1) The B-functionality has the ability to covalently bind or adsorb onto a substrate as described above. In a preferred embodiment, the substrate can comprise glass or metal oxide. The metal oxide or glass surfaces can be, but are not limited to, silicon oxide, indium tin oxide, magnesium oxide, titanium oxide, tantalum oxide, zirconium oxide, niobium oxide, palladium oxide, platinum oxide, ruthenium oxide, quartz, glass, or silica. B can be one of $W_3Si$—, $W_2R^1Si$—, and $WR^1R^2Si$—, wherein W can be a halo or alkoxy group and $R^1$ and $R^2$ can be $CH_3$— or $CH_3CH_2$— or any other alkyl chain, optionally interrupted by heteroatoms. Preferably, W can be a chloro- or an ethoxy group, and thus B is preferably $Cl_3Si$ or $EtO_3Si$.
2) —$(CH_2)_o$— is an alkyl chain, which enables the formation of an ordered monolayer film on the substrate, on the basis of van der Waals interaction between adjacent chains in the self-assembled monolayer film. O is the number of repetitive methylene units in the alkyl chain and can be any number from 0 to 30. Preferably O is from 6 to 22. Even more preferably, O is from 8 to 18. The described alkyl chain can be optionally interrupted by q heteroatoms wherein o+q can be any number from 0 to 30.
3) —$(O[CH_2]_x)_r$— is an oligo(alkylene glycol) chain, which is able to counteract the non-specific adsorption of biological moieties onto the surface and wherein r is the number of repetitive ethylene glycol units in the oligo (ethylene glycol) chain and can be any number in from 0 to 50. Preferably r is from 3 to 22. Even more preferably, r is 3 or 6 and x is from 1 to 10, preferably from 1 to 5 and most preferably x is 2.
4) Z is a moiety resistant to the non-specific binding of biomolecules. The possibilities for Z will vary depending upon the nature of the biological moiety chosen for. According to various embodiments, functional groups Z, which are resistant to non-specific protein binding, are used when the immobilised biological moiety of the device comprises proteins. The nature of Z will depend on the type of proteins and solutions used. In a preferred embodiment, Z can comprise a hydroxyl group, an alkoxy group, a saccharide, or an oligo/polyethylene glycol moiety. In a more preferred embodiment, Z can be an ethoxy or a methoxy group.

Figure 12:
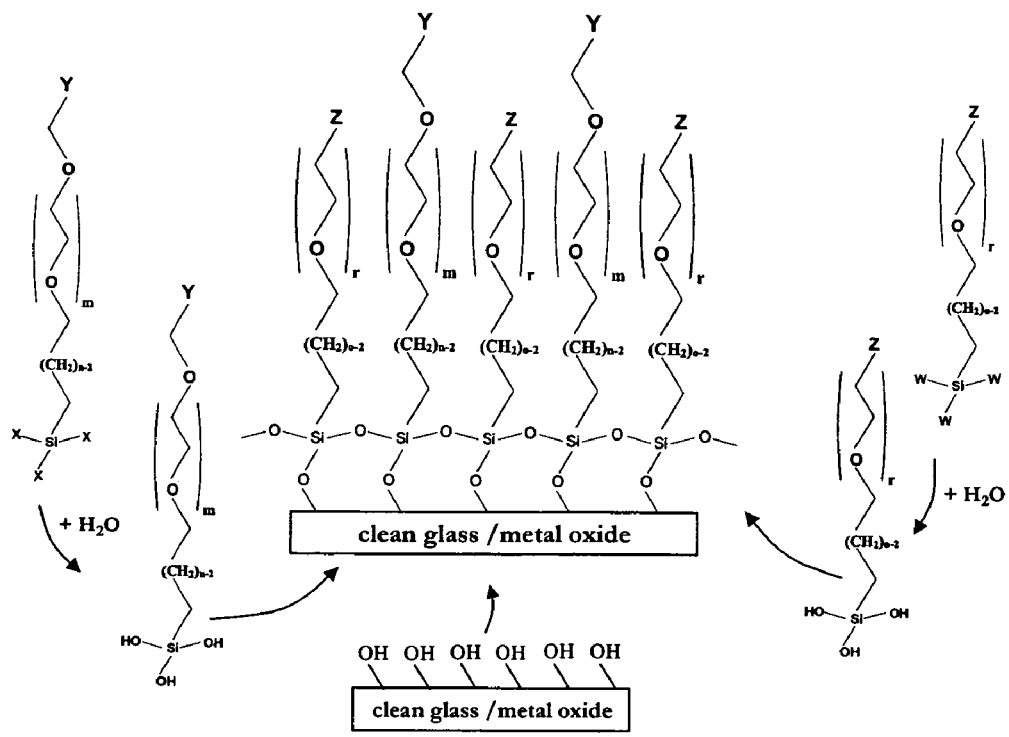
FIG. 12 is a schematic illustration of a mixed silane film.

A schematic illustration of a mixed silane according to this second embodiment is given in FIG. 12. Such a mixed silane film thus comprises mixed monolayers, which comprises at least two different silane molecules.

The homogeneous and mixed silane films can be deposited in a similar way as the silane film comprising only a first silane molecule and thus as described in the first embodiment of the third aspect by adding any amount of the individual silane molecules to the silanisation solvent. More specifically, the mixed silane film can be deposited from a solution that comprises 0 to 100% ($v_{silane1}/v_{total\ silane}$) of the first silane and 100 to 0% ($V_{silane2}/V_{total\ silane}$) of the second silane molecule.

The second silane molecule provides protein-resistant functional groups for lowering the non-specific adsorption of proteins onto the surface of a substrate on which the molecules are present.

In a specific example according to the second embodiment of the third aspect, the second silane molecule in the mixed silane film can have the formula:

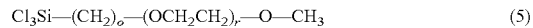

$Cl_3Si$—$(CH_2)_o$—$(OCH_2CH_2)_r$—O—$CH_3$  (5)

wherein o can be any number from 8 to 18 and r can be 3 or 6. In this example, the Z-group is a methoxy group.

Hereinafter, three examples of preferred second silane molecules and their synthesis will be described.

EXAMPLE 8 synthesis of trichloro-(11-{2-[2-(2-methoxy-ethoxy)-ethoxy]-ethoxy}-undecyl)-silane In this first example, the synthesis is described of a second silane molecule having formula:

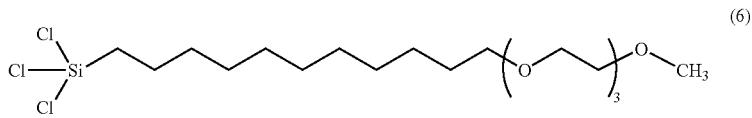

(6)

Figure 13:
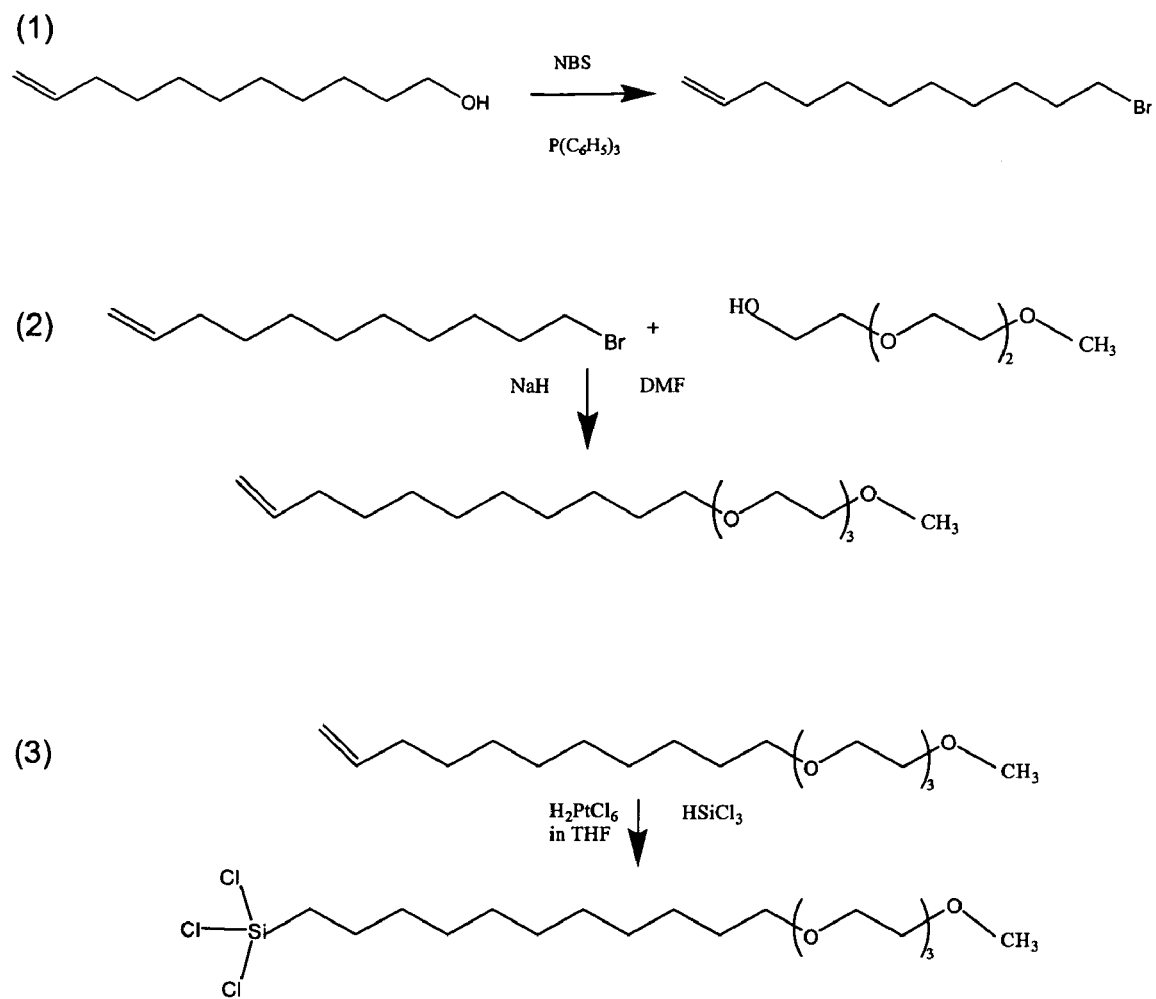
FIG. 13 illustrates the synthesis of trichloro-(11-{2-[2-(2-methoxy-ethoxy)-ethoxy]-ethoxy}-undecyl)-silane.

When this structure is compared to the general formula (4), it can be seen that for this molecule o=11 and r=3. A possible synthesis route for this molecule (6) is illustrated in FIG. 13.

Method:

Step 1: synthesis of 11-bromo-1-undecene

To a dry three neck bottle comprising a magnetic stirrer and being kept under reflux and nitrogen atmosphere 8.5 g (50 mmol) undecylenylalcohol+100 ml dichloromethane is added. The flask is cooled with acetone and solid $CO_2$ (down to −23° C.). 15.7 g (60 mmol) triphenylphosphine ($P(C_6H_5)_3$) is added to the mixture while stirring. Then, 9.8 g (55 mmol) N-bromosuccinimide (NBS) is further added and the reaction mixture is stirred for 1 hour (1 h) and is cooled down to −23° C.

The three neck bottle is removed from the cooling bath and the reaction mixture is further stirred for half an hour at room temperature.

The reaction mixture is extracted and washed with $Na_2CO_3$

The organic phase dried on $MgSO_4$, filtered and put on the rotavapor

The solution is extracted with hexane via reflux, is then filtered and then the hexane is evaporated.

The product is filtered via vacuum filtration over an alumina column (5 cm high, 3 cm diameter) and then washed with hexane.

The product is concentrated on the rotavapor.

Yield=8.51 g (36.5 mmol)=73%.

Observations and Results

The solution turns yellow after adding all reagents. The colour changes during extraction from yellow over purple to dark brown. There is a clear $H_2O$ layer present on top. After extraction a yellow solution with a dark precipitate is obtained. The final product is clear.

Figure 14:
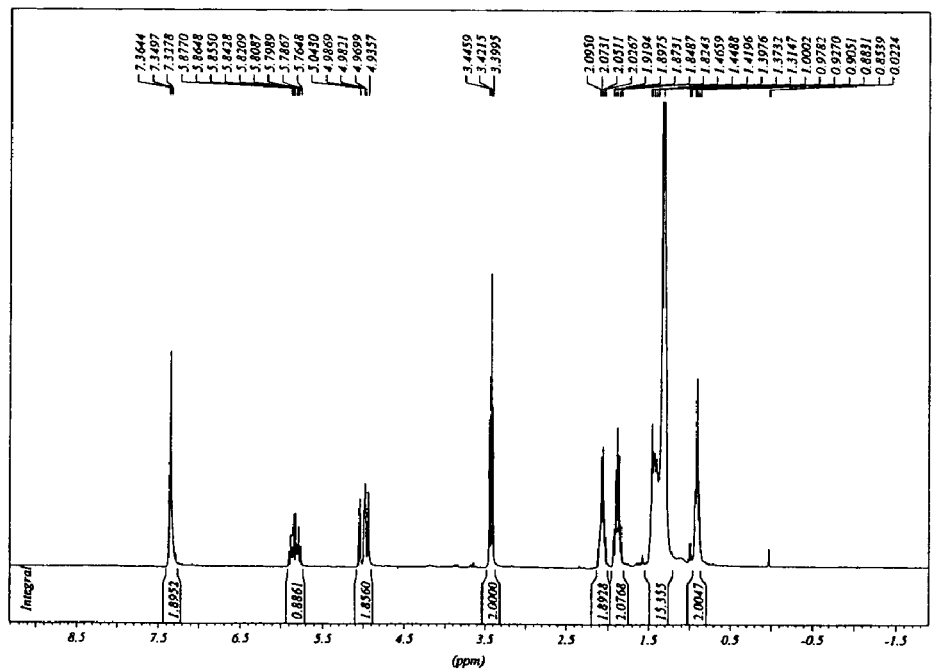
FIG. 14 illustrates the $^1$H NMR-spectrum of the intermediate product formed in the first step of the synthesis of trichloro-(11-{2-[2-(2-methoxy-ethoxy)-ethoxy]-ethoxy}-undecyl)-silane.

$^1$H NMR spectrum (See FIG. 14)

In the $^1$H NMR spectrum of 11-bromo-1-undecene triphenylphosphine impurity at 7.32 ppm 5.79 and 4.94 ppm=hydrogen of =CH and =$CH_2$ 3.39 ppm=hydrogen of $CH_2$ next to Br 0.8 ppm→2.2 ppm=other $\underline{CH_2}$'s

Step 2: synthesis of 11-{2-[2-(2-methoxy-ethoxy)-ethoxy]-ethoxy}-undec-10-ene In a dry three neck bottle comprising a magnetic stirrer and being under argon atmosphere 5.99 g (36.5 mmol) triethyleneglycol monomethylether together with a small excess NaH is dissolved in 100 ml dimethylformamide (DMF) and is stirred for 50 minutes.

8.51 g (36.5 mmol) 11-bromo-1-undeceen is added and the reaction mixture is stirred for 36 hours.

After that time, the reaction is quenched with methanol.

Then, DMF and methanol are removed at the rotavapor.

The solution is dissolved in 250 ml dichloromethane and extracted and washed with $H_2O$.

The organic phase is dried with $MgSO_4$+rotavapor.

The product thus obtained is then purified on a silica column with ethylacetate/petroleum ether (2/1)

Next, the product is concentrated on the rotavapor.

Yield=1.74 g (5.5 mmol)=15%.

Observations and Results

The colour changes during 50 minutes stirring form light yellow to dark brown (T ↑). After addition of 11-bromo-1-undecene→foaming. The foam dissolves and the reaction mixture gets dark brown colour.

High temperature+stronger vacuum required for removing MeOH and DMF→precipitates due to NaBr After extraction and washing the organic phase is brown and the $H_2O$ phase is yellow.

The first product from the silica column (Rf=0.82, EtOAc/petroleum ether 2/1) only comprises reagents, the second product from the silica column (Rf=0.49, EtOAc/petroleum ether 2/1) is the product (only visible using $I_2$)

Figure 15:
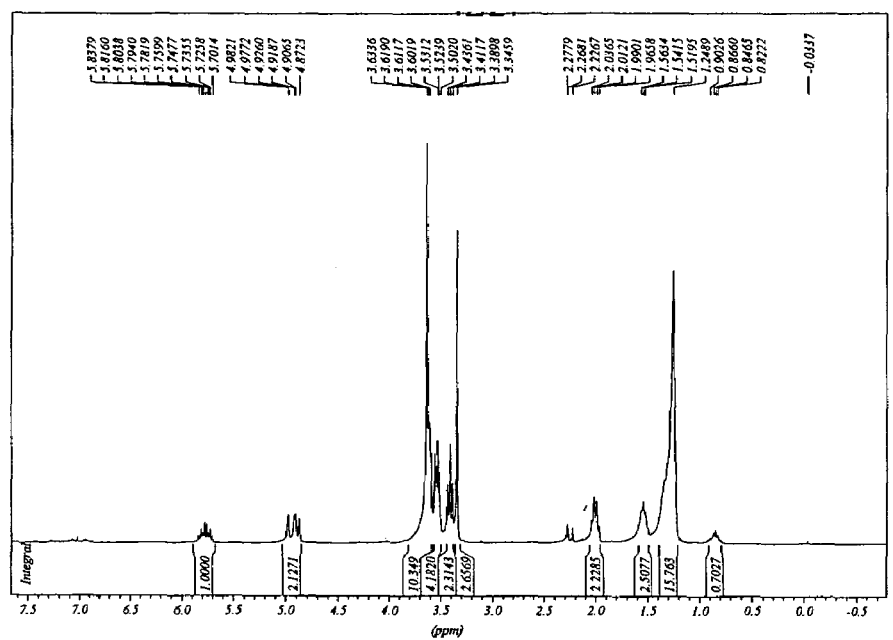
FIG. 15 and FIG. 16 respectively illustrate the $^1$H NMR-spectrum and the $^{13}$C NMR spectrum of the intermediate product formed in the second step of the synthesis of trichloro-(11-{2-[2-(2-methoxy-ethoxy)-ethoxy]-ethoxy}-undecyl)-silane.

$^1$H NMR-Spectrum (See FIG. 15)

Figure 16:
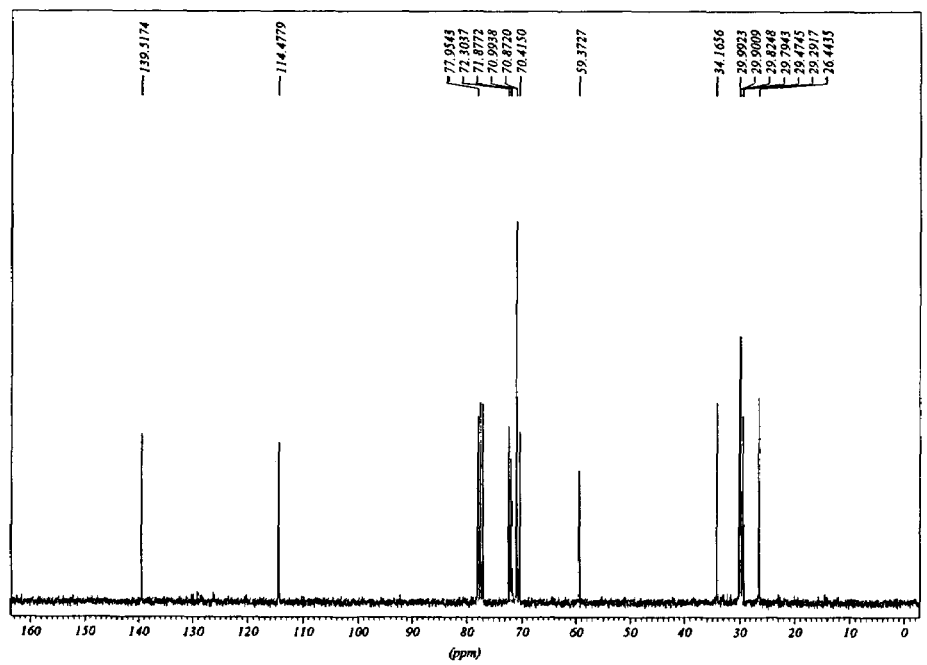

5.79 and 4.94 ppm=hydrogens of =CH and =CH 3.66→3.42=H's of three $OCH_2CH_2$'s 3.38 (singlet)=H of $OCH_3$ Other=H's of other $CH_2$'s No triphenylphosphine impurity $^{13}$C NMR-Spectrum (See FIG. 16)

139.51 and 114.48 ppm=$sp^2$ carbons C=C 70.47 ppm=$sp^3$ carbons of $OCH_2CH_2$'s 58.84 ppm=C of $OCH_3$-group.

Others=C's of the other $CH_2$'s

No triphenylphosphine impurity

Step 3: synthesis of trichloro-(11-{2-[2-(2-methoxy-ethoxy)-ethoxy]-ethoxy}-undecyl)-silane In a dry ampoule 1.64 g (5.3 mmol) 11-{2-[2-(2-methoxy-ethoxy)-ethoxy]-ethoxy}-undec-1-ene is dissolved in toluene and evaporated using the rotavapor, after which the resulting product is dried.

A magnetic stirrer is added and the ampoule is closed with a septum while being kept under argon.

1 ml of 0.01M solution of $H_2PtCl_6$ in dried tetrahydrofuran (THF)+0.62 ml (6.9 mmol) trichlorosilane ($HSiCl_3$) is added and the reaction mixture is stirred overnight at 90° C.

The resulting product is dissolved in toluene.

Toluene is removed.

Yield=1.8 g (3.98 mmol)=75%.

Observations and Results

After addition of HSiCl3→gas+yellow.

Figure 17:
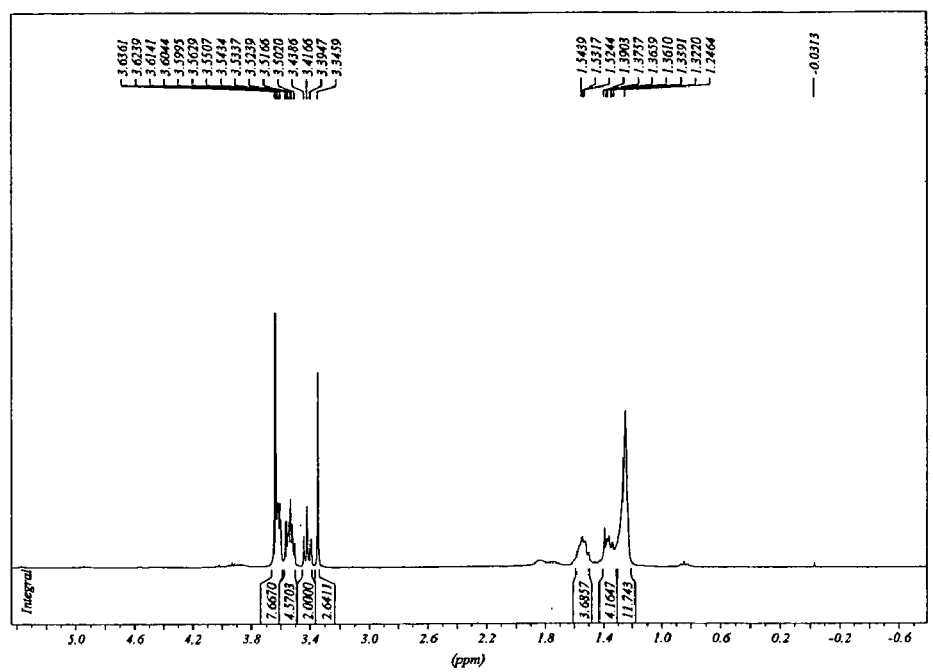
FIG. 17, FIG. 18 and FIG. 19 respectively illustrate the $^1$H NMR-spectrum, the $^{13}$C NMR spectrum and the $^{29}$Si NMR of trichloro-(11-{2-[2-(2-methoxy-ethoxy)-ethoxy]-ethoxy}-undecyl)-silane.

$^1$H NMR-Spectrum (See FIG. 17)

No more peaks for C=C 3.66 ppm→3.42 ppm =H's of $OCH_2CH_2$'s 3.38 ppm=H of $OCH_3$ Others=H's of other $CH_2$'s (shifted because of $Si(Cl)_3$)

Figure 18:
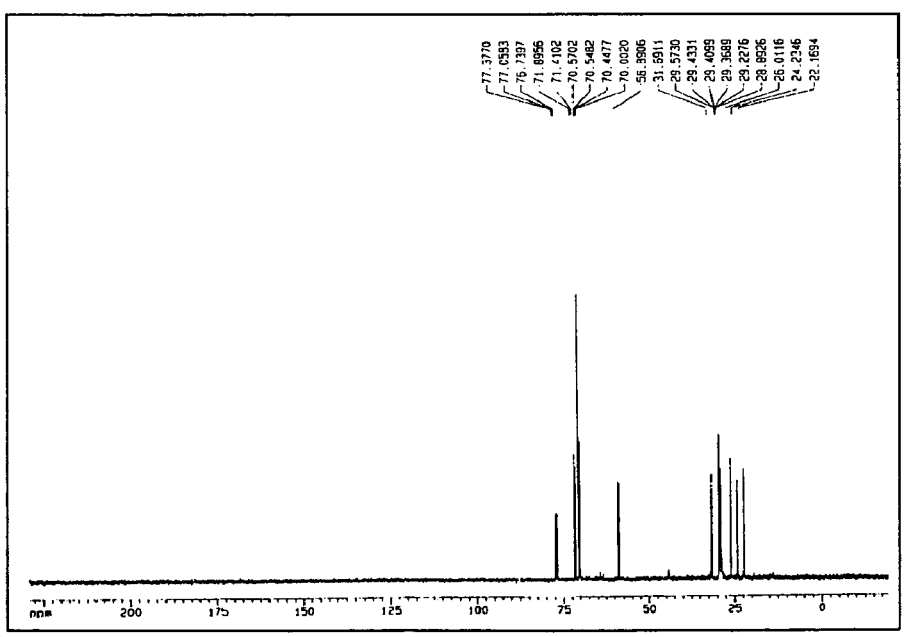

$^{13}$C NMR-Spectrum (See FIG. 18)

Figure 19:
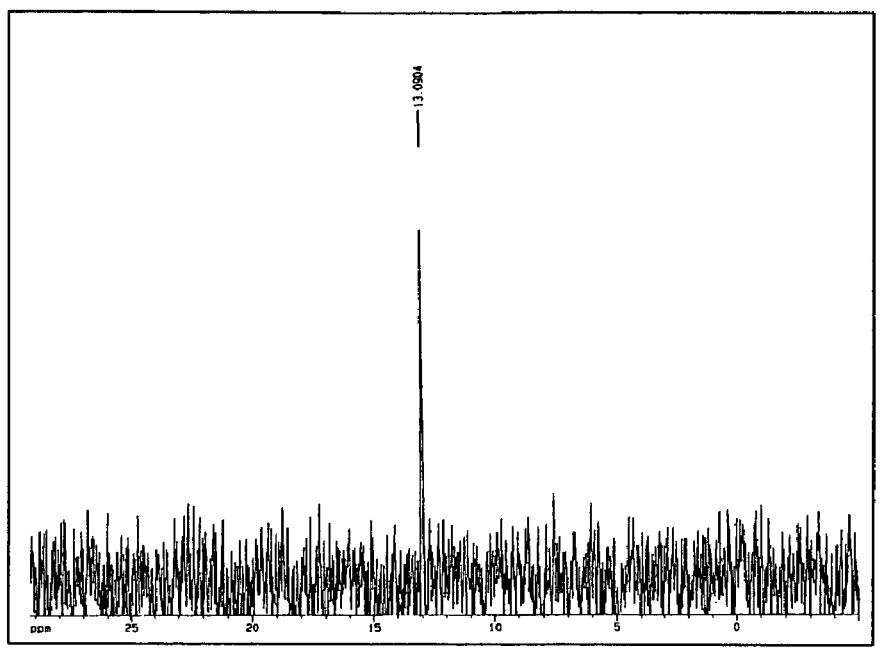

No more peaks for C=C 70.47 ppm=$sp^3$ carbons of $OCH_2CH_2$'s 58.84 ppm=carbon of $OCH_3$ 29.41 ppm=carbons of other $CH_2$'s 24.24 ppm and 22.17 ppm=sp$^3$ carbons next to Si(Cl)$_3$
$^{29}$Si NMR-Spectrum (See FIG. 19)
13.09 ppm=$^{29}$Si NMR-spectrum shows the Si next to 3 Cl's

EXAMPLE 9 synthesis of trichloro-[11-(2-{2-[2-(2-methoxy-ethoxy)-ethoxy]-ethoxy}-ethoxy)-undecyl]-silane In this second example, the synthesis is described of a second silane molecule having formula:

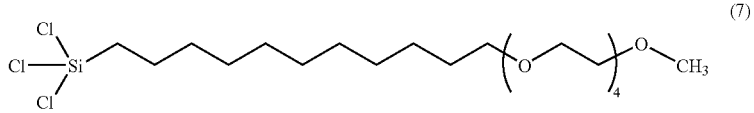

(7)

Figure 20:
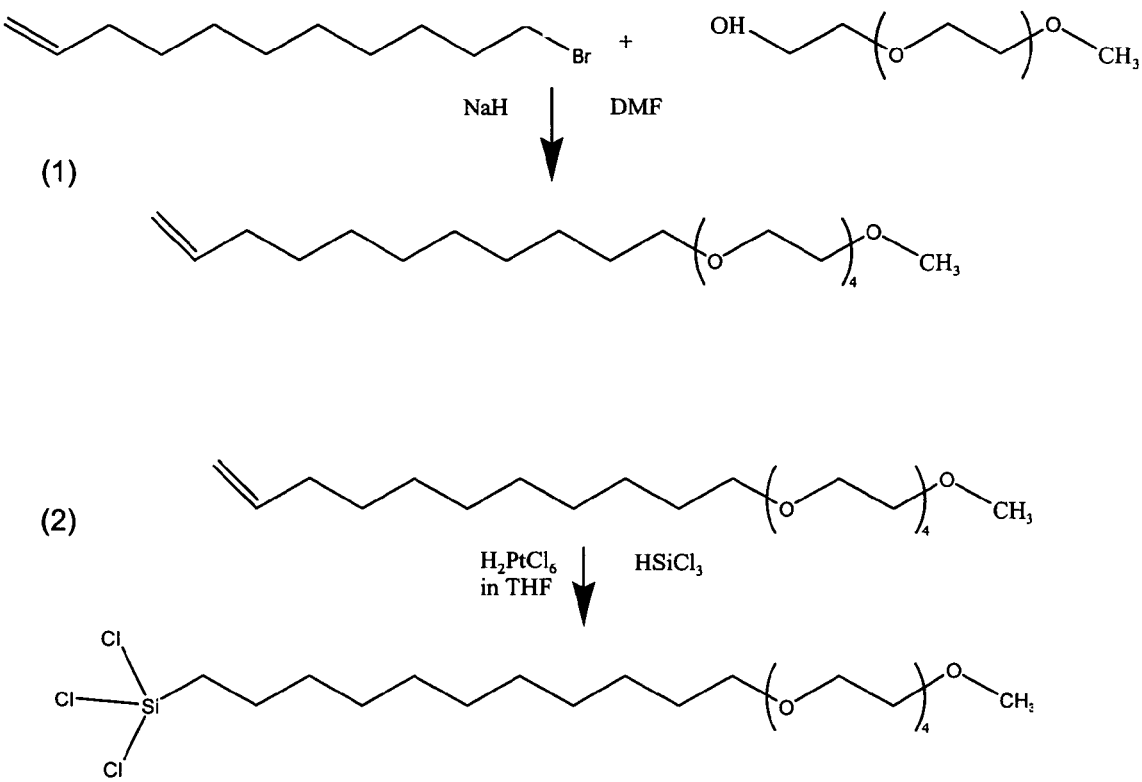
FIG. 20 illustrates the synthesis of 11'-(2-{2-[2-(2-Methoxy-ethoxy)-ethoxy]-ethoxy}-ethoxy)-undec-1-ene.

When this structure is compared to the general formula (4), it can be seen that for this molecule o=11 and r=4. A possible synthesis route for this molecule (7) is illustrated in FIG. 20.

Figure 21:
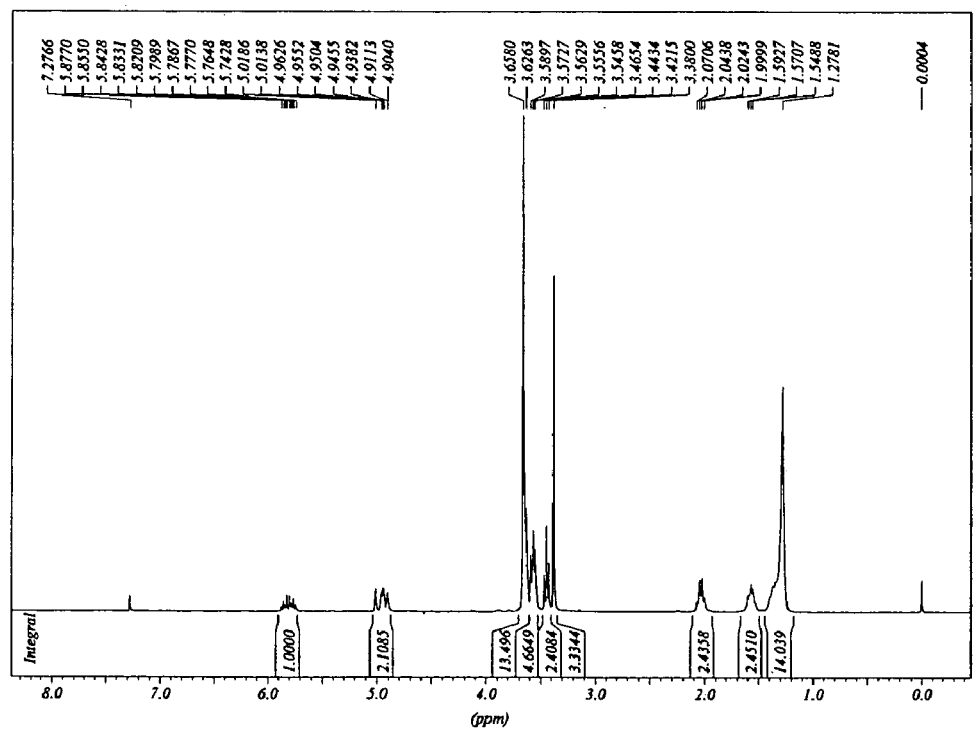
FIG. 21 illustrates the $^1$H NMR-spectrum of the intermediate product formed in the first step of the synthesis of 11-(2-{2-[2-(2-Methoxy-ethoxy)-ethoxy]-ethoxy}-ethoxy)-undec-1-ene.
Figure 22:
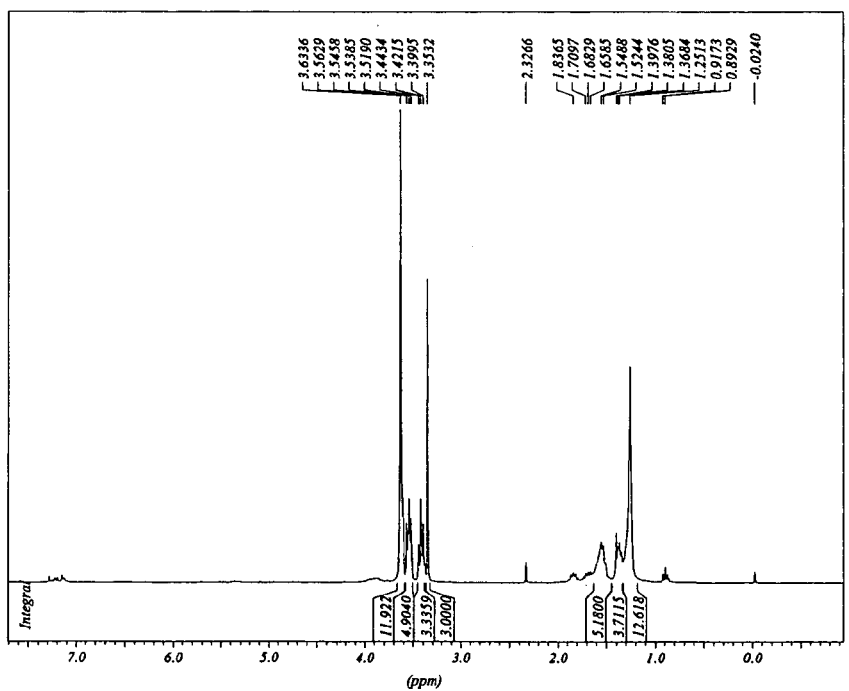
FIG. 22 and FIG. 23 respectively illustrate the $^1$H NMR-spectrum and the $^{13}$C NMR spectrum of 11-(2-{2-[2-(2-Methoxy-ethoxy)-ethoxy]-ethoxy}-ethoxy)-undec-1-ene.
Figure 23:
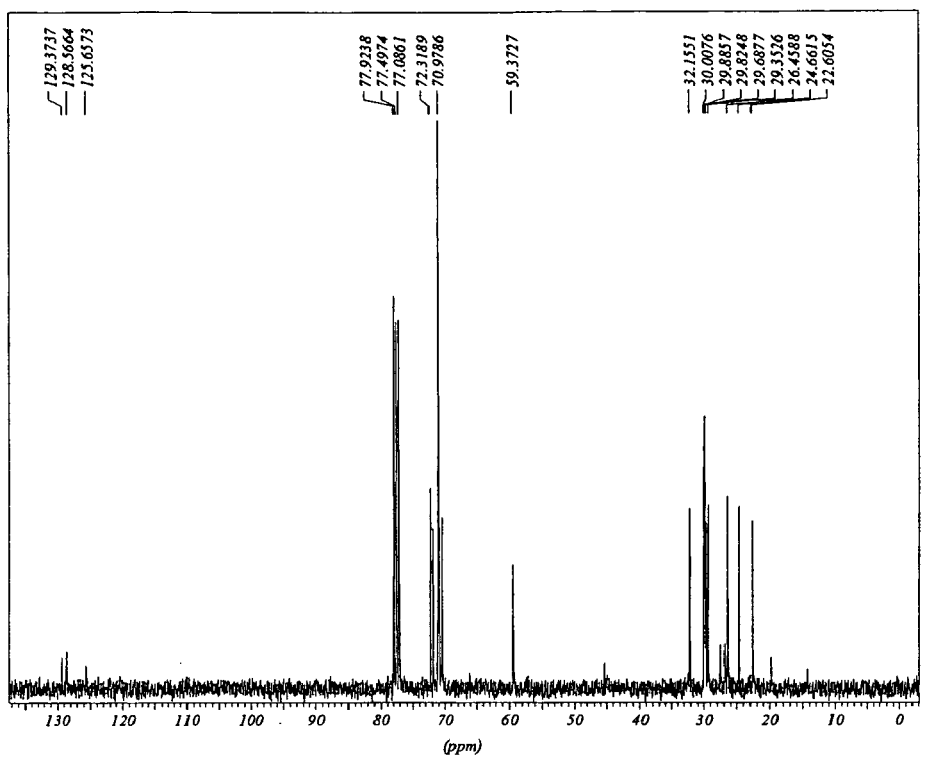

Method:

Step 1: synthesis of 11-(2-{2-[2-(2-Methoxy-ethoxy)-ethoxy]-ethoxy}-ethoxy)-undec-1-ene In a dry three neck bottle comprising a magnetic stirrer and being kept under argon atmosphere, 10 g (48 mmol) tetraethyleneglycol monomethylether together with a small excess NaH is dissolved in 100 ml THDF and 60 ml DMF and stirred for 50 minutes.
11.2 g (48 mmol) 11-bromo-1-undecene is added and the reaction mixture is stirred for 3 days.
Then the reaction is quenched with methanol.
Next, methanol, DMF and THF are removed at the rotavapor.
The solution is dissolved in 150 ml dichloromethane, extracted, and washed three times with H$_2$O.
The organic phase is dried with MgSO$_4$ and at the rotavapor.
The product obtained is then purified on a silica column with ethylacetate/MeOH (100/5)
The product is concentrated on the rotavapor.
Yield=3.6 g (10 mmol)=21%.
Observations and Results
Colour changes during 50 minutes stirring form light yellow to light brown (T ↑)
High temperature+stronger vacuum for removing MeOH and DMF→precipitates due to NaBr.
I$_2$ colouring necessary for TLC's.
Organic phase is brown and H$_2$O phase is yellow
$^1$H NMR Spectrum (See FIG. 21)
5.79 and 4.94 ppm=hydrogens of =CH and =CH$_2$
~3.66=H's of four OCH$_2$CH$_2$'s
3.45 (triplet)=H of CH$_2$'s next to OCH$_2$CH$_2$
3.38 (singlet)=H of OCH$_3$
1.2-2.1=H's of other CH$_2$'s Step 2: synthesis of Trichloro-[11-(2-{2-[2-(2-methoxy-ethoxy)-ethoxy]-ethoxy}-ethoxy)-undecyl]-silane In a dry ampoule 1.739 g (4.8 mmol) 11-(2-{2-[2-(2-methoxy-ethoxy)-ethoxy]-ethoxy}-ethoxy)-undec-1-ene is dissolved in toluene and twice evaporated using rotavapor after which the product is dried.
A magnetic stirrer is added and the ampoule is closed with a septum while being kept under argon atmosphere.
1 ml of 0.01M solution of H$_2$PtCl$_6$ (0.0043 g) in dried tetrahydrofuran (THF)+0.56 ml (5.5 mmol) HSiCl$_3$ is added and the reaction mixture is stirred overnight at 90° C.
The product is dissolved in toluene and subsequently the toluene is removed.
Yield=2.22 g (4.47 mmol)=92%.
Observations and Results
After addition of HSiCl3→gas+yellow. A black precipitate is present in the solution.
$^1$H NMR Spectrum (See FIG. 22)
No more peaks for C=C
~3.65 ppm=H's of OCH$_2$CH$_2$'s
3.45 (triplet)=H of CH$_2$'s next to OCH$_2$CH$_2$
3.38 ppm=H of OCH$_3$
Others=H's of other CH$_2$'s (shifted because of Si(Cl)$_3$)
$^{13}$C NMR-Spectrum (See FIG. 23)
No more peaks for C=C
70.47 ppm=sp$^3$ carbons of OCH$_2$CH$_2$'s
59.37 ppm=carbon of OCH$_3$
29.41 ppm=carbons of other CH$_2$'s
24.66 ppm and 22.61 ppm=sp$^3$ carbons next to Si(Cl)$_3$

EXAMPLE 10 synthesis of trichloro-(11-{2-[2-(2-{2-[2-(2-methoxy-ethoxy)-ethoxy]-ethoxy}-ethoxy)-ethoxy]-ethoxy}-undecyl)-silane In this third example, the synthesis is described of a second silane molecule having formula:

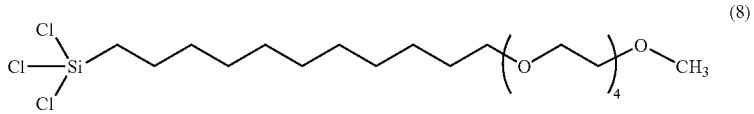

(8)

Figure 24:
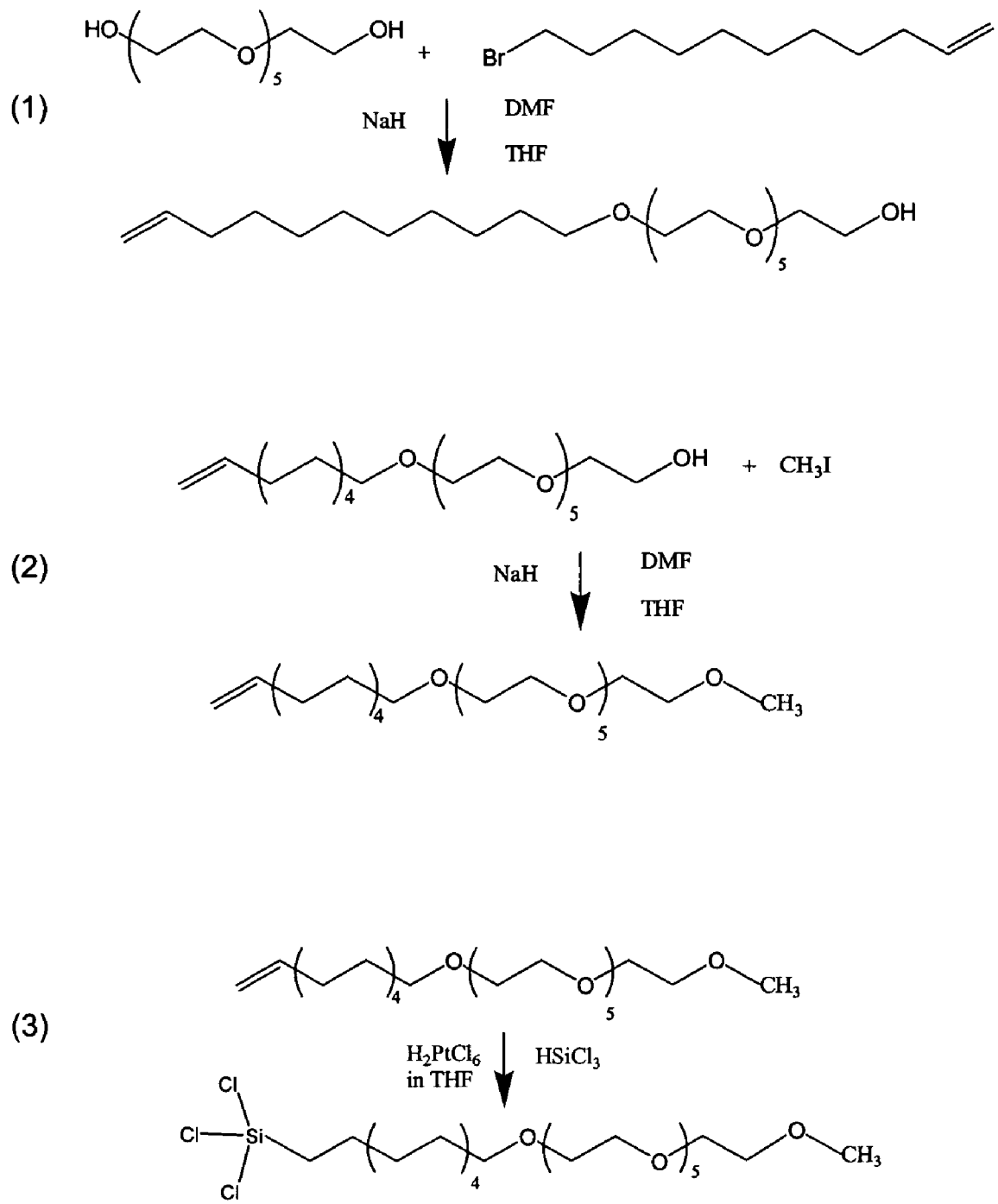
FIG. 24 illustrates the synthesis of trichloro-(11-{2-[2-(2-{2-[2-(2-methoxy-ethoxy)-ethoxy]-ethoxy}-ethoxy)-ethoxy]-ethoxy}-undecyl)-silane.

When this structure is compared to the general formula (4), it can be seen that for this molecule 0=11 and r=6. A possible synthesis route for this molecule (8) is illustrated in FIG. 24.

Method:

Step 1: synthesis of 2-[2-(2-{2-[2-(2-undec-10-enyloxy-ethoxy)-ethoxy]-ethoxy}-ethoxy)-ethoxy]-ethanol In a dry three neck bottle comprising a magnetic stirrer and being kept under argon atmosphere 25 g (88.5 mmol) hexaethylenglycol together with a small excess NaH is dissolved in 100 ml THF and 60 ml DMF and is stirred for 50 minutes.

10.32 g (44.3 mmol) 11-broom-1-undecene is added and the reaction mixture is stirred for 3 days.

Then, the reaction is quenched with methanol.

Methanol, THF and DMF are removed at the rotavapor.

The solution is then dissolved in 250 ml dichloromethane, extracted and washed three times with $H_2O$.

The organic phase is dried with $MgSO_4$ and is put on the rotavapor.

The product thus obtained is purified on a silica column with ethylacetate/MeOH (100/5).

The product is concentrated on the rotavapor.

Yield=9.532 g (22 mmol)=25%.

Observations and Results

Colour change during 50 minutes stirring from light yellow to light brown (T ↑)

High temperature+stronger vacuum for removing MeOH and DMF→precipitates due to NaBr.

After addition of brine→better separation

First product from the silica column is the di-substituted product (only visible using $I_2$) while the second product from the silica column is the mono-substituted product (only visible using $I_2$)

Figure 25:
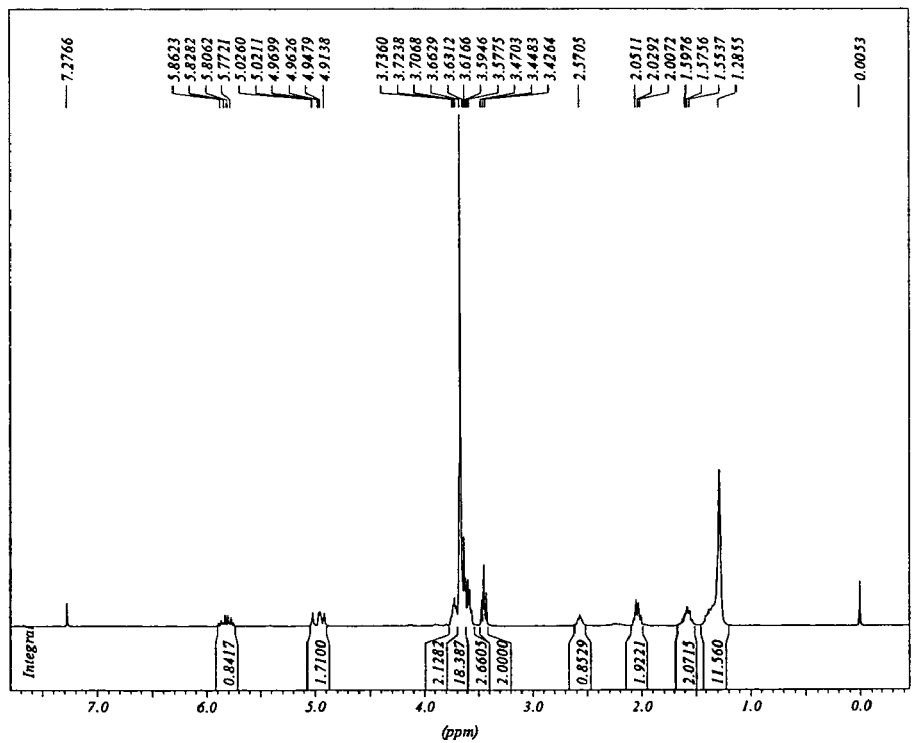
FIG. 25 illustrates the $^1$H NMR-spectrum of the intermediate product formed in the first step of the synthesis of trichloro-(11-{2-[2-(2-{2-[2-(2-methoxy-ethoxy)-ethoxy]-ethoxy}-ethoxy)-ethoxy]-ethoxy}-undecyl)-silane.

$^1$H NMR Spectrum (See FIG. 25)

5.82 and 4.95 ppm=hydrogens of =CH and =$CH_2$

~3.66=H's of six $OCH_2CH_2$'s 3.45 (triplet)=H of $CH_2$'s next to $OCH_2CH_2$ 1.2-2.1=H's of other $CH_2$'s Step 2: synthesis van 11-{2-[2-(2-{2-[2-(2-methoxy-ethoxy)-ethoxy]-ethoxy}-ethoxy)-ethoxy]-ethoxy}-undec-1-ene In a dry three neck bottle comprising a magnetic stirrer and being kept under argon atmosphere 9.532 g (22 mmol) 2-[2-(2-{2-[2-(2-undec-10-enyloxy-ethoxy)-ethoxy]-ethoxy}-ethoxy)-ethoxy]-ethanol together with a small excess NaH is dissolved in 100 ml THF and 60 ml DMF and is stirred for 50 minutes.

4.09 ml (66 mmol) methyliodide is added and the reaction mixture is stirred overnight.

Then, the reaction is quenched with methanol.

Methanol, THF and DMF are removed at the rotavapor.

The solution is then dissolved in 200 ml dichloromethane, extracted and washed three times with $H_2O$.

The organic phase is dried with $MgSO_4$ and put at the rotavapor.

The product thus obtained is purified on a silica column with ethylacetate/MeOH (100/5).

The product is then concentrated on the rotavapor.

Yield=5.312 g (12 mmol)=54%.

Observations and Results

Colour change during 50 minutes stirring from light yellow to darker brown (T ↑).

High temperature+stronger vacuum for removing MeOH and DMF→precipitates due to NaBr After addition of brine→better separation First product from the silica column is the required product (only visible using $I_2$).

Figure 26:
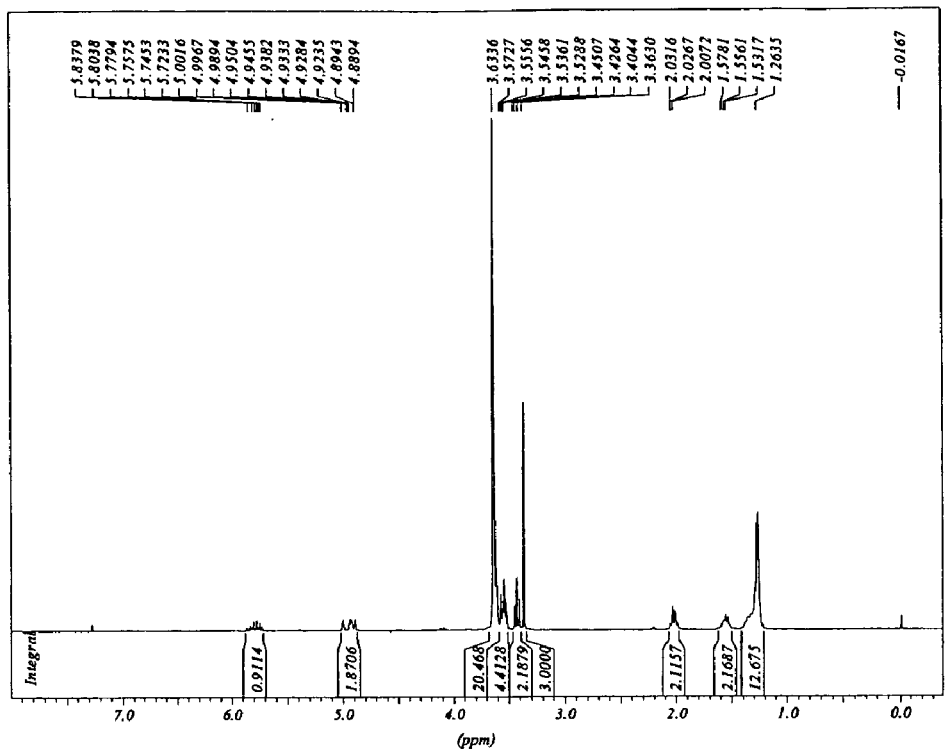
FIG. 26 illustrates the $^1$H NMR-spectrum of the intermediate product formed in the second step of the synthesis of trichloro-(11-{2-[2-(2-{2-[2-(2-methoxy-ethoxy)-ethoxy]-ethoxy}-ethoxy)-ethoxy]-ethoxy}-undecyl)-silane.

$^1$H NMR Spectrum (See FIG. 26)

5.79 and 4.94 ppm=hydrogens of =CH and =$CH_2$

~3.66=H's of six $OCH_2CH_2$'s 3.37 (singlet)=H of $OCH_3$ 1.2-2.1=H's of other $CH_2$'s Step 3: synthesis of trichloro-(11-{2-[2-(2-{2-[2-(2-methoxy-ethoxy)-ethoxy]-ethoxy}-ethoxy)-ethoxy]-ethoxy}-undecyl)-silane In a dry ampoule, 1.532 g (3.4 mmol) 11-{2-[2-(2-{2-[2-(2-methoxy-ethoxy)-ethoxy]-ethoxy}-ethoxy)-ethoxy]-ethoxy}-undec-1-ene is dissolved in toluene and evaporated twice using the rotavapor twice after which the product is dried.

A magnetic stirrer is added and the ampoule is closed with a septum while being kept under argon atmosphere.

1 ml of 0.01M solution of $H_2PtCl_6$ (0.0043 g) in dried tetrahydrofuran (THF) together with 40 ml (3.9 mmol) $HSiCl_3$ is then added and the reaction mixture is stirred overnight at 90° C.

The reaction product is dissolve in toluene and then the toluene is removed.

Yield=1.96 g (3.35 mmol)=98%.

Observations and Results

After addition of HSiCl3→gas+brown and a black precipitate is present in the solution.

Figure 27:
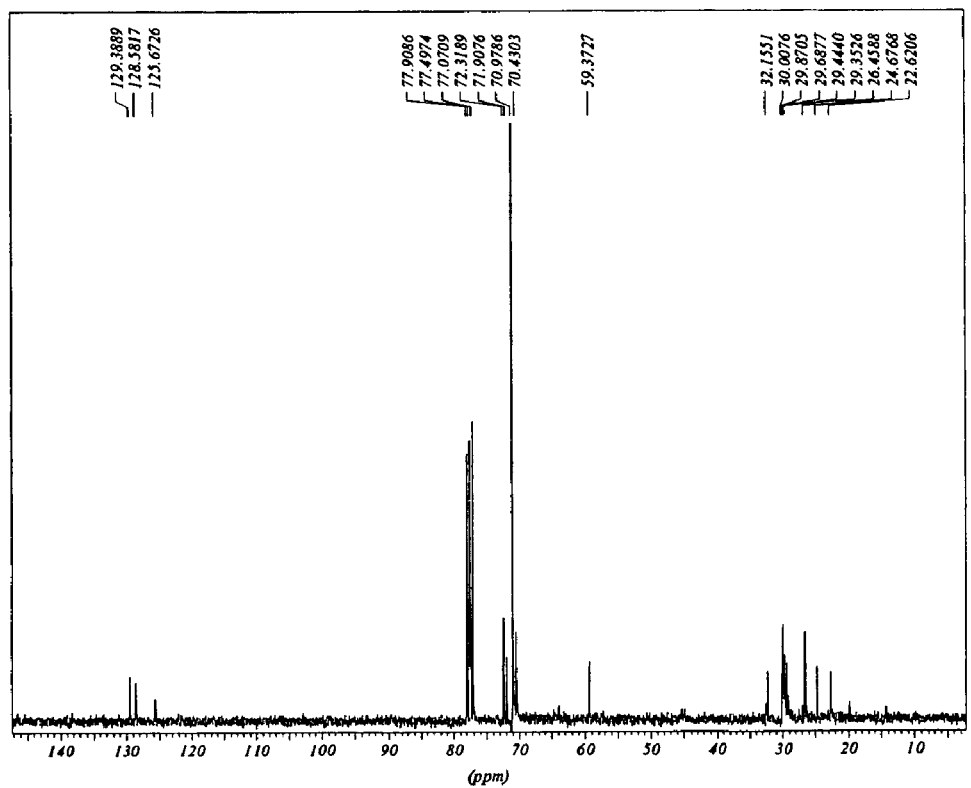
FIG. 27 and FIG. 28 respectively illustrate the $^1$H NMR-spectrum and the $^{13}$C NMR spectrum of trichloro-(1'-{2-[2-(2-{2-[2-(2-methoxy-ethoxy)-ethoxy]-ethoxy}-ethoxy)-ethoxy]-ethoxy}-undecyl)-silane.

$^1$H NMR Spectrum (See FIG. 27)

No more peaks for C=C

~3.66 ppm=H's of $OCH_2CH_2$'s 3.45 (triplet)=H of $CH_2$'s next to $OCH_2CH_2$ 3.4 ppm=H of $OCH_3$ Others=H's of other $CH_2$'s (shifted because of $Si(Cl)_3$)

Figure 28:
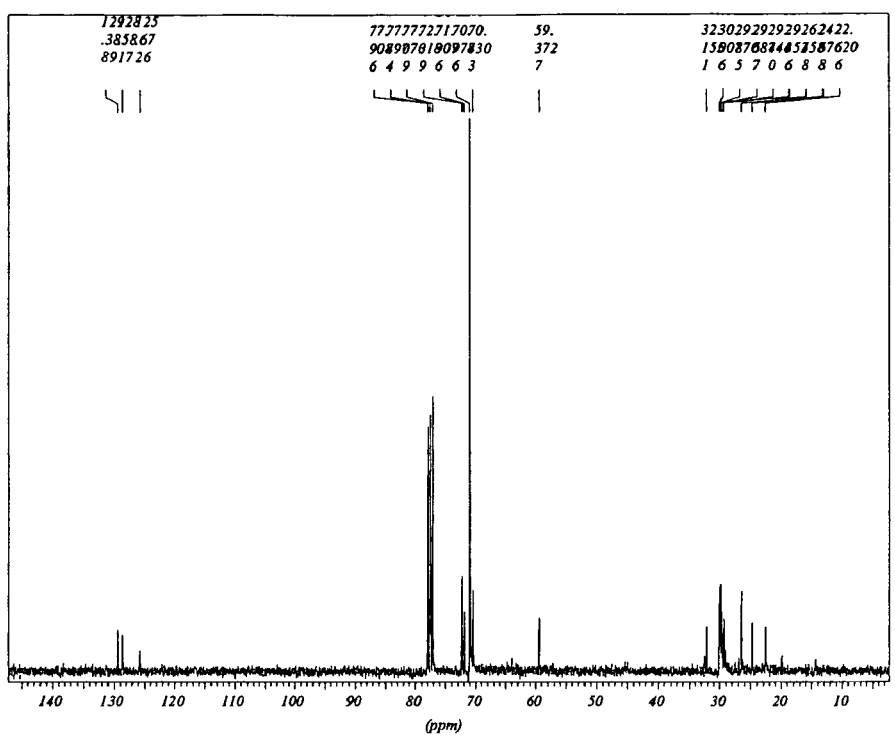

$^{13}$C NMR Spectrum (See FIG. 28)

No more peaks for C=C 70.9 ppm=sp carbons of six $OCH_2CH_2$'s 59.37 ppm=carbon of $OCH_3$ 29.44 ppm=carbons of other $CH_2$'s 24.68 ppm and 22.62 ppm=$sp^3$ carbons next to $Si(Cl)_3$ For the preparation of the triethoxy variant, where $Cl_3Si$ is replaced by $OEt_3Si$ in formula (6), (7) and (8), the same procedure as described above can be followed wherein $HSiOEt_3$ is used as a reagent instead of $HSiCl_3$.

In other examples of this second embodiment of the third aspect, the second silane molecules can have a shorter chain length compared to the first silane molecule. The term 'chain length' is understood as total length, i.e., alkyl chain plus oligo(ethylene oxide) chain. This implies that the number of repetitive units n+(3*n) is equal or higher than 0+(3*r).

In a fourth aspect, the use of homogeneous and mixed SAMs of silane molecules in biosensor and micro-array applications is provided.

In one embodiment of this fourth aspect, the surface of a biosensor can be modified with a homogeneous monolayer formed from silane molecules according to the first aspect and thus having a general structure as illustrated in formula (1). The monolayer then serves for the immobilisation of biological moieties. The pre-activated silane molecules preferably bind an NH$_2$— or a SH-group of a biological moiety to the Y group of the activate silane, leading to the formation of a covalent bond.

In another embodiment of the fourth aspect, the surface of a biosensor can be modified with a mixed silane layer comprising at least first and second silane molecules of which at least the first silane molecules are silane molecules according to the first aspect having formula (1). The mixed silane layer furthermore comprises second silane molecules which can have a structure as illustrated in formula (4).

The first and second silane molecules can comprise different pre-activated groups and hence, can bind to different biological moieties. The first silane molecules combine pre-activated and protein-resistant functionalities, as was discussed in the first aspect. Furthermore, the second silane molecule can be such that it further lowers protein binding to the surface of the biosensor.

The biological moieties bind to the silane molecules which form an interface layer of the biosensor are able to selectively interact with an analyte comprising, for example, target molecules to be detected. These biological moieties that are reacted with the surface can be, but are not limited to, biomolecules comprising a —NH$_2$ group wherein the —NH$_2$ group is covalently bound to the Y group of the homogeneous or to the Y group of the mixed silane film. Besides biological moieties with an —NH$_2$ group, other functional groups of the biological moiety, such as SH—, HOOC— and HO—, can be bound to the Y group of the silane molecule.

In embodiments of the fourth aspect, the binding of a biological moiety to the Y group of silane molecules present at the surface of a biosensor can require an extra step, wherein a cross-linker molecule is bound to the Y and the biological moiety. After the covalent immobilisation of, e.g., antibodies, the remaining reactive Y groups on the silane molecules are preferably reacted with, for example, ethanolamine or (PEO)$_x$-monoamine (with x=2, 3, 4, or more) in order to avoid non-specific binding of unwanted biological moieties in a next stage.

In a further aspect, the silane molecules as discussed in the first aspect can also be used for coating nanoparticles. In that case, the nanoparticles become protein-resistant and at the same time can be bound to biological moieties suitable for recognising diseases such as, e.g., cancer.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A silane molecule having the general formula:

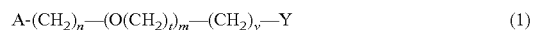

wherein

A is selected from the group consisting of X$_3$Si, X$_2$R$^1$Si, and XR$^1$R$^2$Si, wherein X is a halo group or an alkoxy group, and R$^1$ and R$^2$ are each independently an alkyl chain, Y is a conjugated carbonyl, and n is an integer from 6 to 22, m is an integer from 0 to 50, v is an integer from 0 to 5, and t is an integer from 1 to 10.

2. The silane molecule according to claim 1, wherein Y is a conjugated carbonyl selected from the group consisting of fluoro substituted benzoate, pentafluorophenylester, N-hydroxysuccinimide ester, acid halogenide, and maleimide.

3. The silane molecule according to claim 1, wherein A is Cl$_3$Si— or EtO$_3$Si—.

4. The silane molecule according to claim 1, wherein at least one pair of adjacent —CH$_2$— moieties in the group (CH$_2$)$_n$ are separated from each other by at least one heteroatom, such that the group (CH$_2$)$_n$ comprises p heteroatoms, with p being such that n+p is an integer from 6 to 22.

5. The silane molecule according to claim 1, wherein at least one pair of adjacent —CH$_2$— moieties in the group (CH$_2$)$_v$ are separated from each other by at least one heteroatom, wherein (CH$_2$)$_v$ is a spacer and comprises q heteroatoms, with q being such that v+q is an integer from 0 to 5.

6. A method for synthesizing a silane molecule, the method comprising:

reacting an alcohol of formula (2)

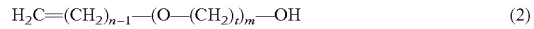

wherein n is an integer from 6 to 22, m is an integer from 0 to 50, and t is an integer from 0 to 5, with a compound of a formula selected from the group consisting of Cl—(CH$_2$)$_v$—Y and Br—(CH$_2$)$_v$—Y, wherein v is an integer from 0 to 5 and Y is a conjugated carbonyl, whereby an intermediate of formula (3) is obtained; and

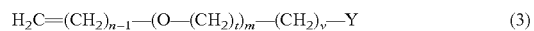

reacting the intermediate of formula (3) with a compound of formula A-H, wherein A is selected from the group consisting of X$_3$Si, X$_2$R$^1$Si, and XR$^1$R$^2$Si, X is a halo group or an alkoxy group, and R$^1$ and R$^2$ are each independently an alkyl chain, whereby a silane of formula (1) is obtained:

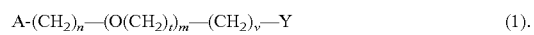

7. The method according to claim 6, wherein Y is a conjugated carbonyl selected from the group consisting of fluoro substituted benzoate, pentafluorophenylester, N-hydroxysuccinimide ester, acid halogenide, and maleimide.

8. The method according to claim 6, wherein A is $Cl_3Si-$ or $EtO_3Si-$.

9. The method according to claim 6, wherein at least one pair of adjacent $-CH_2-$ moieties in the group $(CH_2)_n$ are separated from each other by at least one heteroatom, such that the group $(CH_2)_n$ comprises p heteroatoms, with p being such that n+p is an integer from 0 to 30.

10. The method according to claim 6, wherein at least one pair of adjacent $-CH_2-$ moieties in the group $(CH_2)_v$ are separated from each other by at least one heteroatom, wherein $(CH_2)_v$ is a spacer and comprises q heteroatoms, with q being such that v+q is an integer from 0 to 5.

11. The silane molecule according to claim 1, wherein Y is fluoro substituted benzoate.

12. The silane molecule according to claim 1, wherein Y is pentafluorophenylester.

13. The silane molecule according to claim 1, wherein Y is N-hydroxysuccinimide ester.

14. The silane molecule according to claim 1, wherein Y is acid halogenide.

15. The silane molecule according to claim 1, wherein Y is maleimide.

16. The silane molecule according to claim 1, wherein A is $X_3Si$, wherein X is a halo group or an alkoxy group.

17. The silane molecule according to claim 1, wherein A is $X_2R^1Si$, wherein X is a halo group or an alkoxy group, and $R^1$ is an alkyl chain.

18. The silane molecule according to claim 1, wherein A is $XR^1R^2Si$, wherein X is a halo group or an alkoxy group, and $R^1$ and $R^2$ are each independently an alkyl chain.

19. The method according to claim 6, wherein Y is fluoro substituted benzoate.

20. The method according to claim 6, wherein Y is pentafluorophenylester.

21. The method according to claim 6, wherein Y is N-hydroxysuccinimide ester.

22. The method according to claim 6, wherein Y is acid halogenide.

23. The method according to claim 6, wherein Y is maleimide.

24. The method according to claim 6, wherein A is $X_3Si$, wherein X is a halo group or an alkoxy group.

25. The method according to claim 6, wherein A is $X_2R^1Si$, wherein X is a halo group or an alkoxy group, and $R^1$ is an alkyl chain.

26. The method according to claim 6, wherein A is $XR^1R^2Si$, wherein X is a halo group or an alkoxy group, and $R^1$ and $R^2$ are each independently an alkyl chain.

27. The silane molecule according to claim 1, wherein t is an integer from 1 to 5 and in is an integer from 3 to 22.

28. The method according to claim 6, wherein t is an integer from 1 to 5 and m is an integer from 3 to 22.

* * * * *